US012806279B2

(12) United States Patent
Chen

(10) Patent No.: US 12,806,279 B2
(45) Date of Patent: Nov. 24, 2026

(54) SMALL MOLECULE-NANOBODY CONJUGATE INDUCERS OF PROXIMITY (SNACIP) AND PREPARATION METHODS AND USE THEREOF

(71) Applicant: Harbin Institute of Technology, Harbin (CN)

(72) Inventor: Xi Chen, Harbin (CN)

(73) Assignee: Harbin Institute of Technology, Harbin (CN)

( * ) Notice: Subject to any disclaimer, the term of this patent is extended or adjusted under 35 U.S.C. 154(b) by 221 days.

(21) Appl. No.: 17/989,785

(22) Filed: Nov. 18, 2022

(65) Prior Publication Data

US 2023/0414776 A1 Dec. 28, 2023

(30) Foreign Application Priority Data

May 7, 2022 (CN) ........................ 202210495991.X

(51) Int. Cl.
*A61K 47/68* (2017.01)
*A61K 47/64* (2017.01)

(52) U.S. Cl.
CPC ........ *A61K 47/6843* (2017.08); *A61K 47/645* (2017.08); *A61K 47/6803* (2017.08); *A61K 47/6889* (2017.08)

(58) Field of Classification Search
None
See application file for complete search history.

(56) References Cited

PUBLICATIONS

Lloyd et al. Protein Engineering, Design & Selection 22:159-168 (Year: 2009).*
Edwards et al., J Mol Biol. 334(1): 103-118 (Year: 2003).*
Piche-Nicholas et al MABS 10(1): 81-94 (Year: 2018).*
Sun et al., Nature Communications 14: 1635 (Year: 2023).*

* cited by examiner

*Primary Examiner* — Phuong Huynh
(74) *Attorney, Agent, or Firm* — IPro, PLLC; Na Xu

(57) ABSTRACT

The disclosure discloses small molecule-nanobody conjugate inducers of proximity (SNACIP) and preparation methods and use thereof, and belongs to the technical field of cell regulation. Chemical inducers of proximity (CIPs) induce dimerization between proteins to regulate biological progresses. However, the CIP has the disadvantages of difficulties in directly regulating endogenous proteins without ligand binding sites, background activity interference of endogenous proteins, difficulties in use for drug development, etc. The SNACIP disclosed herein includes a nanobody targeting moiety, a small molecule binding motif, an intracellular delivery moiety and a linker. In the disclosure, a cRGT general inducer has the advantages of easy cell penetration, rapidity, reversibility, thorough regulation, and dose-dependence; a cRTC-type inducer can specifically regulate an intrinsically disordered protein in the cell; and a bivalent nanobody CTTC inducer is suitable for use in vivo. The SNACIP is a new-generation regulatory inducer of proximity with extensive and extremely important use value.

1 Claim, 35 Drawing Sheets

Specification includes a Sequence Listing.

HPLC Chromatograph (C18, λ=220 nm, $1 ml \cdot min^{-1}$)

| Rank | Time | Area | Conc. |
|---|---|---|---|
| 1 | 12.662 | 106763.656 | 1.2435 |
| 2 | 12.907 | 8478924.000 | 98.7565 |
| Total | | 8585687.656 | 100 |

SMALL MOLECULE-NANOBODY CONJUGATE INDUCERS OF PROXIMITY (SNACIP) AND PREPARATION METHODS AND USE THEREOF

REFERENCE TO SEQUENCE LISTING

The instant application contains a Sequence Listing in XML format as a file named "USAAA211729.xml", created on Dec. 30, 2025, of 26,618 bytes in size, and which is hereby incorporated by reference in its entirety.

TECHNICAL FIELD

The disclosure belongs to the technical field of cell regulation, and in particular relates to small molecule-nanobody conjugate inducers of proximity (SNACIP) and preparation methods and use thereof.

BACKGROUND

Proximity-inducing mechanisms control many cellular processes, including protein-protein interactions, signaling cascades, enzymatic catalytic reactions, post-translational modifications, regulated protein degradation, etc. Chemical inducers of proximity (CIPs) or chemical inducers of dimerization (CIDs) use bifunctional small molecules to induce dimerization between two proteins, and further realizes regulation of cellular processes, including cell signal transduction, selective autophagy, localization control of proteins and organelles, axonal transport and cell-cell adhesion, as well as use in cell therapy, etc. However, CIPs generally require an additional binding tag to be fused to a protein to be regulated by exogenous gene expression. Therefore, the CIP technology has the disadvantages that endogenous proteins, in particular those proteins without ligand binding sites are difficult to directly regulate, background activity of endogenous proteins to be regulated has interference, and CIP inducers are difficult to be converted into drug molecules, because genetic augmentation and modification of individuals are generally not allowed during therapeutic intervention due to ethical and risk issues.

It is difficult for a small molecule-nanobody conjugate to penetrate a cell, so it cannot be directly used for regulating intracellular processes. The small molecule-nanobody conjugate needs to be chemically functionalized to penetrate a cell. Conventional intracellular delivery vectors, such as linear cell-penetrating peptides (CPP), and other relatively novel intracellular delivery vectors, such as engineered C3 protein toxins, mostly achieve intracellular delivery by endocytosis. In addition to being relatively slow, endocytosis is inevitably accompanied by processes such as endosome entrapment and lysosomal degradation. Recently, cyclic cell-penetrating peptides have been found to deliver cargos into cells more rapidly in a non-endocytic form. Microtubule nucleation in spindle assembly is important for sustaining life, and dysregulation of this nucleation process is implicated in a variety of diseases. Although microtubule targeting agents (MTAs) that directly bind to microtubules have been successfully used in cancer treatment in chemotherapy, the development of agents that regulate the microtubule nucleation process remains challenging. The microtubule nucleation process involves concerted actions of multiple protein complexes and several intrinsically disordered protein factors, which make it difficult to develop corresponding small-molecule regulatory agents via, e.g. structure-guided drug design (SGDD).

SUMMARY

The objective of the disclosure is to develop a new type of intracellular inducers of proximity with core advantages for regulating intracellular processes, which have the value of drug development.

The disclosure provides small molecule-nanobody conjugate inducers of proximity, i.e., SNACIP inducers, including a small molecule binding motif, a nanobody targeting moiety, an intracellular delivery moiety and a linker, the general formula of the inducers being as follows: small molecule binding motif-nanobody targeting moiety-linker-intracellular delivery moiety.

More specifically, the small molecule binding motif is directly introduced by chemical ligation, or is indirectly introduced based on a post-translational modification mechanism after entering a cell; the nanobody is a monovalent or bivalent nanobody; and the intracellular delivery moiety is a cyclic cell-penetrating peptide (CPP) or a linear CPP.

More specifically, the intracellular delivery moiety is cyclic decaarginine or a Tat polypeptide sequence.

More specifically, the cyclic cell-penetrating peptide has a structure containing a cyclic (KrRrRrRrRrRE) moiety or cR10* for short, wherein the K and E residues are preferably cyclic with an amide bond, and the C-terminal end is preferably a —$CONH_2$ group.

More specifically, Cys-$(Gly)_n$-cyclic(KrRrRrRrRrRE)-$NH_2$, n being zero or a natural number, r: L-Arg, R: L-Arg, has a structural formula as follows:

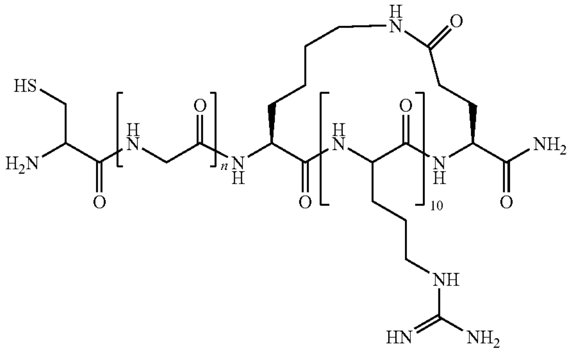

n = 0, 1, 2, 3, ....

More specifically, in Cys-$(Gly)_n$-cyclic(KrRrRrRrRrRE)-$NH_2$, n=5.

More specifically, the nanobody is a fluorescent protein nanobody or a nanobody for an intracellular target that mediates cellular processes.

More specifically, the fluorescent protein nanobody is a green fluorescent protein nanobody (GBP) or a red fluorescent protein nanobody (RBP); and the nanobody for an intracellular target that mediates cellular processes is a nanobody for a relevant target of a cell division pathway, a nanobody for a relevant target of a tumor cell invasion pathway, a nanobody for relevant targets of various pathways of ferroptosis, or a nanobody for relevant targets related to cytoskeleton functions.

More specifically, the small molecule binding motif is a protein tag binding ligand or an intracellular binding moiety capable of being introduced through post-translational modification of protein.

More specifically, the protein tag binding ligand is trimethoprim (TMP) or chlorohexyl; and the intracellular binding moiety capable of being introduced through post-translational modification of protein is prenyl or myristoyl.

More specifically, the linker is a disulfide bond, a thioether bond, or a peptide bond.

More specifically, the small molecule binding motif is trimethoprim (TMP), the intracellular delivery moiety is cyclic decaarginine cR10*, and the linker is a reducible broken disulfide bond, that is, the inducer is cR10*-GBP-TMP.

More specifically, the inducer is a latent SNACIP inducer, and is converted into a functional farnesyl-cRTC inducer after entering cells, the nanobody is a TPX2 binding protein (TBP), the small molecule binding motif is a CAAX-box polypeptide sequence capable of being prenylated, the intracellular delivery moiety module is cyclic decaarginine cR10*, and the linker is a thioether bond generated via the reaction between maleimide and sulfhydryl, that is, the inducer is cR10*-TBP-CAAX.

More specifically, the inducer is a latent SNACIP inducer, and is converted into a functional farnesyl-CTTC inducer after entering cells, the nanobody is a bivalent TBP nanobody, the small molecule binding motif is a CAAX-box polypeptide sequence capable of being prenylated, the intracellular delivery moiety is cyclic decaarginine cR10*, and the linker is a peptide bond —NHCO—, that is, the inducer is mCherry-CPP-2×TBP-CAAX.

The disclosure provides a method for inducing proximity inside a cell, including the following steps:

(1) selecting a nanobody targeting moiety recognized by target protein in the cell;
(2) selecting a small molecule binding motif having a binding effect on target protein or phospholipid in the cell or introducing a small molecule binding motif through post-translational modification;
(3) performing bioconjugation on the nanobody targeting moiety in step (1) and the small molecule binding motif in step (2) to obtain a conjugate, or performing fusion expression on the nanobody targeting moiety in step (1) and the small molecule binding motif introduced by post-translational modification in step (2) to obtain a chimera;
(4) performing bioconjugation or fusion expression on the intracellular delivery moiety and the conjugate or the chimera obtained in step (3) to obtain an SNACIP inducer; and
(5) adding the SNACIP inducer obtained in step (4) into a cell system to induce the proximity inside the cell.

The disclosure provides use of the SNACIP inducers in regulating cellular processes.

More specifically, the use is for preparation of antitumor drugs.

More specifically, the use is for activation and deactivation of intracellular proteins.

The disclosure provides a kit for regulating cellular processes, including any of the aforementioned SNACIP inducers, for regulating cellular processes.

The disclosure provides a nanobody drug for treating tumors, including any of the aforementioned SNACIP inducers, and blocking cell division by targeting and deactivating TPX2, thereby inhibiting tumor proliferation.

The disclosure provides a nanobody drug for treating tumors, including any of the aforementioned SNACIP inducers, and blocking cell division by targeting and deactivating TPX2, thereby inhibiting tumor proliferation.

The disclosure provides a method for inhibiting cell division by targeting a microtubule nucleator TPX2 protein to deactivate the TPX2, and a means derived therefrom for developing drugs for treating tumor.

The disclosure provides a method for activating and deactivating intracellular proteins using a nanobody conjugate by using any of the aforementioned SNACIP inducers, which achieves activation by localizing a protein to be regulated to a functional location of a plasma membrane, or achieves deactivation by localizing a protein to be regulated in a non-functional location of a plasma membrane.

The disclosure provides a method for regulating ferroptosis by using any of the aforementioned SNACIP inducers, which localizes GPX4 to a peroxisome, such as a PEX3 sequence, to induce ferroptosis, as a new strategy for the treatment of tumors.

In the disclosure, three different SNACIP inducers are specifically demonstrated, which represent different application types respectively and have their own characteristics.

The first is an inducer cR10*-GBP-TMP, cRGT for short, which can quickly penetrate a cell ($t_{1/2}$=7.3 min), and induce dimerization between an intracellular green fluorescent protein (GFP) mutant and *E. coli* dihydrofolate reductase (eDHFR, SEQ ID NO:5), thereby realizing regulation of intracellular cellular processes. The cRGT features as a general SNACIP for regulating cellular processes, and has the advantages of being fast, reversible, no-wash, dose-dependent, and complete in regulation, which will be described in the Examples. cRGT can control cell localization, regulate the cell signal transduction process, regulate the transport of intracellular cargo, and regulate one of the current research fronts and hotspots-ferroptosis.

The second is a latent SNACIP inducer, cR10*-TBP-CAAX, cRTC for short, which is developed for the important microtubule nucleation process. With the help of the post-translational modification mechanism of cells, the latent cRTC can be linked with farnesyl after entering the cell, thereby being converted into a functional farnesyl-cRTC inducer of proximity. cRTC deactivates TPX2 by localizing an intrinsically disordered protein TPX2, which is also a key microtubule nucleator, to a non-functional location of the plasma membrane, thereby inhibiting microtubule nucleation, blocking cell division, and inhibiting cancer cell proliferation. The cRTC is valued as the first regulator of microtubule nucleation and for its capability of inhibiting cancer cell proliferation, and is also an important example of direct regulation of endogenous targets without ligand binding.

The third is a bivalent SNACIP for in vivo use, mCherry-CPP-2×TBP-CAAX, CTTC for short. The inducer includes a bivalent TBP nanobody, so it is more suitable for use in vivo. CTTC can also be post-modified and converted into farnesyl-CTTC after entering cells, deactivate the microtubule nucleator TPX2, and inhibit cancer cell proliferation, showing an effect of inhibiting tumor proliferation in vivo. This result confirms that SNACIP inducers may not only directly regulate endogenous proteins, but also may be developed into nanobody drugs for treatment of diseases.

Compared to the relevant chemical inducers of proximity (CIPs), SNACIP have several advantages and are summarized in the following table.

| Entry | Feature | SNACIPs | CIPs/CIDs | Additional Notes |
|---|---|---|---|---|
| 1 | Direct modulation of endogenous protein | Yes, shown in this study. | Limited | CIP or CID typically requires ectopically expression of protein tags fused with proteins of interest. |
| 2 | Translational potential | Yes, shown in this study | Limited | Because CIPs typically require genetic modification of cells to introduce binding tags. |
| 3 | Binding affinity | Can be very high. Nb: nM to pM affinity. In this study, GBP: Kd = 1.4 nM; TMP: Ki = 1.3 nM. | Generally moderate. One of the strongest CIP, rapamycin, induces dimerization between FKBP and FRB at 13 nM affinity. | High affinity dimerization is beneficial to achieve more complete degrees of dimerization, hence minimizing basal activities. |
| 4 | Tag size | Can be 0 | Protein tags with usually over 10 kD are required; and an additional FP tag is typically needed for visualization | Fusion additional tags onto a protein could cause unfavorable effects to POI. For example, shield the protein's activity via steric hindrance, alter a protein's physiological behaviors, and may cause protein precipitations. More critically, if both N- and C-terminus of a protein are essential for the function, the applications using CIP method would be further restricted. |
| 5 | Reversibility | Readily and multi-round reversible | Those CIP molecules with high binding affinity is typically not reversible, such as rapamycin. | The readily available, highly cell-permeable, low-cost TMP molecule acts as an ideal shuttle to facilely and rapidly induce dedimerization, and enable re-dimerization after wash-out. Hence, multi-round reversible control can be achieved. |
| 6 | If widely and immediately applicable | Yes, because EGFP and mCherry are two most widely used FPs. In our study, we introduced cRGT and cRRT, which can directly modulate EGFP and mCherry fused proteins. | Specific constructs need to be designed and cloned. For establishing respective stable-cell lines, it takes months of work. | Since many cell lines using EGFP and mCherry as FP tags for visualization, cRGT and cRRT are potentially immediately applicable to control the protein target without the need to establish these cell lines. |
| 7 | Versatility | One stone, many birds | Typically, one stone, one bird. | For example, as for cRGT, it regulates mEYFP, EGFP and potentially many other EGFP variants with mutations not occurring at the binding surface. |
| 8 | Ease to use | Yes, directly add and imaging without worrying about reversing effect at higher dosages. No wash is needed, nor any additional illumination devices are required. | Some CIPs or CIDs require a certain incubation time, need thorough wash-out of excess of the inducer. Some CIPs show a "hook" effect and the concentration may not be easily controlled. | Here, SNACIP shares an appreciate feature of CIP. |

-continued

| Entry | Feature | SNACIPs | CIPs/CIDs | Additional Notes |
|---|---|---|---|---|
| 9 | Further extension | Yes. For example, simply change GBP to RBP, a new SNACIP inducer was prepared using not much of effort. | Usually fixed. | This feature further highlights the generally applicability of SNACIP concept. |

As can be seen from the above table, SNACIPs could be advantageous over traditional CID/CIP molecules in several aspects including: i) the ability to directly regulate endogenous proteins, ii) translational potential, iii) high binding affinity, iv) tag-size, v) versatility and others. Also, SNACIP shares some appreciable features of CIP, e.g., reversibility, ease to use, dose-dependent response, and others.

The SNACIP examples disclosed herein have the corresponding beneficial effects as follows:

A. The cRG inducer can quickly penetrate a cell (in several minutes) to achieve no-wash, reversible, dose-dependent, and thorough regulation of cell signal transduction, cellular processes, and programmed death.

B. The cRTC latent SNACIP can be converted into a functional farnesyl-cRTC inducer after entering cells, and can regulate intrinsically disordered protein targets.

C. The CTTC bivalent SNACIP can be converted into a functional farnesyl-CTTC inducer after entering cells. Because CTTC contains a bivalent nanobody, it is more suitable for use in vivo, can inhibit tumor proliferation, and may be developed into relevant nanobody drugs.

Figure 12A:
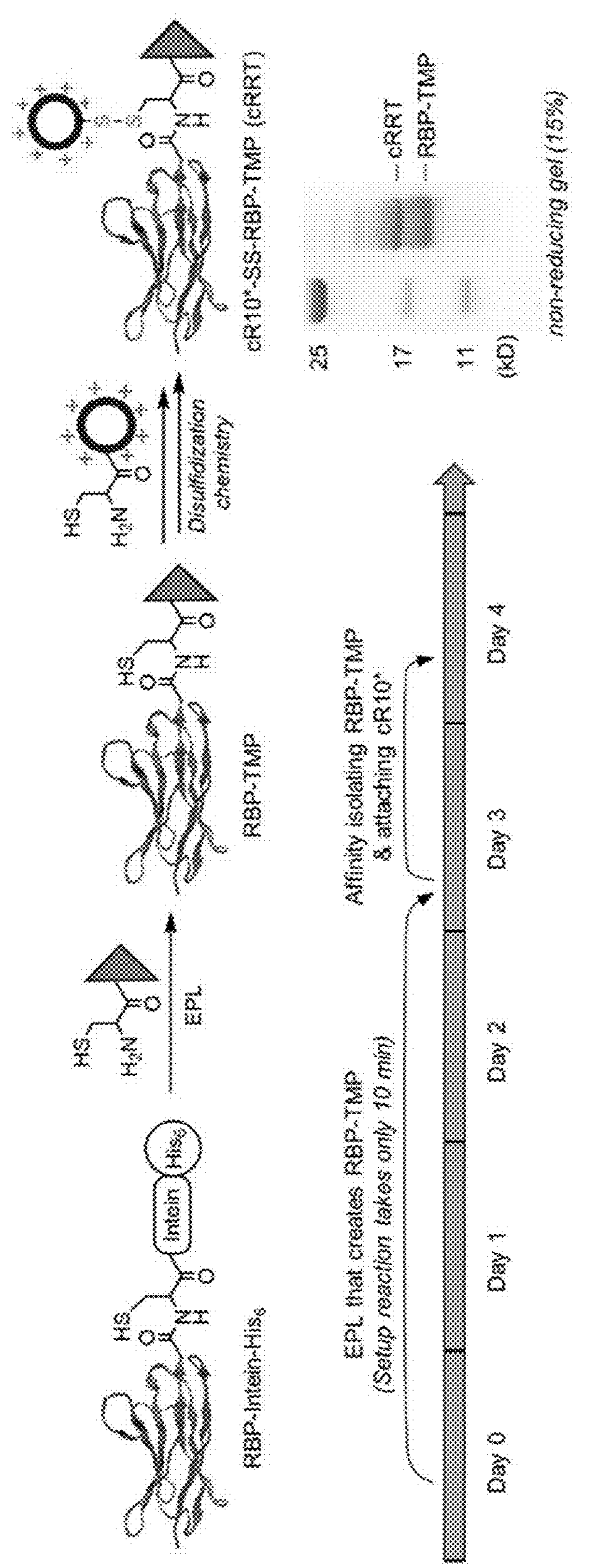

FIG. 12A shows design and facile assembly of a new SNACIP inducer, cR10*-SS-RBP-TMP (cRRT), for control of the protein-protein proximity. Schematic view of the assembly of cRRT via expressed protein ligation (EPL) and disulfidization chemistry similar to the preparation of cRGT. Schematic view of the time flow reveals that cRRT can be facilely assembled. Note that EPL requires less than 10 min to setup; hence in reality the assembly requires only two days of laboratory works. SDS-PAGE characterization of cRRT, which reveals ~60% portion of the cR10* conjugated cRRT.

Figure 12B:
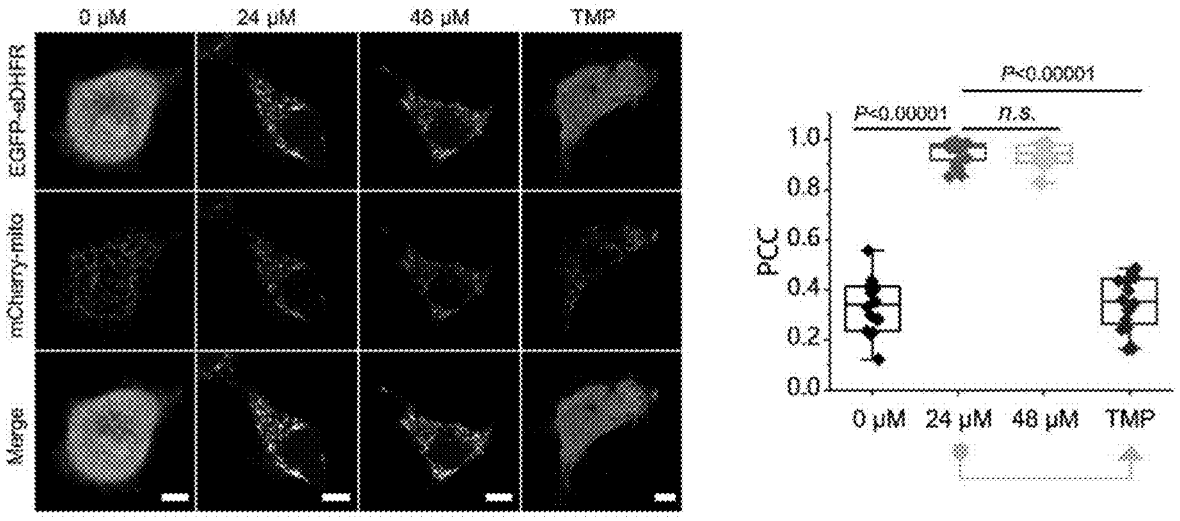

FIG. 12B shows that live HeLa cells coexpressing mCherry-mito and EGFP-eDHFR treated with cRRT (24 μM or 48 μM, 1.5 h) show a high-degree of dimerization close to 1.0; TMP (10 μM, 10 min) completely abolished the dimerization that was induced by cRRT (24 μM). Statistical PCC colocalization analysis was performed; one-sided Student's t-test was used. All scale bars: 10 μm.

Figure 13:
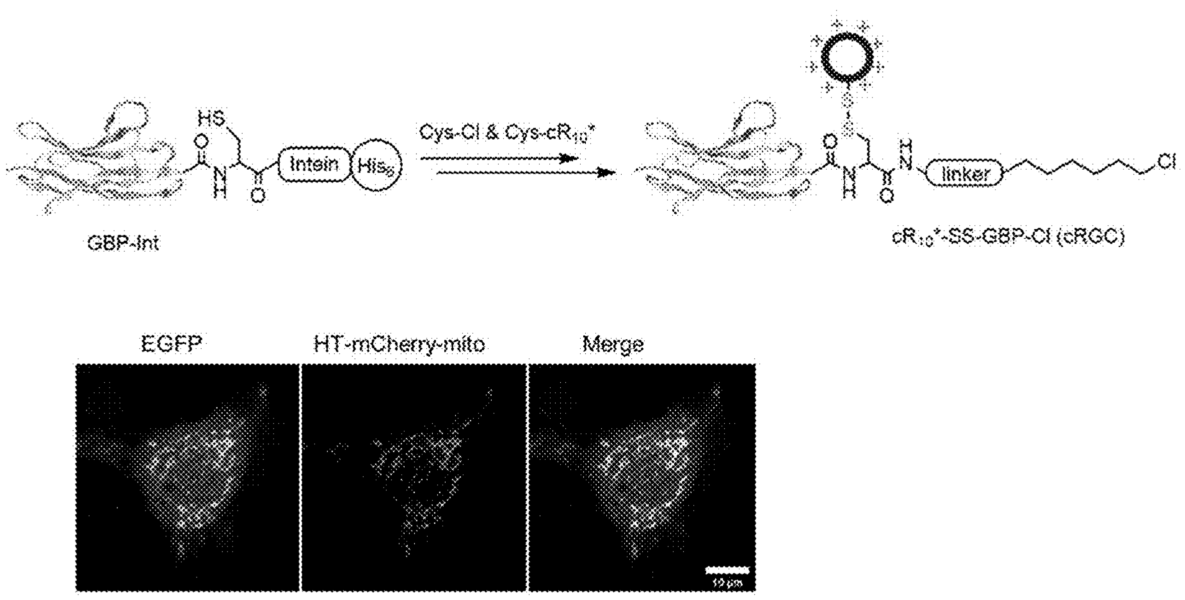

FIG. 13 shows design and preparation of another general-purpose SNACIP inducer, cR10*-SS-GBP-Cl (cRGC) for control of protein dimerization between EGFP and HaloTag. The characteristic feature of cRGC lies at the covalent interaction between cRGC and HaloTag which could allow more durable dimerization. a) Schematic view for the generation of cRGC inducer. b) Live HeLa cells co-expressing EGFP (green, cytosolic) and HT-mCherry-mito (HT: HaloTag; mitochondria targeting, red) were treated with cRGC (24 μM, 1.5 h), which led to the recruitment of EGFP to mitochondria. Scale bars: 10 μm.

Figure 14A:
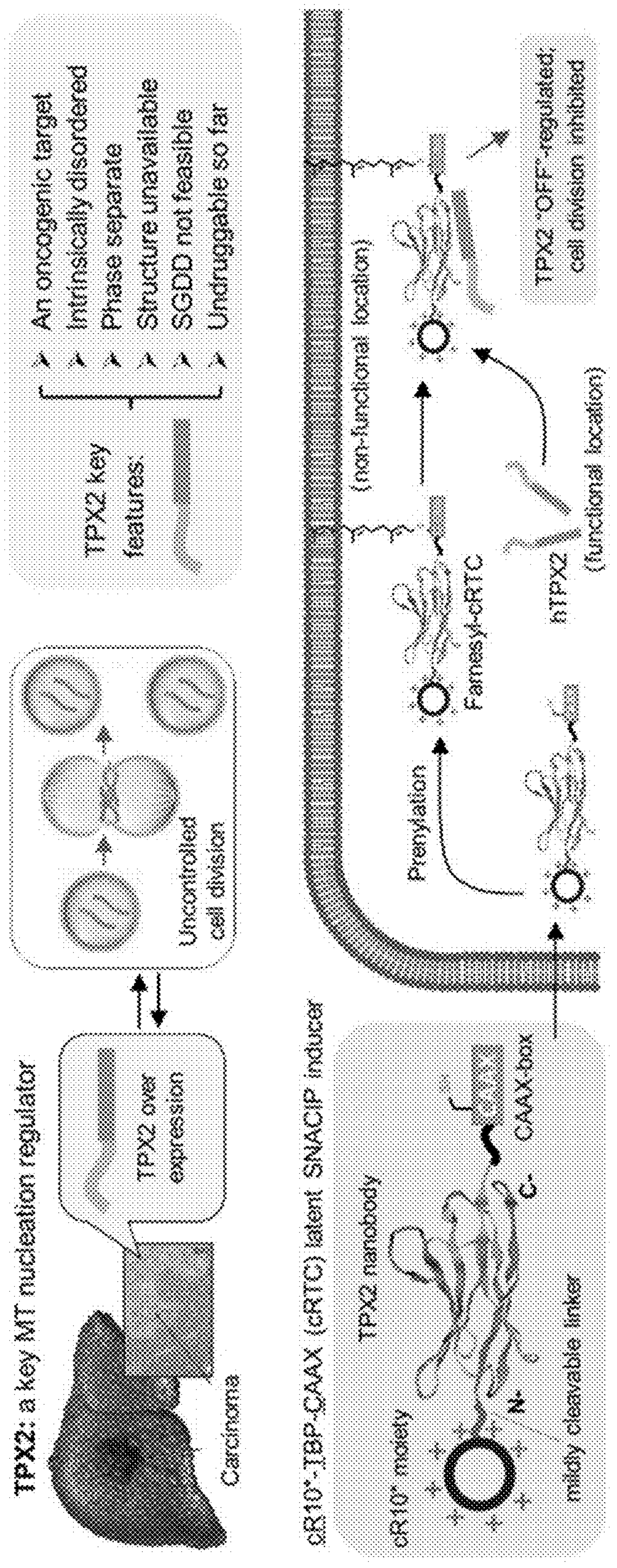

FIG. 14A shows design and preparation of a latent SNACIP inducer, cRTC, to deactivate the function of the microtubule nucleator TPX2 in cell division. TPX2 is an intrinsically disordered protein (IDP) that is overexpressed in many cancer cells and promotes uncontrolled cell division. Structural elements of the latent SNACIP inducer, cRTC, and a schematic diagram of how it regulates the TPX2 function were shown.

Figure 14B:
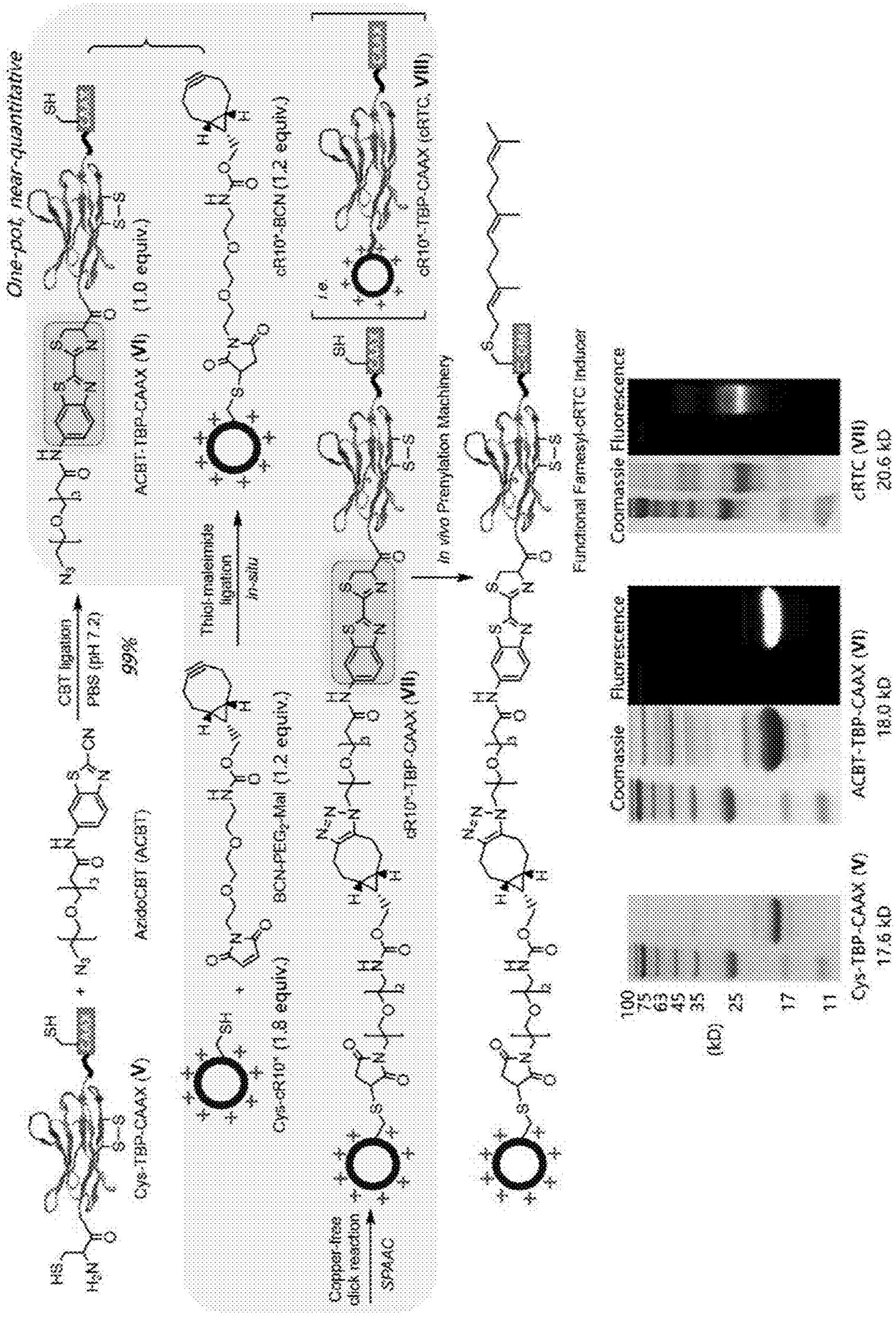

FIG. 14B shows one-pot high-yield fast preparation of cRTC by a tandem bioorthogonal reaction strategy based on equivalence control. When entering the cell, cRTC is converted into a functional farnesyl-cRTC inducer through a post-modification mechanism (abbreviations in the figure: BCN: bicyclonornyne, capable of undergoing a copper-free catalyzed click reaction with an azide group; Mal: maleimide, capable of undergoing an addition reaction with cysteine). The SDS-PAGE electrophoresis and in-gel fluorescence analysis of cRTC and its intermediate were shown.

Figure 14C:
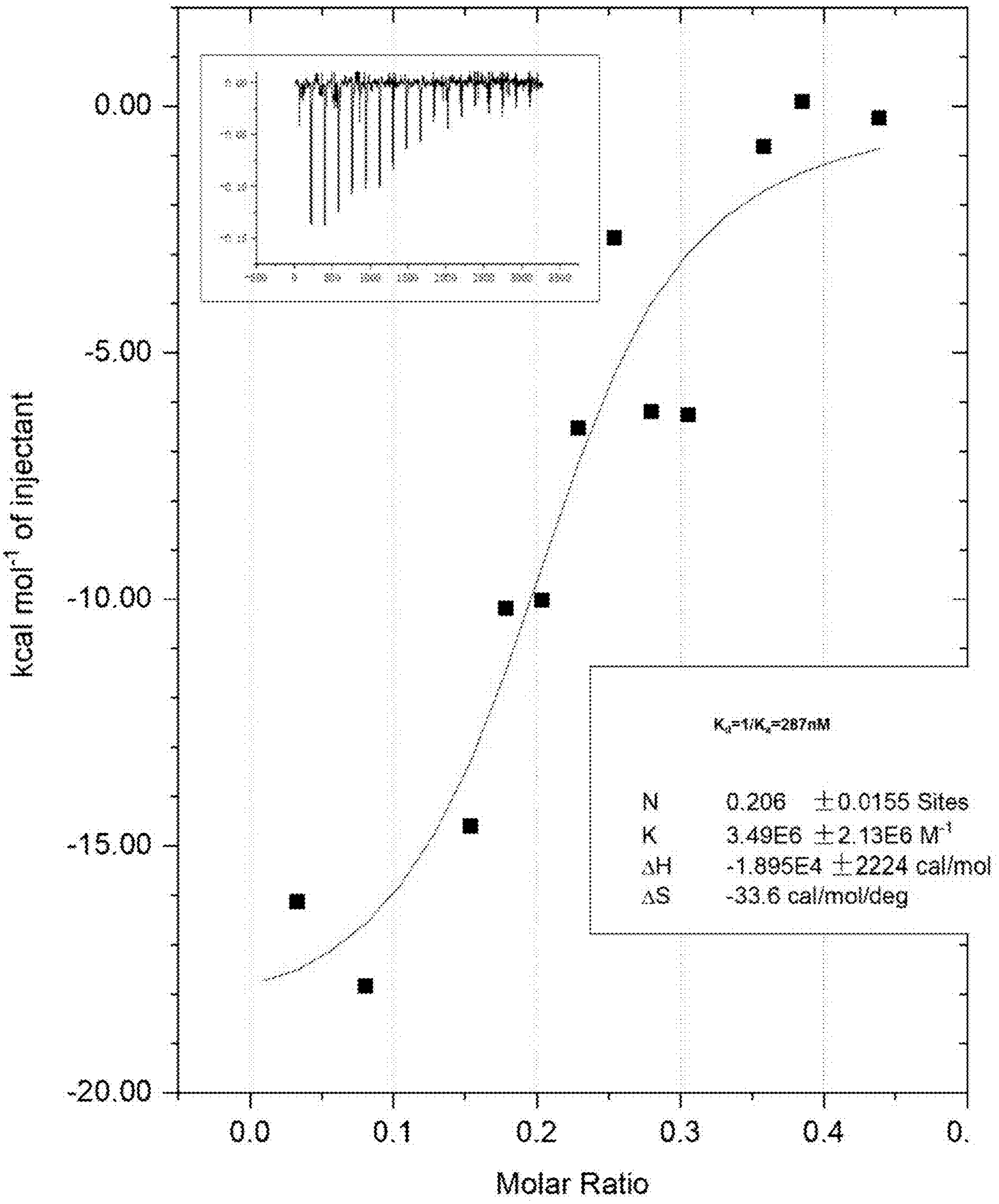

FIG. 14C shows a titration curve characterizing the interaction between TBP nanobody and hTPX2 protein by isothermal titration calorimetry (ITC) and the corresponding Wiseman Plot. The negative titration peak indicates that the binding is an exothermic process and thus the binding enthalpy change ΔH is negative. Via the Wiseman Plot, it can be deduced that $K_d=1/K_a=287$ nM, and the binding stoichiometric ratio of TBP to hTPX2 is 1:5. It is worth noting that the binding entropy change ΔS is also negative, implying that the binding process involves a large number of conformational changes, which is consistent with the characteristics of hTPX2 as a highly disordered protein.

Figure 15:
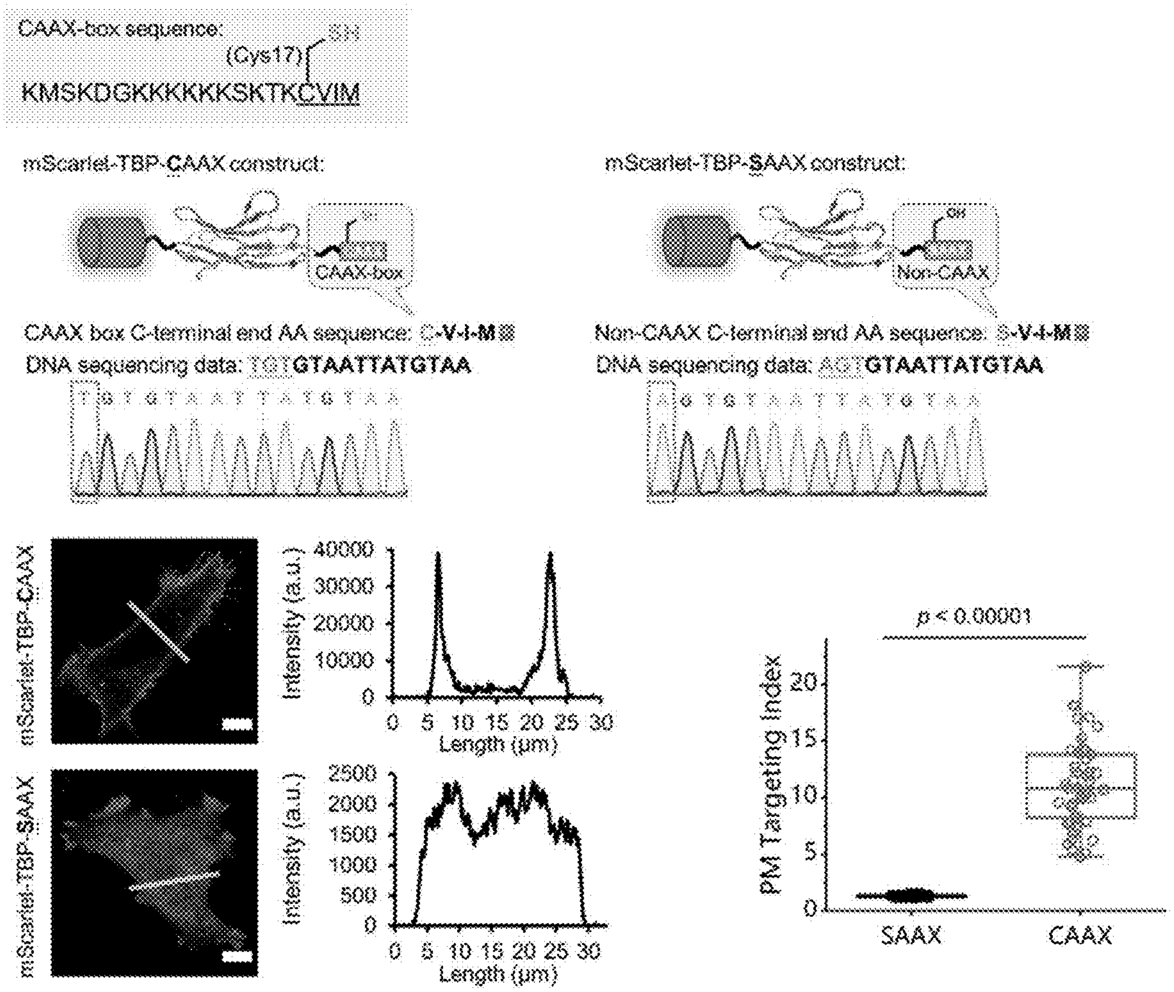

FIG. 15 shows that the cysteine residue 17, i.e., Cys17, in the CAAX-box of a TBP-CAAX construct, is responsive for prenylation for post-translational modification. The amino acid sequence of the CAAX-box and the sequence of the last four amino acids at the C-terminal end of the mScarlet-TBP-CAAX construct and the corresponding DNA sequencing data were shown. Also the sequence of the last four amino acids at the C-terminal end of the mScarlet-TBP-SAAX construct and the corresponding DNA sequencing data, showed that after the Cys17 residue responsive for prenylation was mutated to Ser17, the corresponding prenylation could not be carried out to achieve plasma membrane localization. Based on confocal micrographs and corresponding streak analysis (from left to right), the mScarlet-TBP-CAAX had strong and clear PM localizing ability. In contrast, the mScarlet-TBP-SAAX mutant completely lost the PM localizing ability. Statistical comparative analysis of PM localizing indexes of mScarlet-TBP-CAAX and mScarlet-TBP-SAAX. The PM localizing index reflects the degree to which a protein is localized to the plasma membrane, generally speaking, the relative proportion of localization to the plasma membrane and in the cytoplasm, which can be obtained by analyzing the fluorescence intensity. Scale: 10 μm. KMSKDGKKKKKKSKTKCVIM (SEQ ID NO:13); TGTGTAATTATGTAA (SEQ ID NO:14); AGTGTAATTATGTAA (SEQ ID NO:15).

Figure 16A:
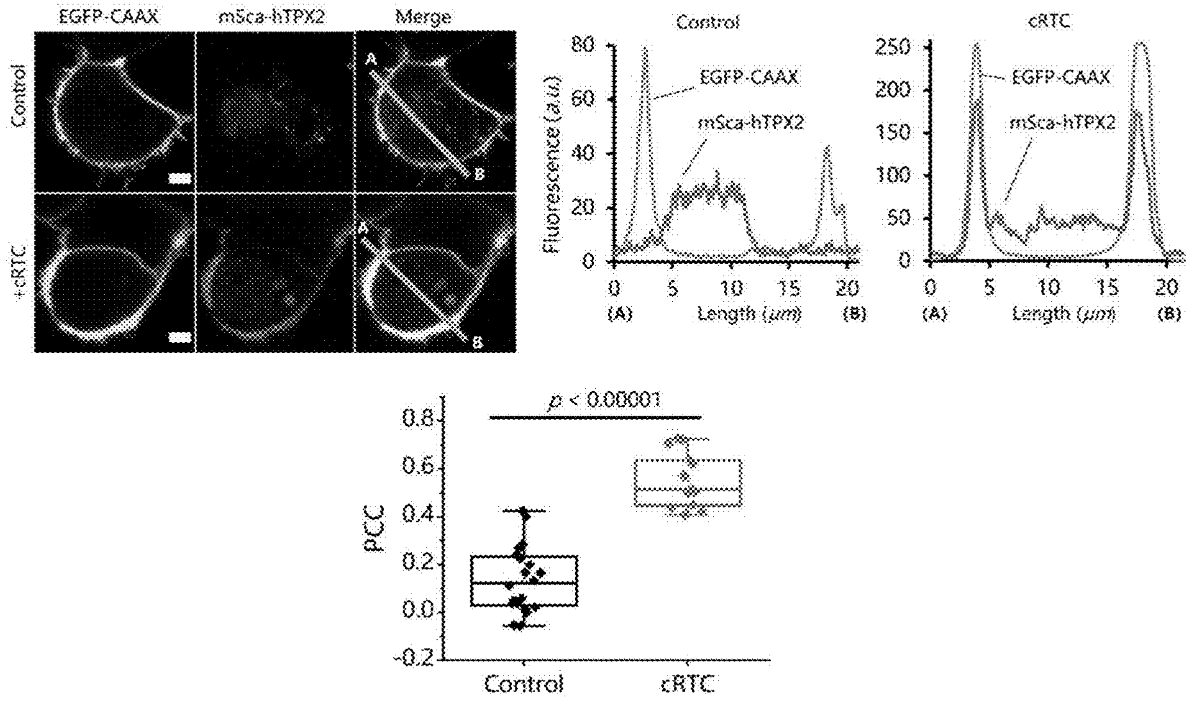

FIG. 16A shows that cRTC localizes TPX2 to the plasma membrane and inhibits cell proliferation. Living HepG2 cells co-expressing EGFP-CAAX (plasma membrane tag) and mScarlet-hTPX2 (hTPX2 tag) treated with or without cRTC (10 μM, 1.5 h) clearly showed that cRTC translocated hTPX2 to the plasma membrane. Corresponding streak analysis and PCC colocalization analysis between two fluorescence channels were performed.

Figure 16B:
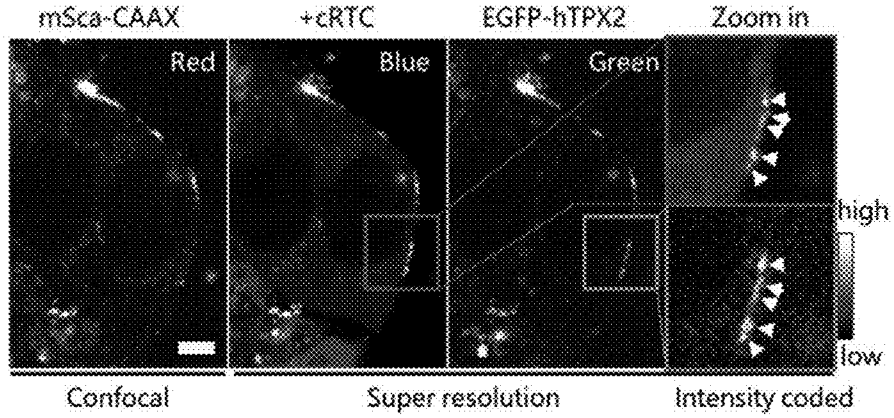

FIG. 16B shows that super-resolution fluorescence microscopy (Airyscan) shows that the cRTC inducer is clearly localized to the plasma membrane, while targeting hTPX2 to the plasma membrane and forming small droplets or condensates.

Figure 16C:
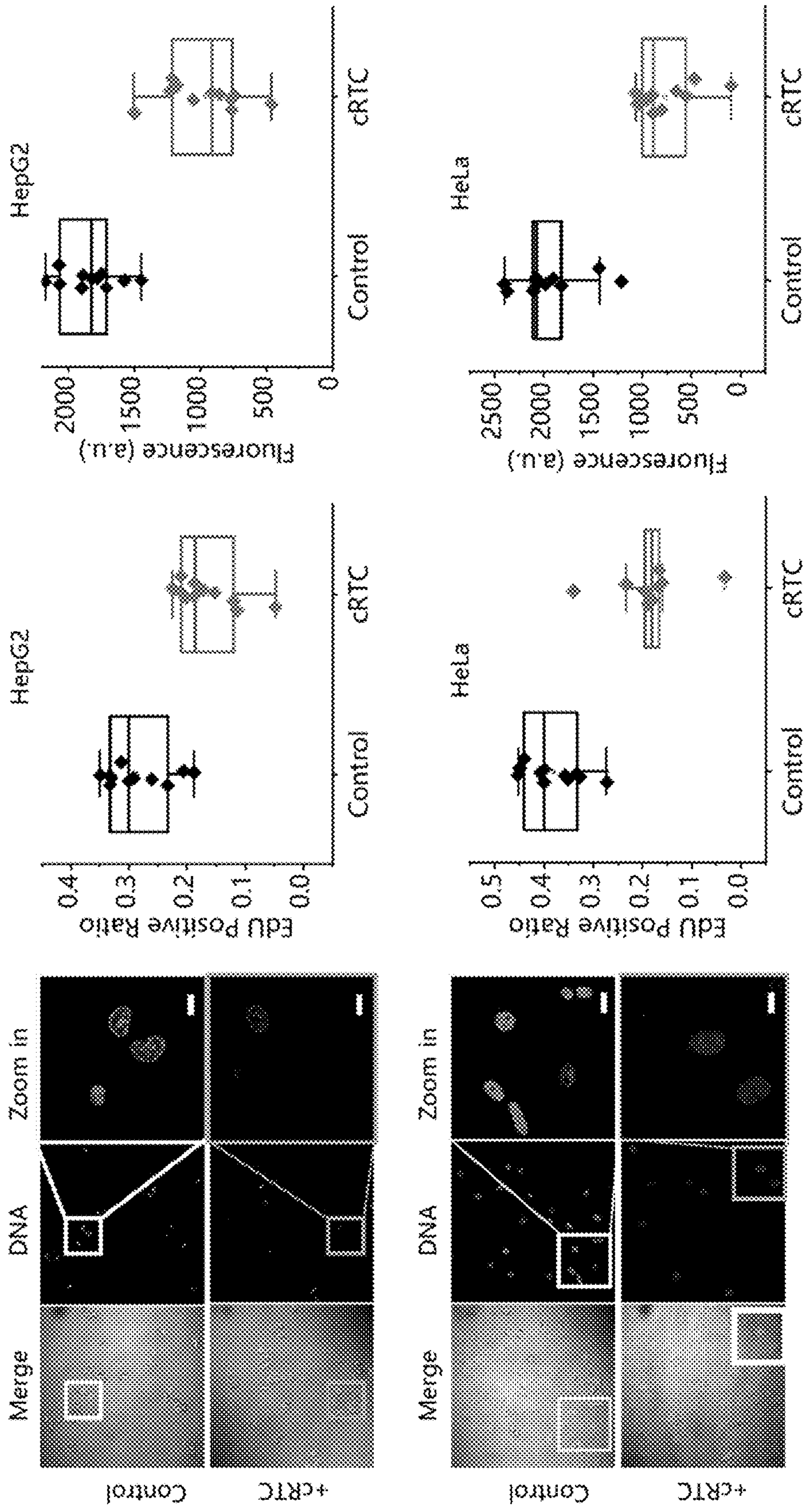

FIG. 16C shows representative confocal micrographs showing EdU cell proliferation assay results in cRTC-treated HepG2 cells (+cRTC, 10 μM, 24 h) and control HepG2 cells. The decrease in nuclear brightness of the cRTC-treated HepG2 cells and a lower ratio of EdU-positive cells compared to the control group imply a decrease in cell proliferative viability. Statistical analysis of the EdU positive ratio of HepG2 was shown; statistical analysis of nuclear fluorescence intensity of EdU-positive HepG2 cells was shown. Also, the results of the EdU cell proliferation assay of HeLa cells were shown.

Figure 16D:
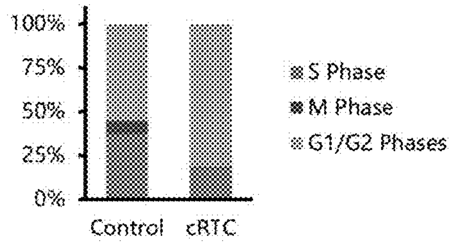

FIG. 16D shows computational comparison of the ratio of cells in each cycle of HeLa cells treated or not treated with cRTC. Yellow scale: 5 μm; white scale: 10 μm.

Figure 17A:
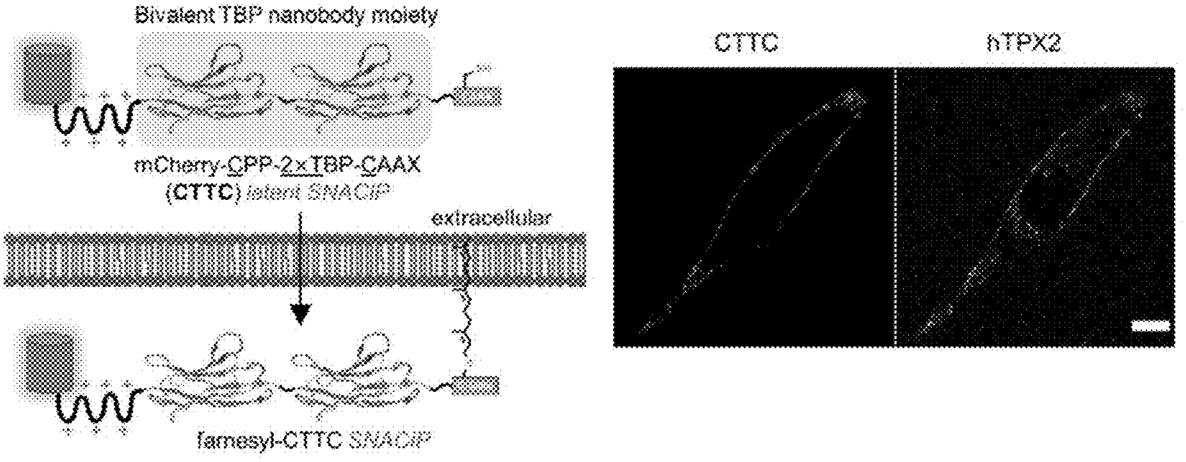

FIG. 17A shows that a bivalent SNACIP inducer CTTC can also effectively penetrate a cell and effectively inhibit cell proliferation and tumor proliferation in vivo. The structural elements of CTTC include a tandem bivalent TBP nanobody moiety, a linear Tat penetrating peptide (YGRKKRRQRRR, SEQ ID NO:11), and a C-terminal CAAX-box, wherein CTTC may also be converted into a functional SNACIP inducer of farnesyl-CTTC by prenylation after entering the cell. After HeLa cells were treated with CTTC (10 μM, 2 h, and the excess CTTC was washed off), it was found that CTTC could penetrate the cell smoothly and be localized on the plasma membrane (left), and translocate hTPX2 to the non-functional location of the plasma membrane (right).

Figure 17B:
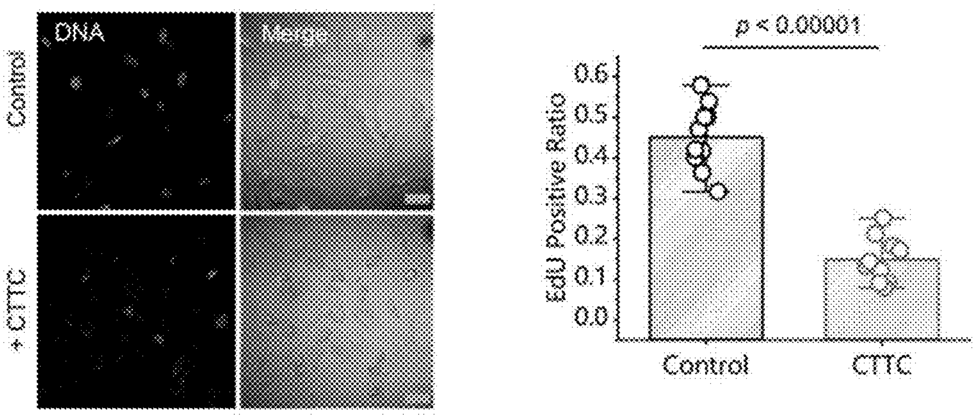

FIG. 17B shows EdU cell proliferation assay results in HeLa cells treated with 10 μM CTTC (+CTTC) and without CTTC (control). Statistical comparison of EdU positive ratio in HeLa cells treated with 10 μM CTTC (+CTTC) and without CTTC (control); error bars: standard deviation (SD, n=10).

Figure 17C:
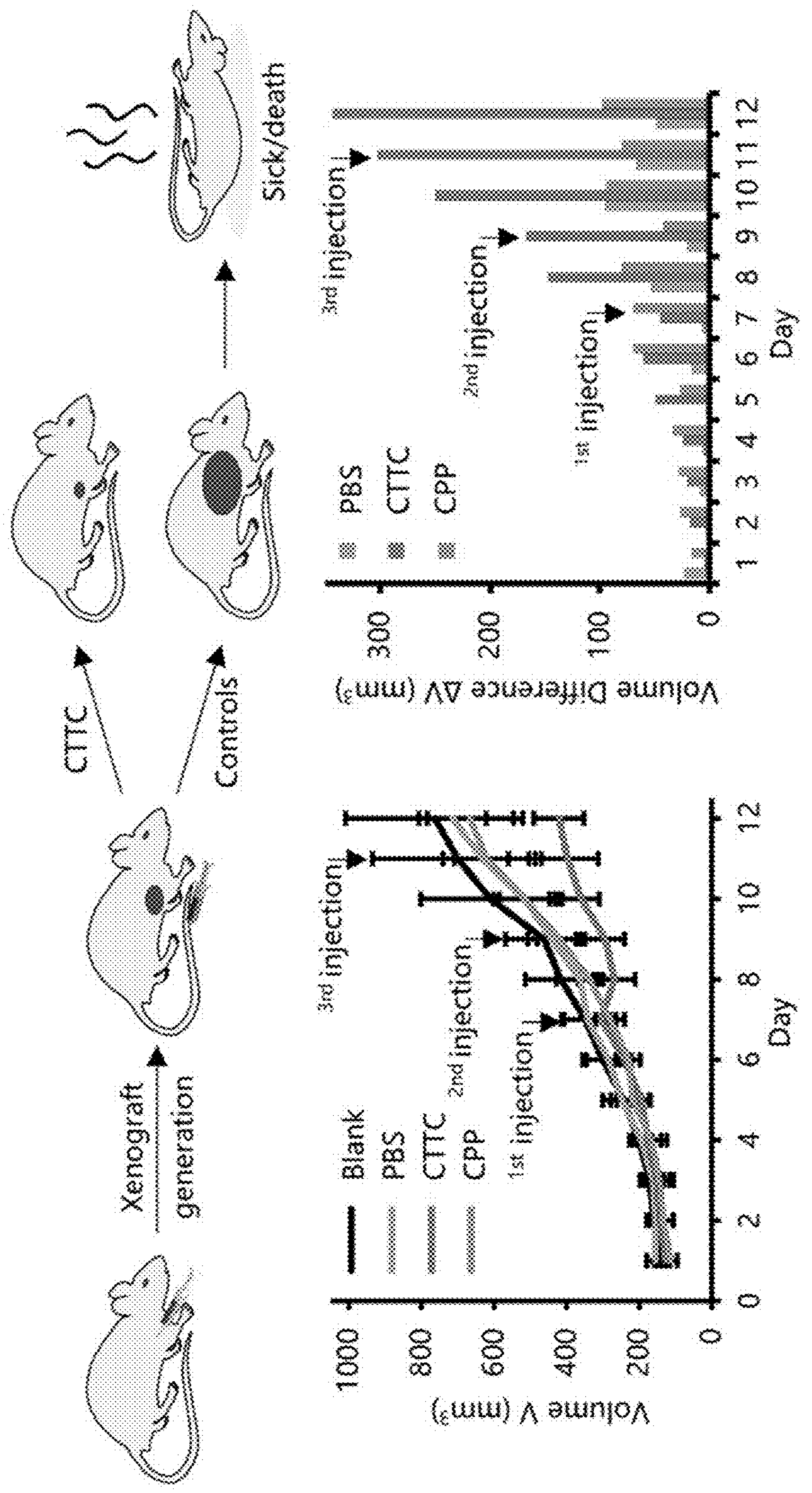

FIG. 17C shows Hepatocarcinoma xenograft mice models that were established by subcutaneously injecting an appropriate number ($5\times10^6$) of HepG2 hepatoma cells into BALB/c nude mice to evaluate the inhibitory effect of CTTC on tumor growth. When the tumors grew to 0.7-0.9 cm in diameter, CTTC was injected into mice intravenously, and the injection was performed every two days to compensate for metabolic consumption of CTTC in vivo. Daily plot of tumor volume versus time for CTTC-injected, CPP-injected, PBS-injected, and blank mice; error bars: standard error SEM. Changes of the absolute value of the difference between the mean tumor volume of mice in different groups and the mean tumor volume of mice in the blank group over time, showing that only the CTTC-injected mice have inhibited tumor growth. Scales: white, 10 μm; turquoise, 50 μm.

Figure 18:
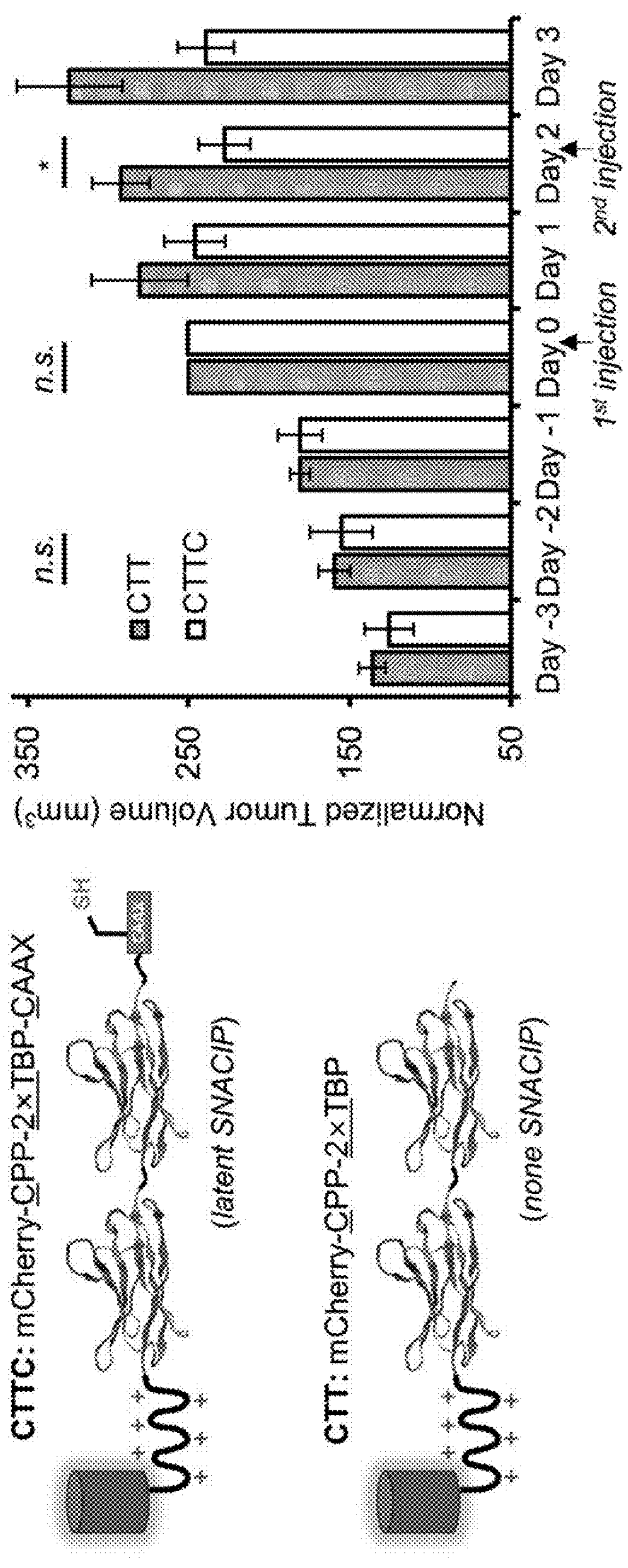

FIG. 18 shows that the CTTC inducer of proximity clearly shows a better tumor inhibitory effect than the non-SNACIP conventional bivalent nanobody chimera-CTT. A CTTC inducer contains a CAAX-box for prenylation. In contrast, a conventional bivalent nanobody-chimeric CTT does not contain a CAAX box and thus cannot be converted into a functional SNACIP inducer. Hepatocarcinoma xenograft mice models were injected with about 0.08 ml of 22 $mg\cdot ml^{-1}$ (0.35 mM) CTTC (n=6), or 20 $mg\cdot ml^{-1}$ (0.35 mM) CTT (n=7). Drug injections were performed every two days to compensate for metabolic consumption and the tumor size was recorded daily to compare the difference in the inhibitory effect of the CTTC and the CTT on tumors.

Figure 19:
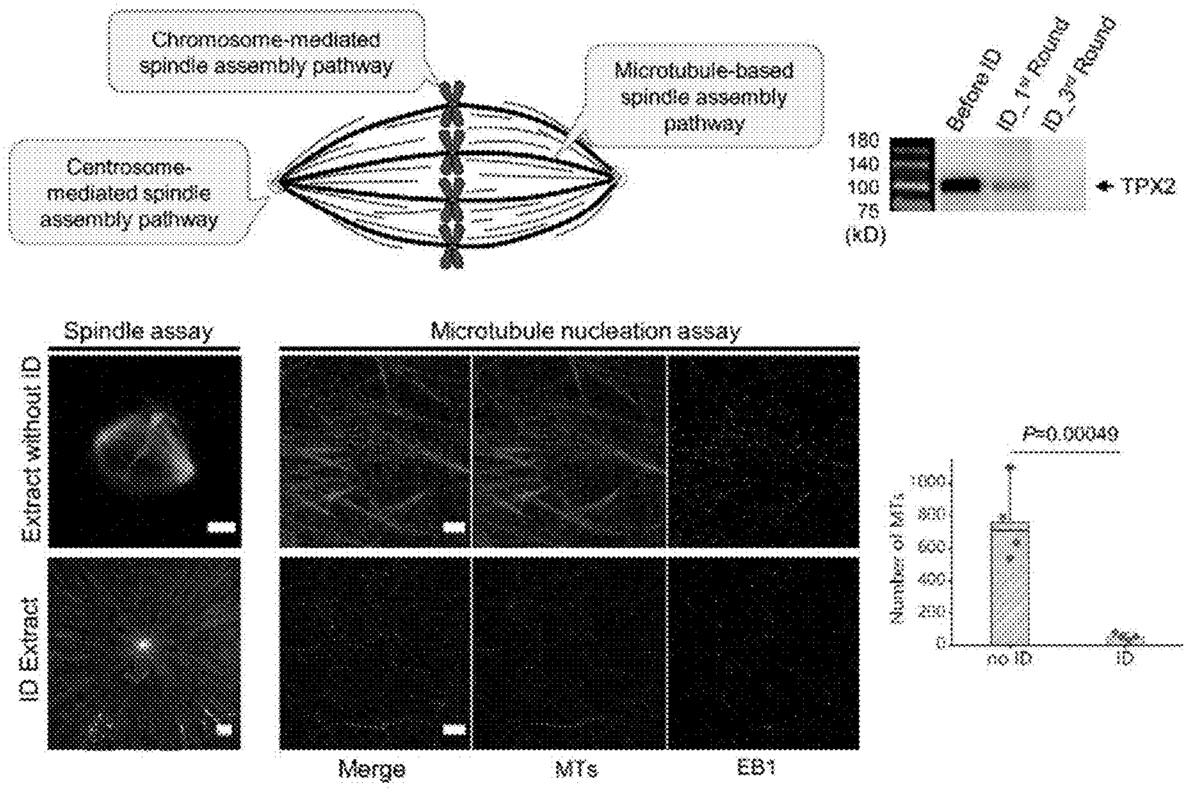

FIG. 19 shows use of a *Xenopus* oocyte cell-free system to illustrate the mechanism of how deactivation of TPX2 affects spindle assembly. Spindle assembly includes three key pathways: 1) chromosome-mediated, 2) centrosome-mediated, and 3) microtubule-based spindle assembly pathways. Each pathway involves nucleation of microtubules and exponential expansion of the number of microtubules. TPX2 antibody-coated magnetic particles were prepared for performing immunodepletion (ID) on endogenous TPX2 in a freshly prepared *Xenopus* oocyte extract. After three rounds of ID, TPX2 was completely removed as seen from Western blot (WB) results. Spindle assembly assays show that the non-ID *Xenopus* oocyte extract can support spindle formation; the TPX2-ID *Xenopus* oocyte extract cannot support bipolar spindle formation; however, the microtubule nucleation activity from the centrosome/chromosome was still largely maintained, indicating that the centrosome/chromosome-mediated microtubule nucleation pathway was not inhibited. A microtubule-based microtubule nucleation assay shows that the microtubule nucleation activity is greatly inhibited in the TPX2-ID *Xenopus* oocyte extract compared to the non-TPX2-ID *Xenopus* oocyte extract. Statistical analysis of the microtubule nucleation activity was performed. Here EB1 is a positive binding protein of microtubules, so the number of EB1 fluorescent spots may be used for quantifying the number of microtubules. Error bars: standard deviation (SD) (n=4 or 5). For the micrographs, blue: *Xenopus* sperm nuclear chromosome; green: EB1-mCherry; red: HiLyte 647-tubulin, for labeling microtubules; all scales: 10 μm.

DETAILED DESCRIPTION

Mammalian cell culture: HeLa (Cat #CL-0101) and HepG2 (Cat #CL0103) cells are purchased from Procell Life Science & Technology Co., Ltd. (Wuhan, China). The cells are identified by short tandem repeats (STR) and proved free of HIV-1, HBV, HCV, *Mycoplasma* and other microorganisms prior to culture. Other required reagents, e.g., DMEM and PBS for cell culture, also need to be confirmed free of *Mycoplasma* infection before use. Cells are cultured in 5% carbon dioxide with high glucose (4.5 $g\cdot L^{-1}$) Dulbecco's modified Eagle's complete medium (DMEM, Cat #SH30243.01 purchased from HyClone), containing 4 mM L-glutamine and 1×sodium pyruvate, supplemented with fetal bovine serum (Cat #SV30087.03 purchased from HyClone), 1% non-essential amino acids (NEAA 100×) and 1% penicillin-streptomycin (100×) premix. During cell passaging, cells are digested using EDTA-trypsin (purchased from HyClone, Cat #SH30042.01) and phosphate buffered saline (PBS) (Cat #SH30256.01, purchased from HyClone). HeLa cells are subcultured at a ratio of 1:(5-10), while HepG2 cells are subcultured at a ratio of 1:(4-6).

Animal Welfare: Mice are kept under specific pathogen-free (SPF) grade clean conditions, and are handled with the approval of the Institutional Animal Care and Use Committee of Harbin Institute of Technology (IACUC/HIT), with the license number IACUC-2021052. Mice are reared under controlled conditions of light (12 h light/12 h dark cycle), temperature (24±2 °C) and humidity (50±10%), and are fed normal chow and water ad libitum. The rearing, maintenance and oocyte collection of *Xenopus* are carried out with the approval of the IACUC/HIT, with the license number IACUC-2020020. Briefly, the feeding equipment for female (2-3 years old) and male *Xenopus* is purchased from Lingyun Boji (Beijing, China), and parameters such as water quality (deionized water, ID-$H_2O$), pH (7.2), temperature (18 °C), and conductivity (1600 μS/cm) are set as recommended by the manufacturer's manual. *Xenopus* is fed qualified *Xenopus* chow twice a week. Sperm nuclei from male *Xenopus* are prepared for spindle assays, while female *Xenopus* is induced spawning. According to the method described in CSH protocols (Shaidani et al., 2021), female *Xenopus* is injected with an appropriate amount of pregnant mare serum gonadotropin (PMSG) and human chorionic gonadotropin (hCG) in sequence, wherein PMSG promotes oocyte maturation, and hCG promotes ovulation.

Establishment and drug treatment of xenograft tumor mice model: Immunodeficient BALB/c nude mice are purchased from Liaoning Changsheng Biotechnology Co., Ltd., and female mice are injected with HepG2 cells after 4-6 weeks of age for tumorigenesis. Before injection, HepG2 cells are cultured in a standard ϕ~85 mm culture dish, and collected after entering exponential growth. The cells are first rinsed with 10 ml of PBS, then 1 ml of trypsin is added for digestion for 5-10 min to detach the cells, and then 3 ml of PBS is added for suspending the separated cells. The cell suspension is centrifuged at 1000 rpm for 8 min at 4 °C, the supernatant is removed, and the cells are resuspended in a freshly prepared mixture (v/v=1:1) of PBS/Matrigel (Solarbio, Cat #M8370). The final cell concentration is approximately 50 million cells per milliliter. For establishing the HepG2 xenograft mice model, ~5 million HepG2 cells in 0.1 ml PBS/Matrigel solution are injected subcutaneously into the axillary region of BALB/c nude mice. A stable tumor would appear within 1-2 weeks. To evaluate the effectiveness of a TPX2 nanobody conjugate, PBS (pH 7.2, containing additional 1 mM TCEP, 0.5 M NaCl and 3% glycerol) is used as blank control, and the CTTC nanobody conjugated drug is dissolved in the PBS for administration by injecting 100 μl into the mice through the tail vein. The mean tumor size [($\phi$=($\phi_L$+$\phi_S$)/2] is monitored daily using vernier calipers. The calculation formula of tumor volume is as follows: V=1/6($\pi\phi^3$).

Plasmid construction: Plasmid vectors pTXB1 (SEQ ID NO:1), pET28a(+), EGFP-C1, EGFP-N1, etc., are purchased from commercial suppliers. These vectors may be further designed and modified by, e.g., introducing $His_6$ or $His_8$ affinity tags, adding TEV or TEV" protease cleavage sites, changing restriction enzyme cleavage sites, or replacing EGFP (SEQ ID NO:4) with mTagBFP2(SEQ ID NO:7), mTurquoise 2(SEQ ID NO:3), mEYFP(SEQ ID NO:2), DsRed(SEQ ID NO:9), mScarlet (SEQ ID NO:8) or mCherry (SEQ ID NO:10) to obtain vectors expressing other fluorescent proteins for performing subsequent cloning. Regarding cloning methods, subcloning, Gibson assembly or modified Gibson assembly is employed to construct the desired plasmids. For subcloning, appropriate restriction enzymes are used for cleaving the relevant fragment directly from a vector plasmid, or perfusion high-fidelity polymerase (APExBIO, CAT #1032) is used for amplifying the corresponding gene fragment from the plasmid containing the desired gene by performing PCR, and then gel purification and restriction enzyme cleavage are performed. The obtained gene fragment is ligated into an appropriate vector with T4 DNA ligase. Cloning methods involving insertion of multiple fragments may be accomplished by stepwise subcloning or multi-fragment Gibson one-step assembly. Most genes are obtained by means of gene synthesis, and the gene exchange service is provided by Comate Bioscience Co., Ltd. (Changchun, China).

These genes include *E. coli* codon-optimized human TPX2 (i.e., codon-optimized hTPX2), *E. coli* codon-optimized GFP nanobody (GBP), mScarlet, etc. The non-codon-optimized human TPX2 gene is amplified from the plasmid pLenti-EF1a-EGFP-P2A-Puro-CMV-TPX2-3Flag, which is purchased from Obio Technology (Shanghai) Co., Ltd., Cat #H10559. Plasmids encoding human KIFSB, Rac1, Rab1b, Rab5a and other genes are purchased from the MiaoLing Plasmid Sharing Platform.

Transfection: Cells are typically seeded and transiently transfected in Thermo Scientific 8-well dishes (Cat #155409) or 4-well dishes (Cat #155382) Lab-Tek®II. DNA (0.25 μg) is dissolved in 12.5 μl of gibco opti-MEM (Cat #31985-062), and then 0.5 μl of ExFect®2000 transfection reagent (Cat #T202, Vazyme Biotech Co., Ltd., Nanjing, China) is dissolved in 12.5 μl of gibco opti-MEM. The two solutions are first incubated at room temperature for 5 min. Then, the DNA-containing opti-MEM solution is added to the ExFect®2000-containing opti-MEM solution and mixed gently. The opti-MEM containing the DNA/ExFect®2000 mixture is incubated at room temperature for 5-10 min (usually 7.5 min), and gently dropped into a 8-well dish containing 250 μl of complete DMEM, wherein the dish is seeded with 15000-20000 cells. The cells are incubated at 37 °C under 5% carbon dioxide for about 2 h to allow the cells to adhere. Then, the previous medium is replaced with fresh warm complete DMEM, and the cells are incubated at 37 °C under 5% carbon dioxide for 20 h or more. For co-transfecting multiple plasmids, the number of DNAs used in this solution refers to the total mass of plasmids.

Confocal microscopy and super-resolution imaging: 24 h after transfection, cells are imaged by confocal microscopy. With an 8-well or 4-well dish as described above, and phenol red-free DMEM medium (REF: 21063-29) containing additional 10% fetal bovine serum, 1% sodium pyruvate, 1% NEAA, 1% penicillin-streptomycin and 15 mM HEPES-Na (final pH 7.0), cells are cultured at 37 °C under 5% carbon dioxide and observed using a ZeissLSM880 inverted scanning confocal microscope. In most cases, a Zeiss Plan-APOHROMAT 100×/1.4 DIC oil immersion lens is used for microscopic imaging, and a Zeiss Plan-APOCHROMAT 60×/1.4 DIC oil immersion lens may also be used. For a larger field of view, a Zeiss PlanAPOCHROMAT40×/0.95 DICIII objective lens (as in EdU detection) is used. The obtained image is generally 12-bit in depth and 512×512 in resolution, and scanning is performed 8 times on average. 405 nm laser is used for exciting mTagBFP2, DAPI or Hoechest; 458 nm laser is used for exciting mTurquoise2; 488 nm argon laser is used for exciting EGFP or fluorescein; 514 nm argon laser is used for exciting mEYFP; HeNe 543 nm laser is used for exciting an Apollo 567 dye in EdU assays; HeNe laser 543 nm or HeNe laser 594 nm is used for exciting mScarlet-I or mCherry; and HeNe laser 647 nm is used for exciting far-infrared HiLyte647. In most cases, basic imaging setup parameters are set with the aid of the "smart setup" function. To obtain super-resolution images, an Airyscan module may be used for imaging with the ChA channel typically at 1024×1024 resolution.

Treatment of living cells with an SNACIP inducer of dimerization for microscopic imaging: Unless otherwise specified, first a DMEM complete medium of the cells is replaced with a phenol red-free imaging medium of the SNACIP inducer of dimerization of the corresponding concentration, and then imaging is performed after incubation for a given period of time. For cRGT, the concentration represents an effective ratio of cRGT; and near-complete dimerization regulation may be achieved without washing off excess cRGT before imaging. For reversible regulation with TMP, a freshly prepared phenol red-free imaging medium with a final concentration of 10 μM TMP is replaced for the previous imaging medium containing the SNACIP inducer of dimerization, and hence resulted in rapid near-complete reversible regulation, with microscopic imaging starting after 10 min.

EdU cell proliferation assay: EdU cell proliferation assay is performed using an EdU cell proliferation assay kit from RiboBio (Cat #R11053.9). Briefly, a 8-well imaging dish is seeded with $50\times10^3$ HepG2 or $20\times10^3$ HeLa cells in the exponential growth phase and the cells are allowed to grow overnight. On the next morning, a PBS solution containing a drug (e.g., cRTC) is added to each well at a final concentration of 10 μM, while the same volume of PBS solution is added to the control cell wells. On the third morning (usually 24 h later), EdU is added at a final concentration of 50 μM to all imaging wells for incubation for 2 h at 37 °C under 5% carbon dioxide. This method is suitable for general cancer cell lines. Then each well is rinsed with PBS (2×5 min) to remove excess EdU, and 100 μl of cell fixative (4% PMA in PBS) is added for incubation at room temperature (RT) for 30 min. Then 100 μl of 2 mg·ml$^{-1}$ glycine solution is added to each well and shaken for 5 min at room temperature to neutralize the fixative. The glycine solution in each well is pipetted, and each well is shaken and rinsed with 200 μl of PBS at room temperature for 5 min. The PBS is pipetted, and 200 μl of plasma membrane penetrating solution (0.5% TritonX-100 in PBS) is added to each well and shaken at room temperature for 10 min. The fixed cells are washed again with PBS (1×5 min) before the assay. Before fluorescent labeling is performed by a click reaction, a freshly prepared 1×Apollo labeling solution containing a red Apollo567 dye (Cat #C10310-1), a catalyst and other necessary reagents need to be prepared according to reagent instructions. For example, 1 ml of 1×Apollo labeling solution may be prepared by sequentially mixing and adding 938

μl of DI—$H_2O$, 50 μl of Apollo reaction buffer (reagent B), 10 μl of Apollo catalyst solution (containing $Cu^{2+}$, buffer C), 3 μl of Apollo567 dye (reagent D) and ~9 mg of Apollo supplement (ascorbate sodium salt, reagent E). 200 μl of freshly prepared 1×Apollo labeling solution is added to each well, and shaken for 30 min at room temperature in the dark to complete labeling. The labeling solution is removed, and the cells in each well are washed again with the plasma membrane penetrating solution (0.5% TritonX-100PBS) (3×10 min). The osmotic solution is pipetted and the cells are washed with PBS (1×5 min). Finally, fresh PBS is added, and the labeled cells can be imaged by fluorescence confocal microscopy.

Isothermal titration calorimetry (ITC): ITC measurements are performed using a MicroCal ITC200 device from GE Malvern. TPX2 nanobody and hTPX2 protein are dissolved in freshly prepared PBS (pH 7.2, containing additionally added 1 mM TCEP, 0.5 M NaCl and 3% glycerol). 21 μl of hTPX2 solution is added to a sample pool, and 51 μM of TPX2C nanobody is pipetted by a syringe and injected 2.0 μl×18 times into the sample pool at an interval of 3 min (except for the first injection of 0.8 μl of nanobody at an interval of 2.5 min). The titration data is processed using Origin software, and parameters such as $K_d$ and binding stoichiometric values are calculated.

Fröster resonance energy transfer (FRET) measurement (measurement method in FIG. 31): Since the emission spectra of EGFP and mCherry or mScarlet overlap with the absorption spectra, EGFP and mCherry or mScarlet form a FRET pair. To measure FRET, a SpectraMax i3x spectrometer from Molecular Device (MD) equipped with a 96-well plate is used. Appropriate volumes (100 μl or 200 μl) of donor and acceptor fluorescent molecules are added to the sample wells in the 96-well plate. Unless otherwise specified, the excitation wavelength is 470 nm, and the emission spectral range is 490-750 nm.

Immunodepletion (ID) (research mechanism, FIG. 17): In a typical ID assay, 32 μl of protein A/G magnetic particles (IP grade) (YEASEN, Cat #36417ES03) are coupled and coated with xTPX2 polyclonal antibody (~23 μg) according to a flow provided by the manufacturer. The xTPX2 polyclonal antibody used in the assay is obtained by immunizing rabbits with a C-terminal fragment of xTPX2 protein, purifying by protein A, and then affinity purifying with antigen. Antibody-coupled magnetic particles are suspended in 32 μl of CSF-XB buffer and divided into three equal aliquots. The CSF-XB buffer is removed from each aliquot of the magnetic particles prior to addition of a *Xenopus* oocyte extract. Then 30 μl of freshly prepared *Xenopus* oocyte extract is mixed with an aliquot of the magnetic particles, and the magnetic particles are resuspended by gentle pipetting. The suspension is incubated on ice for about 10-15 min, and then the magnetic particles are recovered within 5-10 min using a magnetic particle concentrator (MPC) to obtain the *Xenopus* oocyte extract immunodepleted for the first round. The immunodepletion is repeated two more times to completely deplete the xTPX2 in the extract. Western blot essays using the same ID antibody may be used for confirming complete elimination of xTPX2.

Spindle assembly assay and microtubule nucleation assay performed in *Xenopus* oocyte extract (research mechanism, assays in FIG. 17): The *Xenopus* oocyte extract is prepared according to a commonly used extraction procedure (Hannak & Head, Nat. Protoc., 2006, 1, 2305) using freshly excreted *Xenopus* oocytes at an ambient temperature of 18 °C. A 10 mg·ml$^{-1}$ LPC (leupeptin, pepstatin, and chymostatin, each at a final concentration of 20 μg·ml$^{-1}$) protease inhibitor and 10 mg·ml$^{-1}$ cytochalasin D (at a final concentration of 20 μg·ml$^{-1}$) are added to a freshly prepared *Xenopus* oocyte extract without addition of an energy mix. Then, the *Xenopus* oocyte extract is placed on ice immediately until use. Immunodepletion, spindle assays or microtubule nucleation assays should also be performed immediately after the *Xenopus* oocyte extract is prepared. Sperm nuclear chromosomes from male *Xenopus* are prepared according to CSH protocols (Hazel & Gatlin, 2018). For the spindle assays, 0.25 μl of sperm nuclei, 0.33 μl of 2 mg·ml$^{-1}$ HiLyte647 porcine brain tubulin (Cytoskeleton, Cat #TL670M-A/B), 0.25 μl of 5 mg·ml$^{-1}$ EB1-mCherry, and 0.25 μl of 100 μg·ml$^{-1}$ DAPI are added to 8 μl of the extract. The *Xenopus* oocyte extract mixture is mixed gently and loaded into a self-made glass slide with a sample channel. The extract mixture is incubated at 18 °C. After 30 min, the spindle structure should appear, which can be observed with a high-end confocal laser scanning microscope. For the microtubule nucleation assays, 0.3 μl of EB1/vanadate premix (EB1-mCherry, 1 mg·ml$^{-1}$, 10 mM sodium vanadate) and 0.33 μl of 2 mg·ml$^{-1}$ HiLyte647 porcine brain tubulin are added to 8 μl of the extract, mixed gently, and immediately loaded into a self-made glass slide with a sample channel. The extract is incubated at 18 °C. As microtubules gradually appear, the nucleation process is observed with a confocal laser scanning microscope.

Design and preparation of cyclic cell-penetrating peptide Cys-cR10*: The cyclic peptide Cys-cR10* is characterized by a cyclic rR ring (r=D-Arg, R=L-Arg), a $(Gly)_5$ linker, a free N-terminal cysteine and a C-terminal containing a —$CONH_2$ group. Solid phase peptide synthesis (SPPS) is performed with Rink amide resin. After an R10 fragment is synthesized, intramolecular cyclization is performed, and a ring is formed by condensing a lysine side chain (—$NH_2$ group) and glutamic acid (—COOH group) to form an intramolecular amide bond. Cys-$(Gly)_5$ moieties are then sequentially added to the cyclic r10 moiety, and Cys-cR10* is finally deprotected and purified. The Cys-cR10* cyclic peptide is 98.8% pure and its structure is identified by mass spectrometry. $C_{84}H_{160}N_{50}O_{19}S$, exact molecular weight: 2205.28; molar mass M.W.: 2206.56; measured mass-to-charge ratio m/z: 736.4$[M+3H]^{3+}$, 552.6$[M+4H]^{4+}$, 442.3 $[M+5H]^{5+}$.

Universal expressed protein ligation (EPL) method: A protein for EPL is expressed as a fusion chimera with a pTXB1 plasmid, the C-terminal end of the chimera will contain MxeGyrA intein, and the gene for expressing the protein will be cloned into the pTXB1 vector. Then, the fusion-expressed chimera is purified and exchanged into buffer A (PBS (pH 8.0), 0.5 M sodium chloride, 3% of glycerol), and the concentration is adjusted to 8.5 mg·L$^{-1}$. At the start of the ligation reaction, ¼ volume of sodium 2-mercaptoethanesulfonate (MENSNa, 2M) stock (pH 8.0) is added as a proteolytic cleavage reagent, and ¼ volume of 4-mercaptoacetic acid (MPAA, 1.1 M) stock (pH 8.0) is added as a catalyst to speed up the ligation. Finally, a small molecule reagent containing N-terminal cysteine is added to the reaction solution at a concentration of 0.5-1 mM. The reaction mixture is incubated on ice for several days, and the ligation process is monitored by SDS-PAGE. Generally, most proteins are converted to ligation products after 2-4 days of incubation. The ligation products may be further purified by a step gradient (0-500 mM imidazole) gravity column using high affinity nickel resin FF (GenScript, Cat #). If necessary, non-ligated products containing CBD-fusions may be further removed using chitin resin (NEB, Cat #S6651L).

General steps for protein expression and purification: pET28a(+) or genetically engineered pET28a (+) vectors, e.g., pET28b (TEV), may be used as vectors for expression of most proteins, and pTXB1 vectors are used for expressing GFP nanobody fused to an intein-chitin binding domain (intein-CBD) tag for a subsequent expressed protein ligation (EPL) reaction. The protein-expressing plasmids are first transformed with *E. coli* Rosetta2a competent cells, and then screened on an ampicillin (100 mg·$L^{-1}$) or kanamycin (50 mg·$L^{-1}$) agarose plate according to the resistance of the plasmids. 50-100 mL of LB medium containing the corresponding 100 mg·$L^{-1}$ ampicillin or 50 mg·$L^{-1}$ kanamycin is inoculated with a single colony. First the cells are pre-cultured at 37 °C with shaking at 240 rpm for 8-12 h or overnight. Then ~1.8 L of fresh LB medium containing 100 mg·$L^{-1}$ ampicillin or 50 mg·$L^{-1}$ kanamycin is inoculated with 30-50 mL of the pre-cultured bacterial solution, and additional chloramphenicol (33 mg·$L^{-1}$) is added. The competent cells in the LB medium are shaken at 180 rpm at 37 °C for several hours (usually 2-3 h) until the OD600 (absorbance at 600 nm) is 0.05-0.1. Then 0.5 ml of 1 M IPTG solution (final 0.27 mM) is added to induce protein expression at 37 °C for 3-5 h, or at 16 °C overnight. Sometimes, the expression time and temperature of the protein need to be optimized through assays to achieve a more ideal protein expression level.

Subsequently, cells are collected by centrifugation (8000 rpm, 4 °C, 15 min) and washed once with PBS (4700 rpm, 10 min). Bacterial pellets are resuspended in a lysis buffer (PBS (pH 8.0), containing additional 0.5 M sodium chloride, 3% glycerol, 3 mM BEM added as appropriate, and 1 mM PMSF). A small volume of bacterial cell suspensions (<40 ml) is usually lysed on ice with 80 W sonication for 30 min or 60 W sonication for 45 min (1 s sonication followed by a 3 s interval). For batch treatment or a large volume of cell suspension, cells are usually lysed using an ultra-high pressure homogenizer at 4 °C at 800-900 bar for 2-3 cycles, wherein the ultra-high pressure homogenizer needs to be equipped with a desktop circulating condensate machine for providing condensate water. The obtained lysate is centrifuged at high speed (25000 rpm, 45 min, 4 °C), and the obtained supernatant is purified by a gravity Ni-NTA column (2-5 ml resin filler). The labeled protein is washed and then eluted with a gradient of imidazole (50, 100, . . . , up to 500 mM). In addition, gradient elution (0→500 mM imidazole) may also be performed using GE's AKTAPure equipped with a HisTrapFF column, e.g., gradient elution is achieved using a buffer A (PBS (pH 8.0), containing additional 0.5 M NaCl, 3% glycerol, and 3 mM BEM added as appropriate) combined with a buffer B (solution A with the same pH, containing additional 0.5 M imidazole dissolved). If the protein purified according to this procedure requires further purification, ion exchange or size exclusion chromatography may be applied. The obtained protein typically needs to be concentrated, exchanged with buffer A, aliquoted, quickly frozen in liquid nitrogen, and stored at 80 °C.

Synthesis and characterization of key small molecule compounds: A $^{1}$H-NMR or $^{13}$C-NMR nuclear magnetic spectrum is obtained by a 400 MHz or 600 MHz Bruker BioSpin GmbH magnetic resonance spectrometer. The relevant parameters of the $^{1}$H-NMR spectrum are as follows: chemical shift S is expressed in parts per million (ppm); multiplicities are expressed as follows: s (singlet), d (doublet), t (triplet), q (quartet), dd (doublet of doublets), m (multiplet), or br (broadened); coupling constants J are expressed in Hertz (Hertz or Hz); the integral (n) of the hydrogen spectrum is expressed in nH. High resolution mass spectra (HR-MS) are obtained using an Agilent 6540 Q-TOF mass spectrometer by electrospray ionization (ESI).

Reaction Scheme 1 | Synthetic route of Cys-TMP (1)
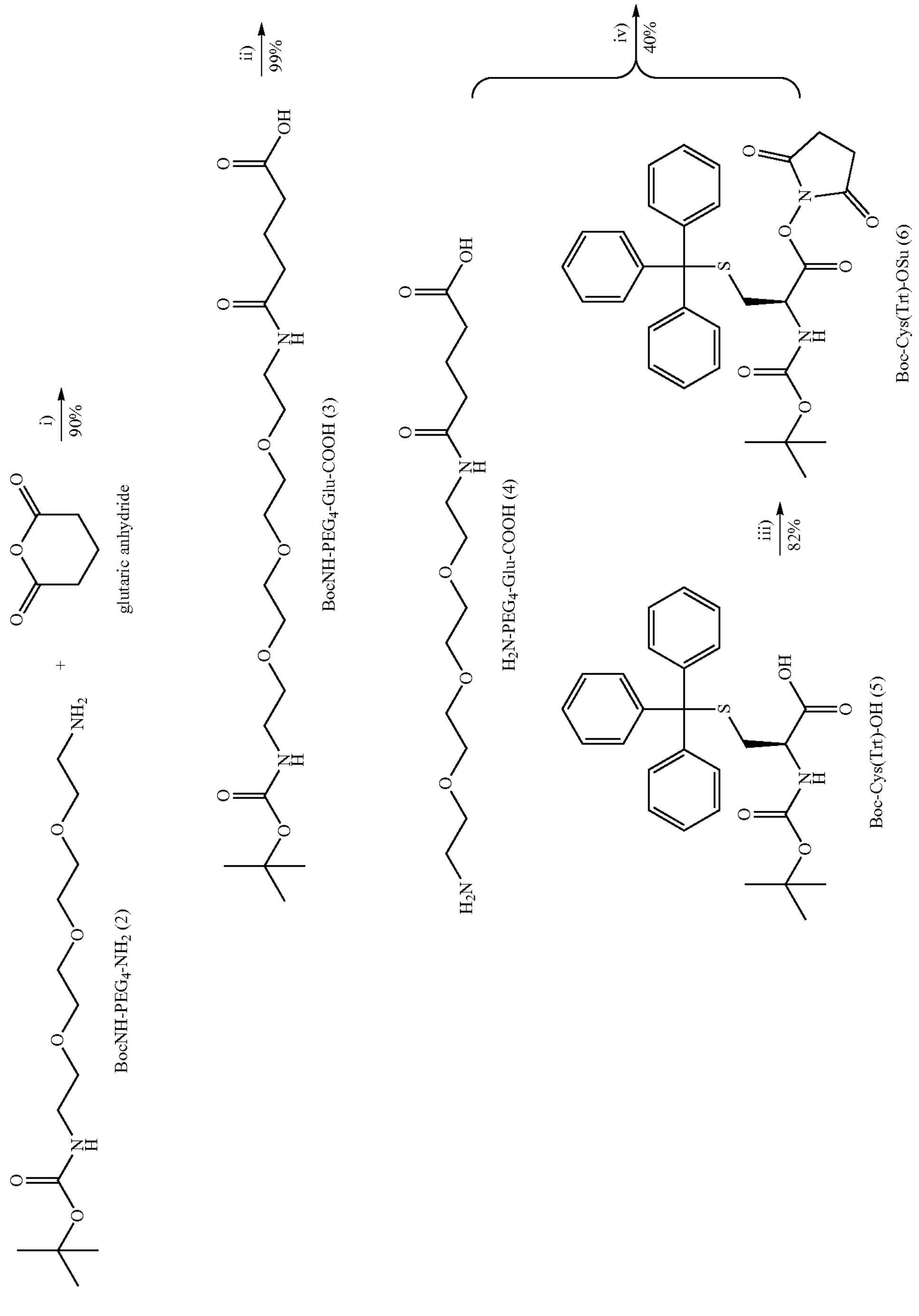
BocNH-PEG$_4$-NH$_2$ (2)
glutaric anhydride
BocNH-PEG$_4$-Glu-COOH (3)
H$_2$N-PEG$_4$-Glu-COOH (4)
Boc-Cys(Trt)-OH (5)
Boc-Cys(Trt)-OSu (6)

-continued
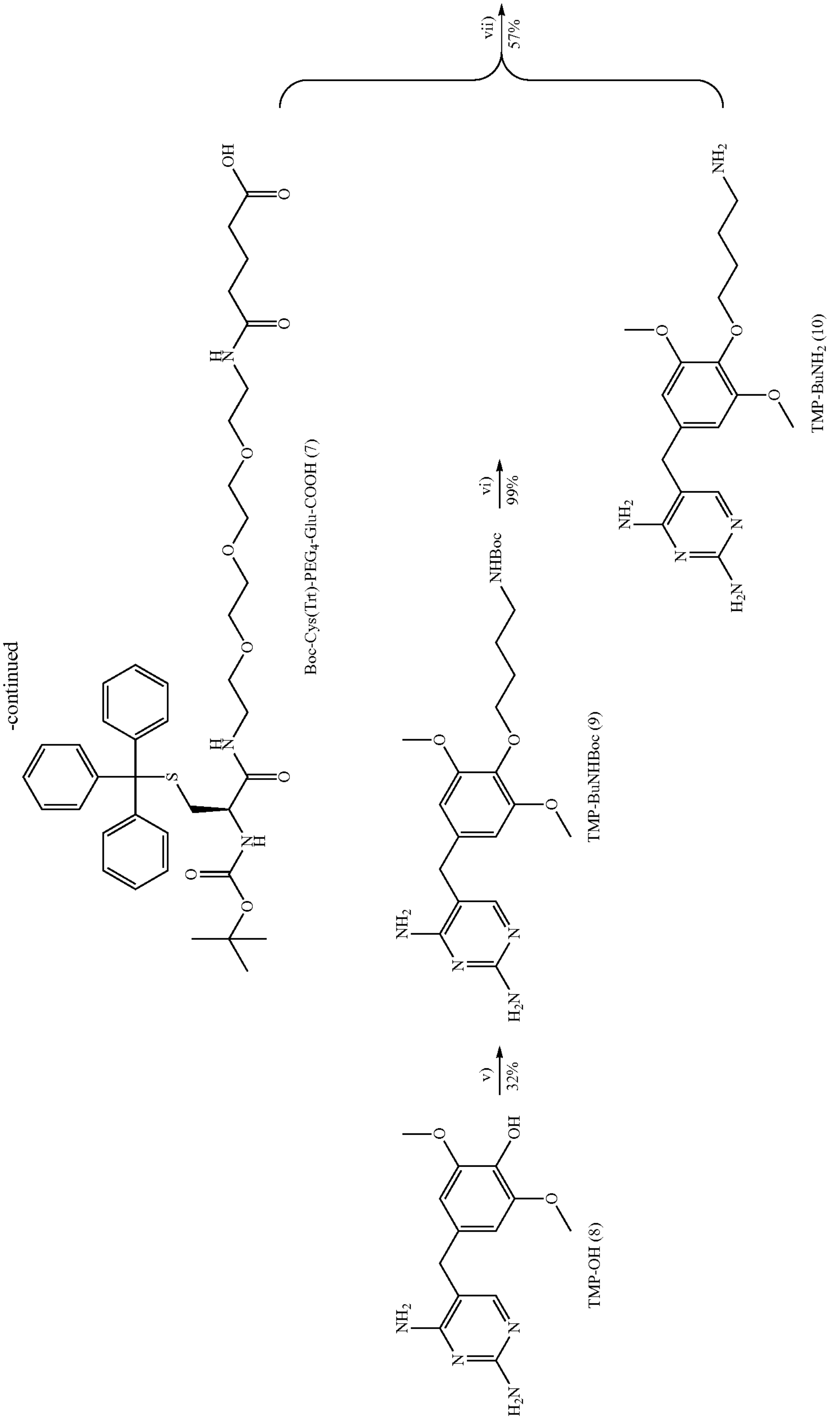
Boc-Cys(Trt)-PEG$_4$-Glu-COOH (7)
TMP-OH (8)
TMP-BuNHBoc (9)
TMP-BuNH$_2$ (10)

-continued

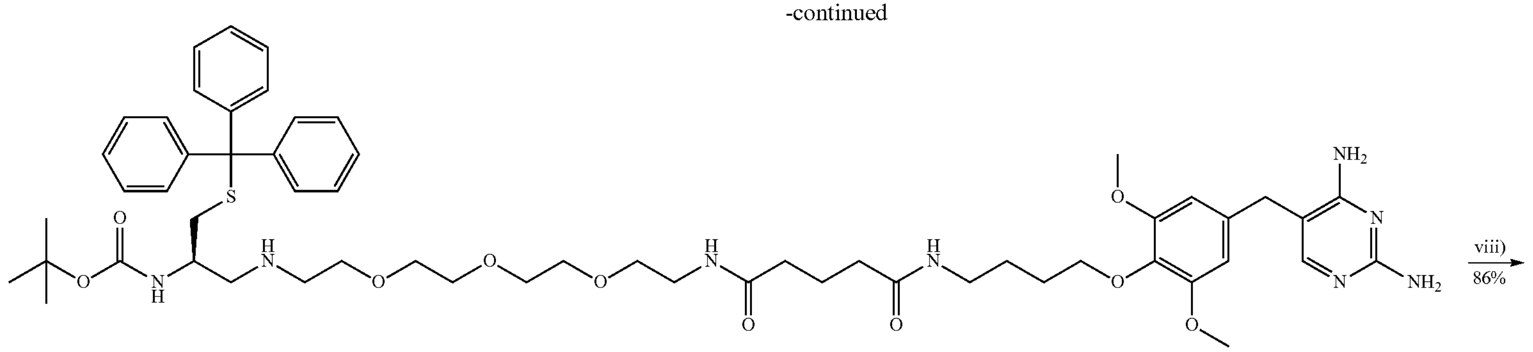

Boc-Cys(Trt)-TMP (11)

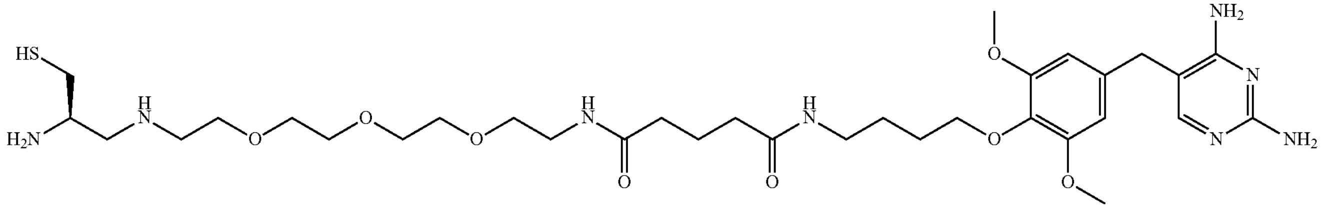

CysTMP (1)

i) DIEA, THF, RT, ON, 90%; ii) TFA, DCM, RT, 30 min, 99%; iii) HBTU, NHS, DIEA, DCM, 2 h, 82%; iv) DIEA, THF, RT, ON, 40%; v) tert-butyl 4-bromobutylcarbamate, $Cs_2CO_3$, NaI•$2H_2O$, DMF, RT, 20 h, 32%; vi) TFA/DCM (1:2), RT, 30 min, then aq. $Na_2CO_3$, 99%; vii) HATU, DIEA, DCM, RT, ON, 57%; viii) TFA, 2.5% w TIS, RT, 1 h, 86%. Abbreviations: TMP, trimethoprim; DIEA, N,N-diisopropylethylamine; THF, tetrahydrofuran; RT, room temperature; ON, overnight; TFA, trifluoroacetic acid; DCM, dichloromethane; HBTU, 2-(1H-Benzotriazole-1-yl)-1,1,3,3-tetramethyluronium hexafluorophosphate; NHS, N-hydroxysuccinimide; DMF, N,N-dimethylformamide; HATU, 1-[bis(dimethylamino)methylene]-1H-1,2,3-triazolo(4,5-b)pyridinium3-oxide hexafluorophosphate; TIS, triisopropylsilane.

Synthesis of CysTMP(1) and Related Intermediates

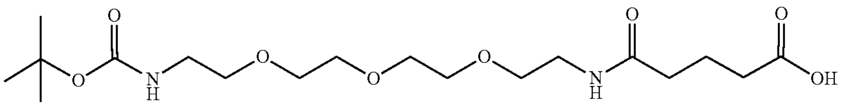 [SMILES: CC(C)(C)OC(=O)NCCOCCOCCOCCNC(=O)CCCC(=O)O]

5-(2-(2-(2-(2-(tert-butoxycarbonyl)ethoxy)ethoxy)ethoxy)ethylamino)-5-oxopentanoic acid (BocNH-PEG$_4$-Glu-COOH, 3). BocNH-PEG$_4$-NH$_2$ (1.2 g, 4.11 mmol), and glutaric anhydride (468 mg, 4.11 mmol) are dissolved in anhydrous tetrahydrofuran (THF) (21 ml), and then DIEA (636 mg, 4.93 mmol) is added. The reaction is performed under stirring at room temperature overnight. The reaction solution is aliquoted into EtOAc/aq. $NaH_2PO_4$ (2 M), then the organic layers are separated and the aqueous layer is extracted twice with ethyl acetate (EtOAc). All organic layers are mixed, washed once with saturated brine, dried over anhydrous $Na_2SO_4$, filtered, concentrated under reduced pressure, and subjected to silica gel column chromatography (EtOAc/MeOH 8/1, Rf 0.4-0.6 (tailing), followed by EtOAc/MeOH 5/1) to obtain 1.5 g of product with a yield of 90%. $^1$H-NMR ($CDCl_3$, 400 MHz): δ 6.51 (s, 1H), 5.16 (s, 1H), 3.63 (br, 8H), 3.53 (m, 4H), 3.44 (m, 2H), 3.29 (br, 2H), 2.37 (t, J=6.8 Hz, 2H), 2.28 (t, J=7.4 Hz, 2H), 1.94 (m, 2H), 1.42 (s, 9H); $^{13}$C-NMR ($CDCl_3$, 101 MHz): δ 176.00, 172.91, 156.30, 79.53, 77.36, 70.61, 70.50, 70.29, 69.95, 40.41, 39.33, 35.32, 32.92, 28.51; HRMS: $C_{18}H_{35}N_2O_8^+$ [M+H]$^+$ calc. 407.2393, found 407.2393.

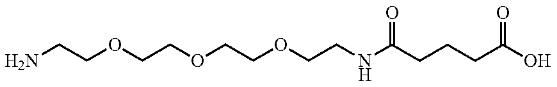 [SMILES: NCCOCCOCCOCCNC(=O)CCCC(=O)O]

5-(2-(2-(2-(2-aminoethoxy)ethoxy)ethoxy)ethylamino)-5-oxopentanoic acid (H$_2$N-PEG$_4$-Glu-COOH, 4). BocNH-PEG$_4$-Glu-COOH (406 mg, 1 mmol) is dissolved in anhydrous dichloromethane (DCM) (2 ml), then trifluoroacetic acid (1 ml) is added, and the reaction is performed under stirring at room temperature for 30 min for deprotection. DCM, TFA and other volatile components are removed under high vacuum to obtain ~423 mg of the deprotected product nTFA·H$_2$N-PEG$_4$-Glu-COOH (~1 mmol) with an almost quantitative yield. $^1$H-NMR ($CDCl_3$, 400 MHz): δ7.94 (br, 1H), 7.90 (br, 1H), 4.66 (br, 3H), 3.79 (m, 2H), 3.70 (m, 2H), 3.62 (m, 6H), 3.56 (m, 2H), 3.43 (br, 2H), 3.21 (br, 2H), 2.37 (m, 2H), 2.29 (m, 2H), 1.93 (m, 2H); $^{13}$C-NMR ($CDCl_3$, 101 MHz): δ 176.88, 174.36, 77.36, 70.33, 70.22, 69.96, 69.89, 69.75, 39.94, 39.48, 35.12, 33.09, 20.98; HRMS: $C_{13}H_{27}N_2O_6^+$ [M+H]$^+$ calc. 307.1869, found 307.1868.

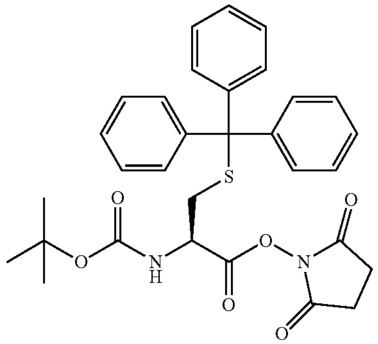 [SMILES: CC(C)(C)OC(=O)N[C@@H](CSC(c1ccccc1)(c1ccccc1)c1ccccc1)C(=O)ON1C(=O)CCC1=O]

(R)-2-(tert-butoxycarbonyl)-3-(tritylthio)propanoic acid N-hydroxysuccinimidyl ester (BocCys(Trt)-OSu, 6). Boc-Cys(Trt)-OH (464 mg, 1 mmol) and HBTU (417 mg, 1.1 mmol) are dissolved in anhydrous dichloromethane (DCM) (10 ml) and stirred at RT for 10 min. Then weak base DIEA (206 mg, 1.6 mmol) is added and the reaction is continued under stirring for 10 min. Finally, N-hydroxysuccinimide (NHS) (127 mg, 1.1 mmol) is added, and the reaction is continued for about 2-3 h. Thin layer chromatography (TLC) (cyclohexane/EtOAc 2/1, Rf 0.4) shows that the reaction is complete. The reaction solution is aliquoted in EtOAc/aq. $NaH_2PO_4$ (2M), then the organic layers are separated and the aqueous layer is extracted once with ethyl acetate EtOAc. All organic layers are mixed, washed once with saturated brine, dried over anhydrous sodium sulfate, filtered, concentrated under reduced pressure, and dried in vacuum to obtain an NHS ester product. Gradient silica gel column chromatography (cyclohexane→cyclohexane/EtOAc 4/1, 3/1, up to 2/1) is performed to obtain 459 mg of a white foamy solid as the final product with a yield of 82%. $^1$H-NMR (DMSO-d$^6$, 400 MHz): δ 7.67 (d, J=8.32 Hz, 1H), 7.33 (m, 12H), 7.26 (m, 3H), 3.91 (m, 1H), 3.32 (s, 2H), 2.75 (s, 4H), 1.38 (s, 9H); $^{13}$C-NMR (DMSO-d$^6$, 101 MHz): δ 169.60, 167.00, 154.83, 143.94, 129.00, 128.15, 126.89, 78.93, 66.71, 51.67, 32.28, 28.03, 25.37; HRMS: $C_{31}H_{33}N_2O_6S^+$ [M+H]$^+$ calc. 561.2059, found 561.2057.

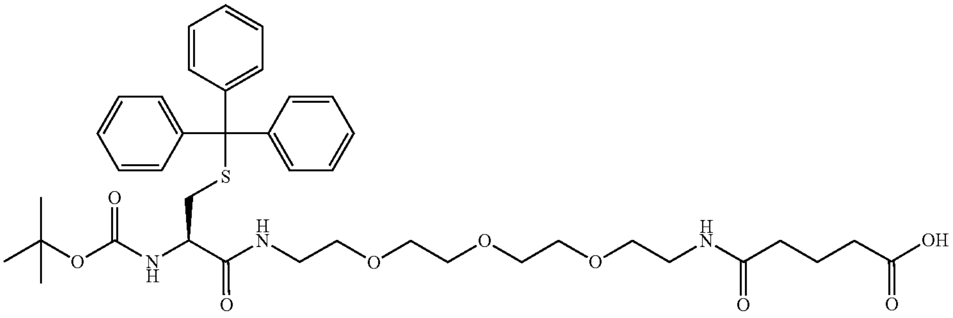 [SMILES: CC(C)(C)OC(=O)N[C@@H](CSC(c1ccccc1)(c1ccccc1)c1ccccc1)C(=O)NCCOCCOCCOCCNC(=O)CCCC(=O)O]

(R)-5-(2-(2-(2-(2-(2-(tert-butoxycarbonyl)-3-(tritylthio) propanamido)ethoxy)ethoxy)ethoxy) ethylamino)-5-oxo-pentanoic acid (BocCys(Trt)-$PEG_4$-Glu-COOH, 7). BocCys (Trt)-OSu (440 mg, 0.78 mmol) is dissolved in THE (4.5 ml), which is then added dropwise to a stirred solution of nTFA·$H_2$N-$PEG_4$-Glu-COOH (423 mg, ~1 mmol) and DIEA (387 mg, 3 mmol) in basic THE (3.5 ml). The reaction is performed under stirring at room temperature for 8 h. Then the reaction solution is aliquoted into EtOAc/aq. $NaH_2PO_4$ (2 M). The organic layers are separated and the aqueous layer is extracted twice with ethyl acetate (EtOAc). All organic layers are mixed and washed four times with 2 M aq. $NaH_2PO_4$ to substantially remove NHS by-products and excess $H_2$N-$PEG_4$-Glu-COOH starting material. The organic layers are washed once with saturated brine, dried over anhydrous sodium sulfate, filtered, concentrated, and subjected to gradient silica gel column chromatography (EtOAc→EtOAc/MeOH 20/1, finally EtOAc/MeOH 15/1) to obtain 235 mg of a white foamy solid as the product with the yield of 40%. $^1$H-NMR (DMSO-$d^6$, 400 MHz): δ 12.00 (s, br, 1H), 7.84 (t, J=5.76 Hz, 1H), 7.74 (t, J=5.40 Hz, 1H), 7.36-7.20 (m, 15H), 6.87 (d, J=8.36 Hz, 1H); 3.91 (m, 1H), 3.48 (m, 10H), 3.38 (t, J=5.92 Hz, 2H), 3.17 (m, 4H), 2.32 (d, J=7.08 Hz, 2H), 2.19 (t, J=7.44 Hz, 2H), 2.09 (t, J=7.44 Hz, 2H), 1.69 (m, 2H), 1.37 (s, 9H); $^{13}$C-NMR (DMSO-$d^6$, 101 MHz): δ 174.16, 171.70, 170.08, 144.32, 129.08, 128.02, 126.75, 78.37, 69.71, 69.60, 69.53, 69.10, 68.86, 65.86, 53.39, 38.44, 34.37, 32.99, 28.11, 20.67; HRMS: $C_{40}H_{54}N_3O_9S^+$ [M+H]$^+$ calc. 752.3581, found 752.3582.

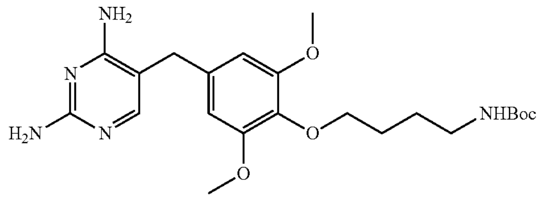 [SMILES: COc1cc(Cc2cnc(N)nc2N)cc(OC)c1OCCCCNC(=O)OC(C)(C)C]

tert-butyl4-(4-((2,4-diaminopyrimidin-5-yl)methyl)-2,6-dimethoxyphenoxy)butylcarbamate (TMP-Bu-NHBoc, 9). Dimethoprim, i.e. TMP-OH (8), may be obtained by demethylating trimethoprim (TMP), ref. (Chen et al., Chem. Commun. 2015, 51, 16537). Then TMP-OH (1.1 g, 4 mmol), 4-Boc-1-bromobutylamine (1.06 g, 4.2 mmol), $Cs_2CO_3$ (2.74 g, 8.4 mmol) and NaI·$2H_2O$ (0.6 g, 4 mmol) are suspended/dissolved in anhydrous DMF (20 ml). The reaction solution is stirred at room temperature for 20 h in the presence of argon. The reaction solution is aliquoted into EtOAc/$H_2O$. After the organic layers are separated, the aqueous layer is extracted three times with ethyl acetate. All organic layers are mixed, washed with saturated brine, dried over anhydrous sodium sulfate, filtered, concentrated, and subjected to gradient silica gel column chromatography (EtOAc→$CHCl_3$→$CHCl_3$/MeOH 10/1)) to obtain a crude product. Secondary silica gel column chromatography ($CHCl_3$/MeOH 10/1, Rf 0.4) is performed to obtain 570 mg of pale yellow high-purity solid product with a yield of 32%. $^1$H-NMR (DMSO-$d^6$, 400 MHz): δ 7.51 (s, 1H), 6.77 (t, J=5.84, 1H), 6.54 (s, 2H), 6.08 (s, 2H), 5.69 (s, 2H), 3.77 (t, J=7.25 Hz, 2H), 3.71 (s, 6H), 3.52 (s, 2H), 2.95 (m, 2H), 1.53 (m, 3H), 1.37 (s, 9H); $^{13}$C-NMR (DMSO-$d^6$, 101 MHz): δ 162.22, 162.19, 155.69, 155.58, 152.85, 135.86, 134.64, 105.86, 105.78, 77.28, 72.02, 55.82, 32.97, 28.25, 27.01, 26.09; HRMS: $C_{22}H_{34}N_5O_5^+$ [M+H]$^+$ calc. 448.2560, found 448.2560.

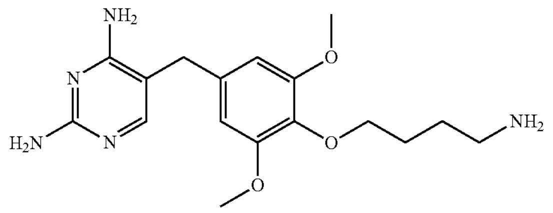 [SMILES: COc1cc(Cc2cnc(N)nc2N)cc(OC)c1OCCCCN]

5-(4-(4-aminobutoxy)-3,5-dimethoxybenzyl)pyrimidine-2,4-diamine (TMP-Bu-$NH_2$, 10). TMP-Bu-NHBoc (186 mg, 0.416 mmol) is dissolved in 1 ml of anhydrous dichloromethane (DCM), then 0.5 ml of trifluoroacetic acid (TFA) is added, and the mixture is stirred at room temperature for 1 h for deprotection. Volatile components such as DCM and TFA are removed in vacuum to obtain 144 mg of a trifluoroacetate salt product. The product is aliquoted into EtOAc/aq. $Na_2CO_3$, the organic layers are separated, and the aqueous layer is extracted several times with ethyl acetate. All organic layers are mixed, washed once with saturated brine, dried over anhydrous sodium sulfate, filtered, concentrated, and dried in vacuum to obtain 122 g of a white solid product with an almost quantitative yield. $^1$H-NMR (DMSO-$d^6$, 400 MHz): δ 7.51 (s, 1H), 6.53 (s, 1H), 6.06 (s, 1H), 5.67 (s, 1H), 3.77 (t, J=6.36 Hz, 2H), 3.71 (s, 6H), 2.55 (t, J=6.72 Hz, 2H), 1.61 (m, 2H), 1.45 (m, 2H); $^{13}$C-NMR (DMSO-$d^6$, 101 MHz): δ 162.24, 162.17, 155.72, 152.86, 135.60, 134.96, 105.90, 105.77, 72.36, 55.85, 41.41, 32.95, 29.72, 27.15; HRMS: $C_{17}H_{26}N_5O_3^+$ [M+H]$^+$ calc. 348.2036, found 348.2036.

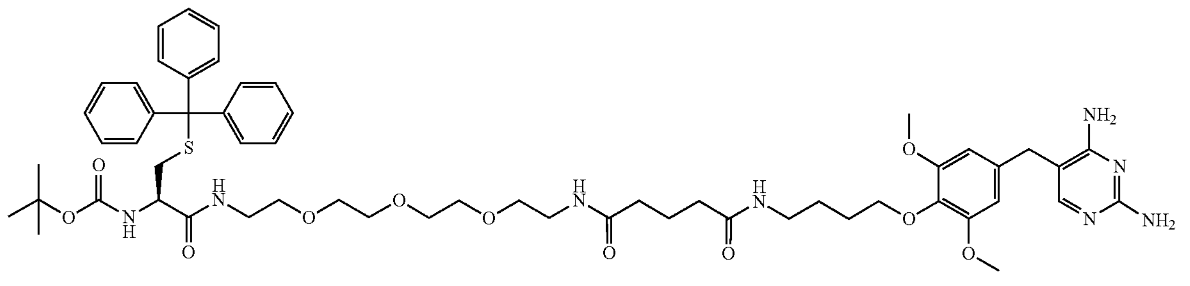 [SMILES: COc1cc(Cc2cnc(N)nc2N)cc(OC)c1OCCCCNC(=O)CCCC(=O)NCCOCCOCCOCCNC(=O)[C@H](CSC(c1ccccc1)(c1ccccc1)c1ccccc1)NC(=O)OC(C)(C)C]

(R)-tert-butyl 1-(2-(2-(2-(2-(5-(4-(4-((2,4-diaminopyrimidin-5-yl)methyl)-2,6-dimethoxyphenoxy)butylamino)-5-oxopentanamido)ethoxy)ethoxy)ethoxy)ethylamino)-1-oxo-3-(tritylthio)propan-2-ylcarbamate (BocCys(Trt)-TMP, 11). BocCys(Trt)-$PEG_4$-Glu-COOH (75.2 mg, 0.1 mmol) and DIEA (36 mg, 0.28 mmol) are added, the reaction solution is stirred for 5-10 min, and then TMP-Bu-$NH_2$ (35 mg, 0.1 mmol) is added. The reaction mixture is stirred at room temperature overnight to obtain a settled solution. The reaction solution is aliquoted into EtOAc/aq. $Na_2CO_3$, and then extracted twice with ethyl acetate. All organic layers are combined and washed with aq. $NaH_2PO_4$ (2 M), aq. $Na_2CO_3$, and saturated brine successively, then dried with anhydrous sodium sulfate, filtered, concentrated, and subjected to gradient silica gel column chromatography ($CHCl_3$/MeOH 10/1, 8/1, finally 5/1, Rf ($CHCl_3$/MeOH 5/1)=0.5) to obtain 61.2 mg of a pale yellow product with a yield of 57%. $^1$H-NMR (DMSO-$d^6$, 600 MHz): δ 7.84 (t, J=5.88 Hz, 1H), 7.77 (m, 2H), 7.49 (s, 1H), 7.32 (t, J=7.5 Hz, 6H), 7.28 (d, J=7.92 Hz, 6H), 7.24 (t, J=7.08 Hz, 3H), 6.92 (d, J=8.52 Hz, 1H), 6.54 (s, 1H), 6.38 (br, 2H), 5.97 (s, 2H), 4.12 (s, 2H), 3.92 (m, 1H), 3.78 (t, J=6.0 Hz, 2H), 3.70 (s, 6H), 3.52 (s, 2H), 3.47 (br, 4H), 3.45 (br, 4H), 3.19 (m, 1H), 3.12 (m, 1H), 3.05 (m, 2H), 2.04 (m, 2H), 1.55 (m, 2H), 1.53 (m, 2H), 1.37 (s, 9H); $^{13}$C-NMR (DMSO-$d^6$, 151 MHz): δ 171.88, 171.58, 170.15, 162.51, 161.00, 154.92, 152.91, 144.35, 135.28, 134.88, 129.12, 128.08, 128.79, 106.31, 105.88, 78.39, 72.00, 69.74, 69.63, 69.56, 69.16, 68.89, 65.87, 55.85, 53.41, 40.06, 38.68, 38.45, 38.17, 34.84, 34.77, 34.06, 32.88, 28.15, 27.16, 25.76, 21.63; HRMS: $C_{57}H_{77}N_8O_{11}S^+$ $[M+H]^+$ calc. 1081.5427, found 1081.5471.

-continued

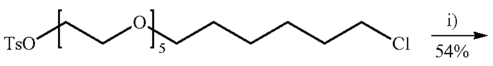

TsO-PEG5-Cl (13)

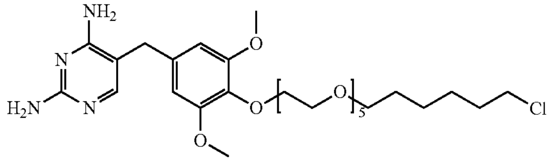

TMP-Cl (14)

i) $Cs_2CO_3$, DMF, RT, ON, Ar, 54% yield.

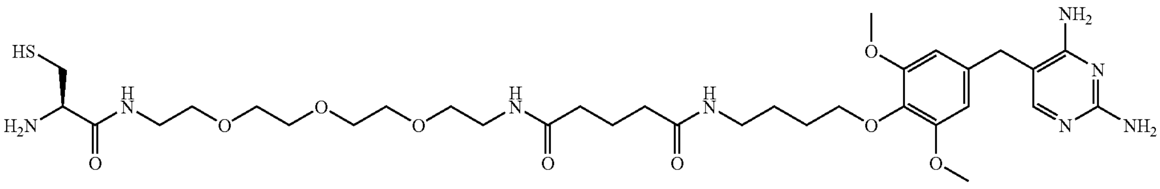

(R)—N1-(2-(2-(2-(2-(2-amino-3-mercaptopropanamido)ethoxy)ethoxy)ethoxy)ethyl)-N5-(4-(4-((2,4-diaminopyrimidin-5-yl)methyl)-2,6-dimethoxyphenoxy)butyl)glutaramide (CysTMP, 1). BocCys(Trt)-TMP (25 mg, 0.023 mmol) is dissolved in 1 ml of TFA, and then 25 μl of TIS is added. The reaction is performed in the presence of argon for 1 h at room temperature. Volatile components such as TFA and TIS are removed in vacuum to obtain a product aliquoted in EtOAc/$H_2O$. The organic layers are washed twice with ethyl acetate, concentrated, and dried in vacuum to obtain a white foam product with a yield of 86%. $^1$H-NMR (DMSO-$d^6$, 400 MHz): δ 8.54 (t, J=5.7 Hz, 1H, 8.29 (br, 3H), 7.84 (t, J=5.6 Hz, 1H), 7.77 (t, J=5.6 Hz, 1H), 7.74 (s, 1H), 7.64 (s, br, 2H), 7.44 (s, 1H), 6.60 (s, 2H), 3.95 (t, J=5.6 Hz, 1H), 3.79 (t, J=6.28 Hz, 2H), 3.73 (s, 6H), 3.59 (s, 2H), 3.51 (br, 4H), 3.50 (br, 4H), 3.39 (t, J=6.1 Hz, 2H), 3.34 (m, 1H), 3.26 (m, 1H), 3.18 (m, 2H), 3.06 (m, 2H), 2.90 (br, 2H), 2.05 (m, 4H), 1.68 (m, 2H), 1.57 (m, 4H); $^{13}$C-NMR (DMSO-$d^6$, 101 MHz): δ 171.88, 171.57, 166.72, 164.06, 154.28, 153.06, 139.77, 135.33, 132.79, 108.92, 106.30, 71.99, 69.71, 69.58, 69.53, 69.09, 68.71, 55.92, 53.90, 38.40, 38.13, 34.83, 34.77, 32.08, 30.75, 27.12, 25.72, 25.13, 21.60; HRMS: $C_{33}H_{55}N_8O_9S^+$ $[M+H]^+$ calc. 739.3807, found 739.3820.

Synthesis of Chemical Inducer of Proximity—TMP-Cl (14)

Reaction Scheme 2 | Synthetic route of CIP TMP-Cl (14)

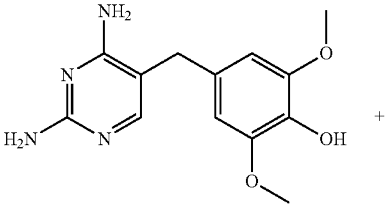

Dimethoprim (TMP-OH, 12)

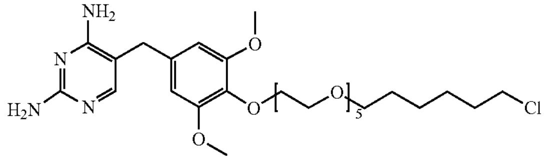

5-(4-((21-chloro-3,6,9,12,15-pentaoxahenicosyl)oxy)-3,5-dimethoxybenzyl) pyrimidine-2,4-diamine (TMP-Cl, 14). Dimethoprim (TMP-OH, 12) and TsO-$PEG_5$-Cl (13) are synthesized according to a previously reported scheme (Chen, et al. *Angew. Chem. Int. Ed.* 2017, 56, 5916). Then, TMP-OH (12, 50 mg, 0.18 mmol), TsO-$PEG_5$-Cl (13, 97.2 mg, 0.19 mmol) and $Cs_2CO_3$ (76.3 mg, 0.234 mmol) are added into a two-neck round bottom flask, anhydrous DMF (1.8 ml) is added, and the reaction suspension is rapidly stirred at room temperature overnight in the presence of argon to complete the coupling reaction. DMF is removed under vacuum. A small amount of methanol is added and dissolved, and then vacuum is applied, which process is repeated about three times to remove DMF more thoroughly. The dried residue is aliquoted into EtOAc/$Na_2CO_3$ (aq.), then the organic layers are separated, and the aqueous layer is extracted twice with ethyl acetate. All organic layers are combined, washed twice with saturated brine, dried over anhydrous $Na_2SO_4$, filtered, concentrated under reduced pressure, and subjected to gradient silica gel column chromatography (EtOAc:MeOH 10:1→8:1→DCM:MeOH 10:1)) to obtain 60.4 mg of a white solid product with a yield of 54%. The NMR and MS characterization data are consistent with the above-mentioned literature. $^1$H-NMR (DMSO-$d^6$, 600 MHz): δ 7.50 (s, 1H), 6.54 (s, 2H), 6.11 (s, 2H), 5.72 (s, 2H), 3.90 (t, 2H, J=5.1 Hz), 3.71 (s, 6H), 3.63-3.69 (m, 4H), 3.56 (m, 2H), 3.48-3.53 (m, 14H), 3.45 (m, 2H), 3.35 (t, 2H, t, J=6.48 Hz), 1.70 (m, 2H), 1.47 (m, 2H), 1.37 (m, 2H), 1.29 (m, 2H). MS(ESI): $C_{29}H_{48}O_8N_4Cl^+$ $[M+H]^+$, calcd. 615.32, found 615.42.

Synthesis of Cys-Cl (20)

Scheme 3 | Synthetic scheme for the synthesis of Cys-Cl (20)

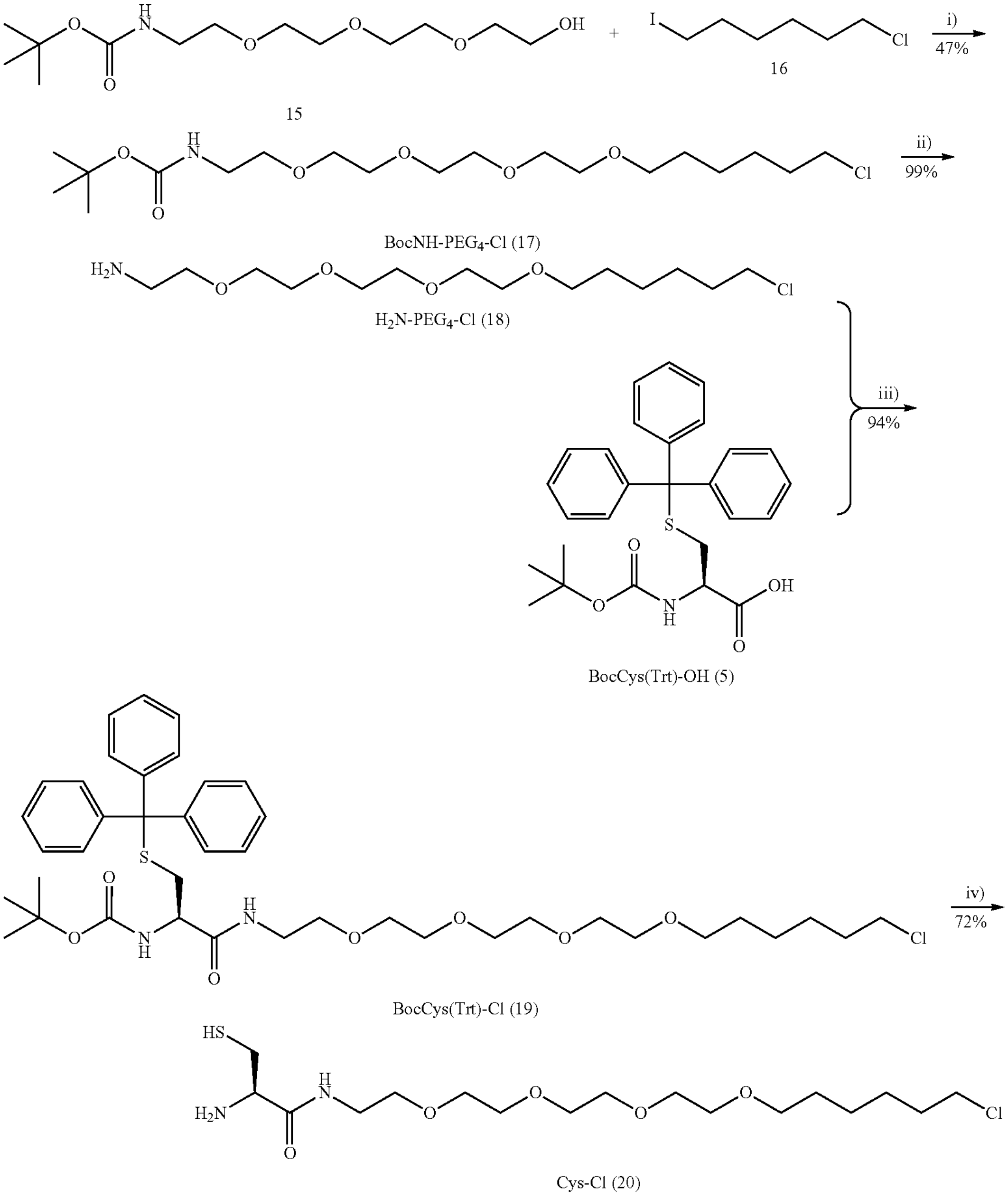

i) KOH, THF, RT, ON. ii) TFA, DCM, RT, 20 min. iii) HBTU, DIEA, HOBt, DMF, RT, ON. iv) TFA, TIPS, RT, 4 h.

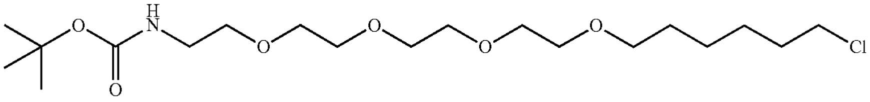 [SMILES: CC(C)(C)OC(=O)NCCOCCOCCOCCOCCCCCCCl]

tert-Butyl (18-chloro-3,6,9,12-tetraoxaoctadecyl)carbamate (BocNH-PEG$_4$-Cl, 17). alcohol (15) (293 mg, 1.0 mmol) and Iodide (16) (278 mg, 1.05 mmol) starting materials were dissolved in THE (4 ml), and then KOH (72.4 mg, 85%) was also added. The reaction suspension was stirred at RT overnight. The next day, aq. $NaH_2PO_4$ solution was added to quench the reaction and the reaction mixture was extracted three times by EtOAc. EtOAc was removed under reduced pressure and the crude product was purified via silica gel chromatography (cyclohexane→cyclohexane/EtOAc 3/2→1/1→2/3) to give 193.5 mg oil product in a yield of 47%. $^1$H-NMR ($CDCl_3$, 600 MHz): δ 5.07 (s, 1H), 3.67-3.62 (m, 8H), 3.62-3.59 (m, 2H), 3.59-3.56 (m, 2H), 3.54-3.50 (m, 4H), 3.44 (t, 2H, J=6.67 Hz, 2H), 3.30 (m, 2H), 1.76 (m, 2H), 1.59 (m, 2H), 1.45 (m, 2H), 1.43 (s, 9H), 1.36 (m, 2H). $^{13}$C-NMR ($CDCl_3$, 600 MHz): δ 156.15, 79.26, 71.36, 70.74, 70.72, 70.65, 70.36, 70.22, 45.19, 40.48, 32.67, 29.57, 28.55, 26.82, 25.55; HRMS(ESI): $C_{19}H_{38}ClNO_6Na^+$, calcd. 434.2285, found 434.2286 [M+Na]$^+$ 2→EtOAc) to give 143 mg white foamy solid as the product in a yield of 94%. $^1$H-NMR ($CDCl_3$, 600 MHz): δ 7.40 (s, 3H), 7.38 (s, 3H), 7.29 (m, 6H), 7.23 (m, 3H), 6.46 (s, 1H), 4.88 (m, 1H), 3.88 (m, 1H), 3.67-3.62 (m, 4H), 3.61-3.58 (m, 2H), 3.58-3.52 (m, 6H), 3.52-3.45 (m, 6H), 3.45-3.40 (m, 1H), 3.38-3.30 (m, 1H), 2.71 (m, 1H), 2.51 (dd, $J^1$=13.1 Hz, $J^2$=5.34 Hz, 1H), 1.73 (m, 2H), 1.58 (m, 2H), 1.42 (s, 9H), 1.39 (m, 2H), 1.31 (m, 2H); $^{13}$C-NMR ($CDCl_3$, 600 MHz): δ 171.77, 155.54, 144.48, 129.67, 128.21, 127.10, 80.53, 71.55, 70.86, 70.42, 70.10, 69.88, 69.63, 69.37, 67.28, 53.73, 45.30, 39.39, 38.74, 33.97, 32.60, 29.01, 28.40, 26.78, 25.28; HRMS(ESI): $C_{41}H_{57}ClN_2O_7SNa^+$, calcd. 779.3473, found 779.3468 [M+Na]$^+$.

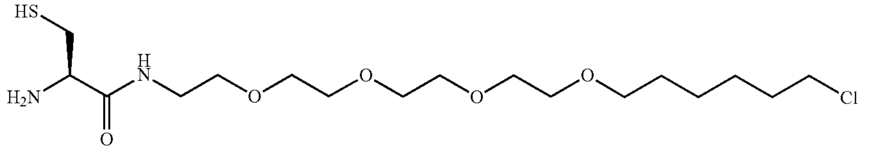

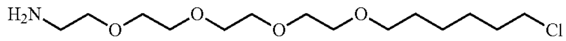 [SMILES: NCCOCCOCCOCCOCCCCCCCl]

18-Chloro-3,6,9,12-tetraoxaoctadecan-1-amine ($H_2N$-$PEG_4$-Cl, 18). BocNH-$PEG_4$-Cl (17) (182.5 mg, 0.443 mmol) was dissolved in DCM (1 ml) and TFA (0.5 ml) was added. The reaction solution was stirred at RT for 20 min. DCM and TFA were removed under high vacuum to give 209 mg (0.44 mmol) deprotected $H_2N$-$PEG_4$-Cl (18) in a quantitative yield. $^1$H-NMR ($CDCl_3$, 600 MHz): δ 8.05 (s, 3H), 5.70 (s, 2H), 3.85 (m, 2H), 3.76 (m, 2H), 3.67 (m, 2H), 3.65-3.60 (m, 8H), 3.53 (t, 2H, J=6.67H), 3.50 (t, J=7.08 Hz, 2H), 3.14 (m, 2H), 1.76 (m, 2H), 1.58 (m, 2H), 1.44 (m, 2H), 1.33 (m, 2H); $^{13}$C-NMR ($CDCl_3$, 600 MHz): δ 71.62, 70.78, 70.44, 70.11, 70.08, 69.97, 67.56, 45.10, 40.24, 32.54, 29.27, 26.66, 25.21; HRMS(ESI): $C_{14}H_{31}ClNO_4^+$, calcd. 312.1936, found 312.1940 [M+H]$^+$.

(R)-2-Amino-N-(18-chloro-3,6,9,12-tetraoxaoctadecyl)-3-mercaptopropanamide (Cys-Cl, 20). Boc-Cys(Trt)-Cl (19) (141.2 mg, 0.187 mmol) was dissolved in TFA (2 ml) and TIPS (50 μl) was added. The reaction solution was stirred at RT for 4 hours to allow complete deprotection. TFA and TIPS were mostly removed under high vacuum and the residue was dissolved in DI—$H_2O$, washed three times by EtOAc and the aqueous solution was concentrated under reduced pressure. The product was dried in vacuo to give 71.4 mg Cys-Cl (20) product in 72% yield. $^1$H-NMR ($D_2O$, 600 MHz): 4.15 (t, J=6.2 Hz, 1H), 3.69-3.64 (m, 15H), 3.60 (t, J=7.98 Hz, 2H), 3.53 (t, J=6.78 Hz, 2H), 3.51 (t, J=5.82 Hz, 1H), 3.43-3.38 (m, 1H), 3.05 (m, 2H), 1.76 (m, 2H), 1.58 (m, 2H), 1.43 (m, 2H), 1.35 (m, 2H); $^{13}$C-NMR ($D_2O$, 600 MHz): 167.85, 70.93, 69.59, 69.56, 69.52, 69.47, 69.30, 69.03, 68.54, 54.42, 45.60, 39.08, 31.73, 28.30, 25.77, 24.81, 24.42; HRMS(ESI): $C_{17}H_{36}ClN_2O_5S$ calcd. 415.2028, found 415.2036 [M+H]$^+$.

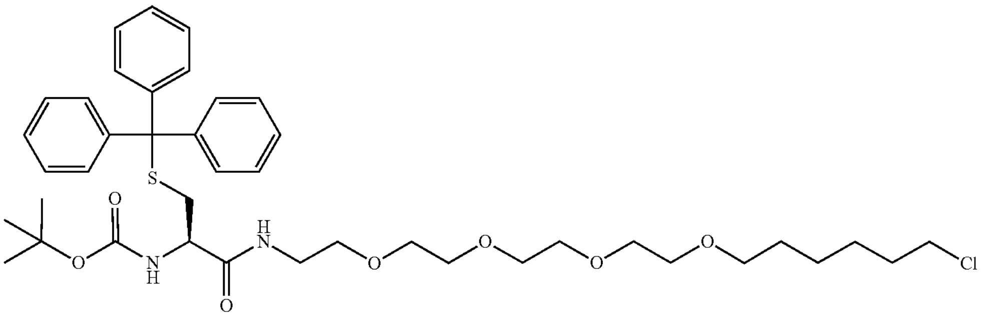 [SMILES: CC(C)(C)OC(=O)N[C@@H](CSC(c1ccccc1)(c1ccccc1)c1ccccc1)C(=O)NCCOCCOCCOCCOCCCCCCCl]

tert-Butyl (R)-(24-chloro-5-oxo-1,1,1-triphenyl-9,12,15,18-tetraoxa-2-thia-6-azatetracosan-4-yl)carbamate (BocCys(Trt)-Cl, 19). BocCys-OH (93 mg, 0.2 mmol), HBTU (83 mg, 0.22 mmol), HOBt (13.5 mg, 0.1 mmol), and DIEA (171 μl, 1 mmol) were dissolved in DMF and stirred at RT for 10 min. Then $H_2N$-$PEG_4$-Cl (100 mg, 0.21 mmol) was added. The reaction solution was stirred at RT overnight. Aq. $Na_2CO_3$ solution was added to quench the reaction and the reaction mixture was extracted three additional times by EtOAc. Organic layers were combined, washed with brine for two times, dried over anhydrous $Na_2SO_4$, and the organic solution was directed subjected to silica gel chromatography (cyclohexane→cyclohexane/EtOAc 2/1→1/1→1/

Synthesis of Azidocyanobenzothiazole AzidoCBT (ACBT, 23)

Reaction Scheme 3 | Synthetic route of azidocyanobenzothiazole ACBT (23)

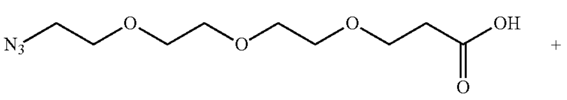

Azido-$PEG_3$-acid (21)

-continued

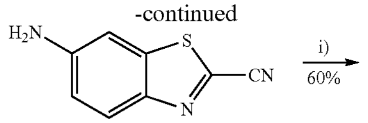

Amino-CBT (22)

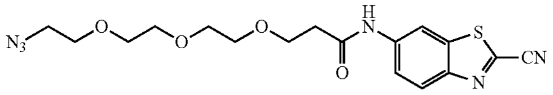

Azido-CBT (ACBT, 23)

i) HATU, DIEA, DMF, RT, 1 day, 60% yield.

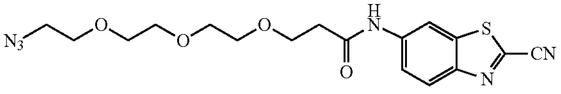 [SMILES: N#Cc1nc2ccc(NC(=O)CCOCCOCCOCCN=[N+]=[N-])cc2s1]

3-(2-(2-(2-Azidoethoxy)ethoxy)ethoxy)-N-(2-cyano-benzo[d]thiazol-6-yl)propenamide (ACBT, 23). Azido-$PEG_3$-acid (33.5 mg, 0.136 mmol, 21) is dissolved in 0.6 ml of anhydrous DMF in a thoroughly dried round bottom flask (RBF). HATU (57.5 mg, 0.136 mmol) and DIEA (38 mg, 0.29 mmol) are added and stirred in the presence of argon for several minutes, then amino-CBT (20 mg, 0.113 mmol, 22) is added, and the reaction is performed under stirring at room temperature for 1 day. The reaction solution is aliquoted into EtOAc/$NaH_2PO_4$ (2M), the organic layers are separated, and the aqueous layer is washed twice with ethyl acetate. All organic layers are combined, washed once with saturated sodium bicarbonate (sat. $Na_2CO_3$), filtered, concentrated, and subjected to silica gel column chromatography (EtOAc, Rf 0.25) to obtain 27.7 mg of a viscous yellowish oily product with a yield of 60%. $^1$H-NMR (DMSO-$d^6$, 600 MHz): δ 10.47 (s, 1H), 8.76 (t, J=2.22 Hz, 1H), 8.18 (dd, $J^1$=8.94 Hz, $J^2$=1.92 Hz, 1H), 7.73 (d, J=9 Hz, 1H), 3.73 (td, $J^1$=6.24 Hz, $J^2$=1.98 Hz, 2H), 3.48-3.55 (m, 11H), 3.33 (s, 2H), 2.63 (td, $J^1$=6.02 Hz, $J^2$=1.98 Hz, 2H); $^{13}$C-NMR (DMSO-$d^6$, 151 MHz): 170.05, 147.55, 139.71, 136.79, 134.92, 124.83, 120.65, 113.66, 111.09, 69.81, 69.76, 69.74, 69.68, 69.24, 66.54, 49.97, 37.33; HRMS: $C_1H_{20}N_6O_4SNa^+$ $[M+Na]^+$ calcd. 427.1159, found 427.1151.

Part 1: Design, Preparation, Characterization, and Cellular Regulatory Use of Universal SNACIP Inducer—cRGT

Figure 1:
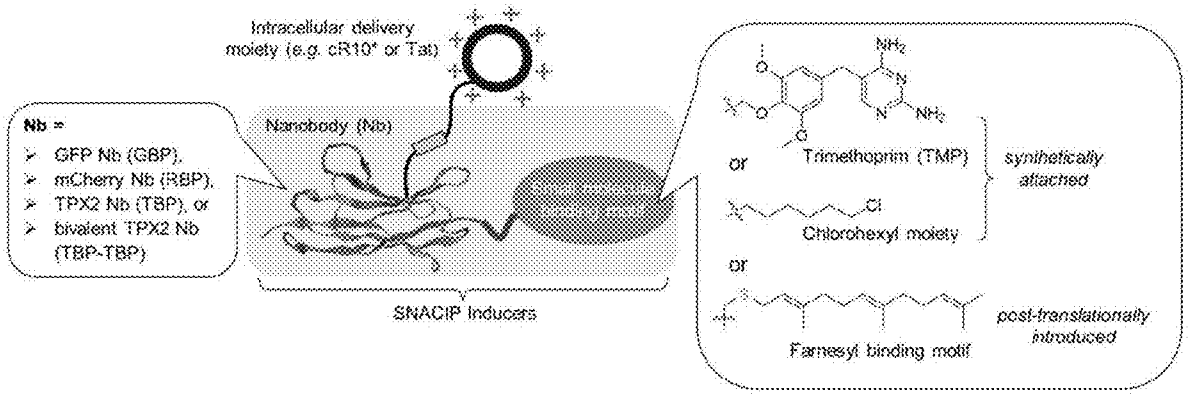
FIG. 1 is a schematic diagram of the overall structure of SNACIP inducers. The SNACIP includes a nanobody targeting moiety, a small molecule binding motif, an intracellular delivery moiety and the corresponding linker, wherein the small molecule binding motif may be pre-introduced directly by chemical ligation or introduced based on a post-translational modification mechanism after entering a living cell (latent SNACIP).

Example 1: General Strategy for Designing and Preparing Small Molecule Nanobody Conjugate SNACIP Inducer The general structural formula of the SNACIP inducers is as follows: small molecule binding motif-nanobody targeting moiety-linker-intracellular delivery moiety. The schematic diagram is shown in FIG. 1.

The corresponding SNACIP inducers are prepared by a fusion expression method and a chemical coupling method according to the above general structural formula:

(1) Introduction of small molecule binding motif: For general SNACIP inducers, the small molecule binding motif is introduced by bioconjugation. For latent SNACIP inducers, the small molecule is introduced by post-translational modification, and the nanobody should carry the corresponding post-translationally modified polypeptide sequence.

(2) Introduction of nanobody targeting moiety: The nanobody targeting moiety is expressed with a known nanobody sequence, or a new nanobody may be prepared by other means, e.g., phage display technology.

(3) Linker: A cyclic cell-penetrating peptide or other cell-penetrating moieties that cannot be expressed by genes are introduced by bioconjugation, and the linker may be a covalent bond, including thioether bond and disulfide bond. A polypeptide linear cell-penetrating peptide such as a Tat sequence may be introduced by direct fusion expression (a polypeptide bond).

(4) Intracellular delivery moiety: Cyclic cell-penetrating peptide is an excellent cell-penetrating moiety. Linear cell-penetrating peptides may also be used; because nanobodies are small, a part of the SNACIP inducers can enter cells in a non-endocytotic form and be released in the cytoplasm.

The intracellular delivery moiety can be one of the following: new cyclic cell-penetrating peptide-cR10*,

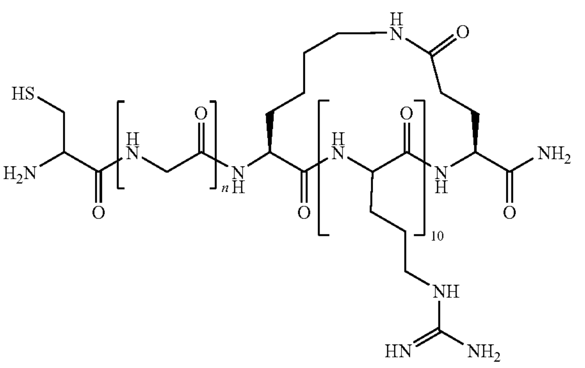

n = 0, 1, 2, 3, ...

Cys-$(Gly)_n$-cyclic(KrRrRrRrRrRE)-$NH_2$ (SEQ ID NO:12) where n is zero or a natural number, r: L-Arg, R: L-Arg.

Example 2: Design of Three Different SNACIP Inducers (1) General-purpose SNACIP inducer, for example cRGT, can achieve regulation of the function of proteins fused with a fluorescent protein tag (GFP and its variants or mCherry and its variants) or an eDHFR (SEQ ID NO:5) tag and the corresponding cellular processes, with the structural elements shown in a of FIG. 2.

Figure 2:
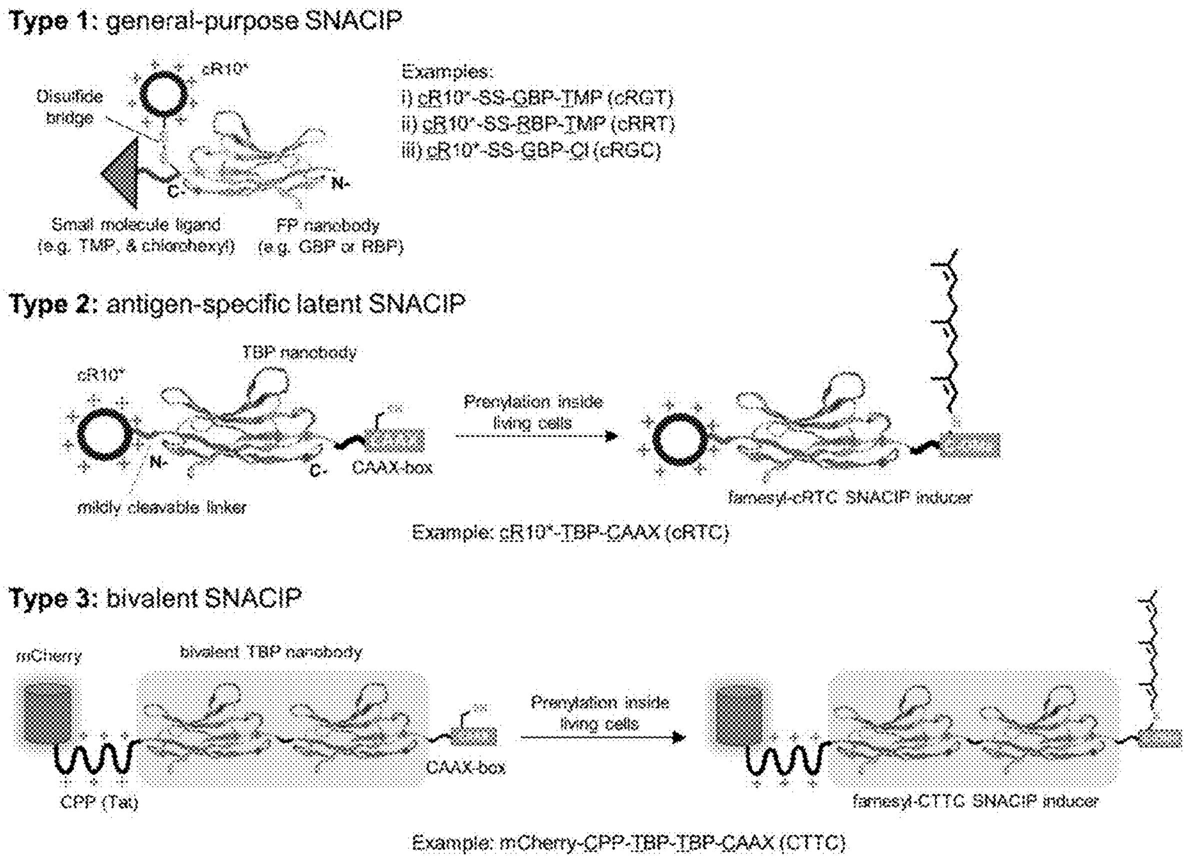
FIG. 2 shows schematic structural diagrams of three types of SNACIP inducers, respectively, i) general-purpose SNACIP (e.g. cRGT, cRRT, and cRGC), ii) antigen-specific SNACIP (e.g. cRTC), and iii) bivalent SNACIP (e.g. CTTC).

(2) Antigen-specific SNACIP inducer, for example cRTC, can directly regulate the targets of intrinsically disordered proteins and ligand-free binding proteins, with the structural elements shown in b of FIG. 2.

(3) A bivalent SNACIP inducer, for example CTTC, is more suitable for regulating the function of proteins in vivo, and has the potential to be developed into a nanobody-conjugate drug, with the structural elements shown in c of FIG. 2.

Example 3: Design, Construction and Biochemical Characterization of the General SNACIP Inducer-cRGT Since green fluorescent protein (GFP) is currently one of the most widely used fluorescent proteins (FPs), direct regulation of the function of GFP-fused proteins will be a general regulatory means. In addition, GFP is also a fluorescent molecule, which means that a protein of interest can be simultaneously regulated and imaged. So far, no small molecule ligands that directly bind GFP with high affinity have been reported, so GFP is also a target protein without small molecule ligands.

Figure 3A:
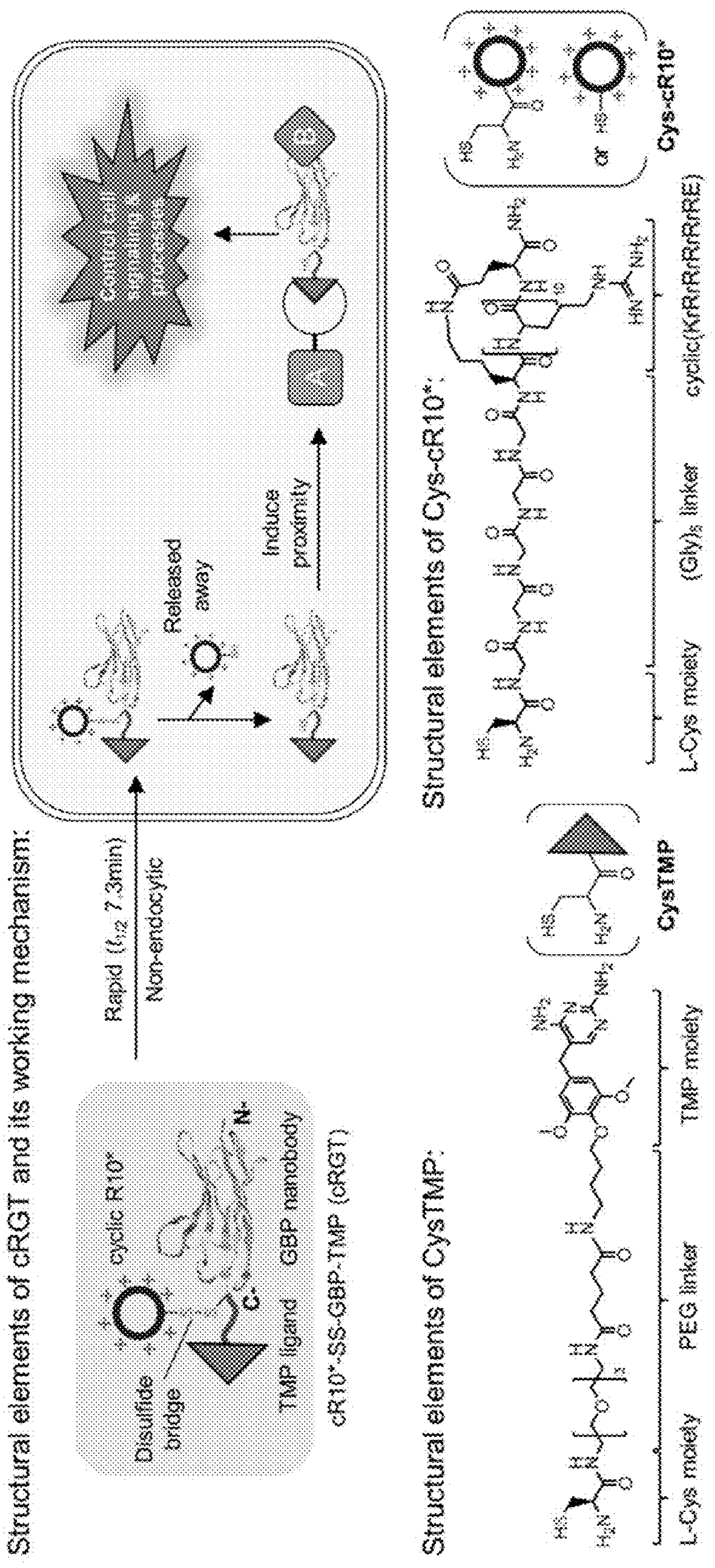
FIG. 3A shows the schematic diagram of the structural elements of the cRGT and working principle thereof, as well as the structural elements of CysTMP and Cys-cR10* (r: D-Arg, R: L-Arg).
Figure 3B:
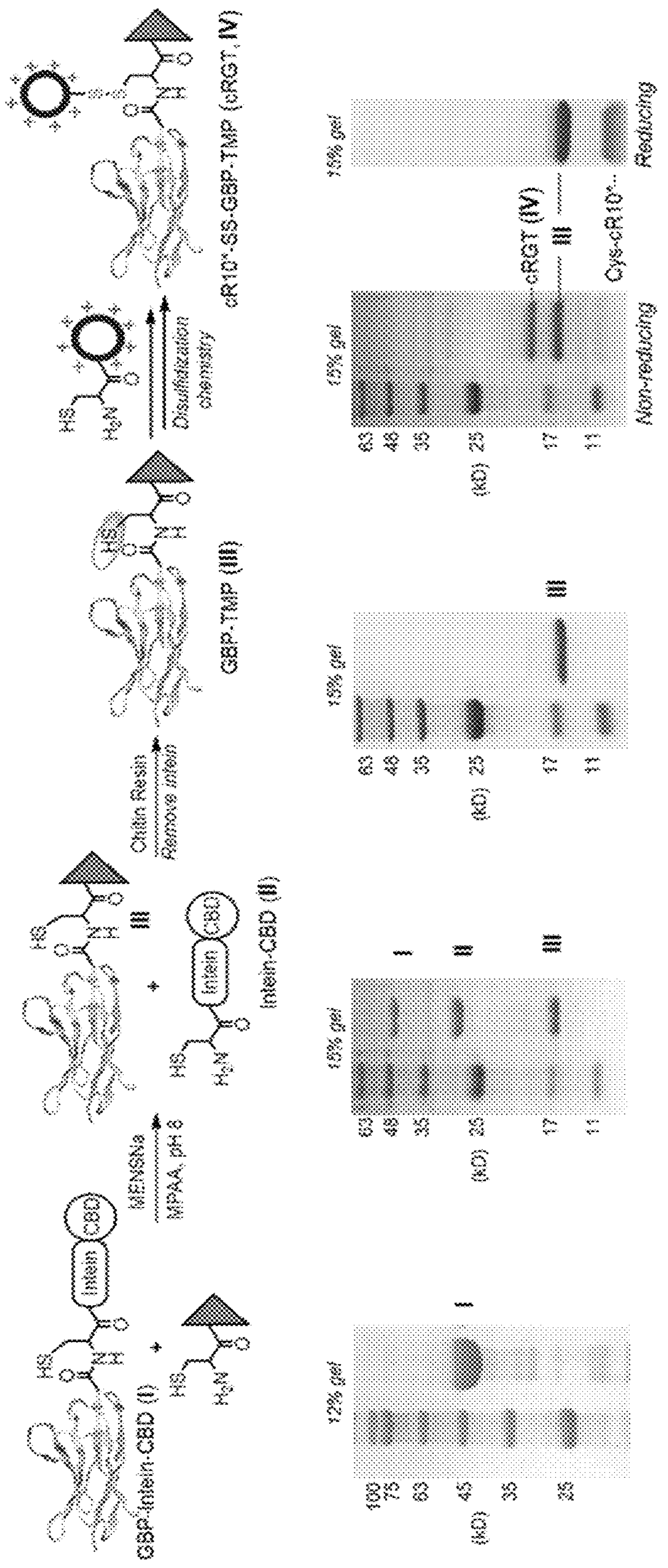
FIG. 3B shows two-step construction of cRGT(IV), the first step being EPL and the second step being a disulfidization reaction, and reducing/non-reducing SDS-PAGE gel electrophoresis analysis of GBP-intein-CBD(I), GBP-TMP (III), cRGT(IV).
Figure 4:
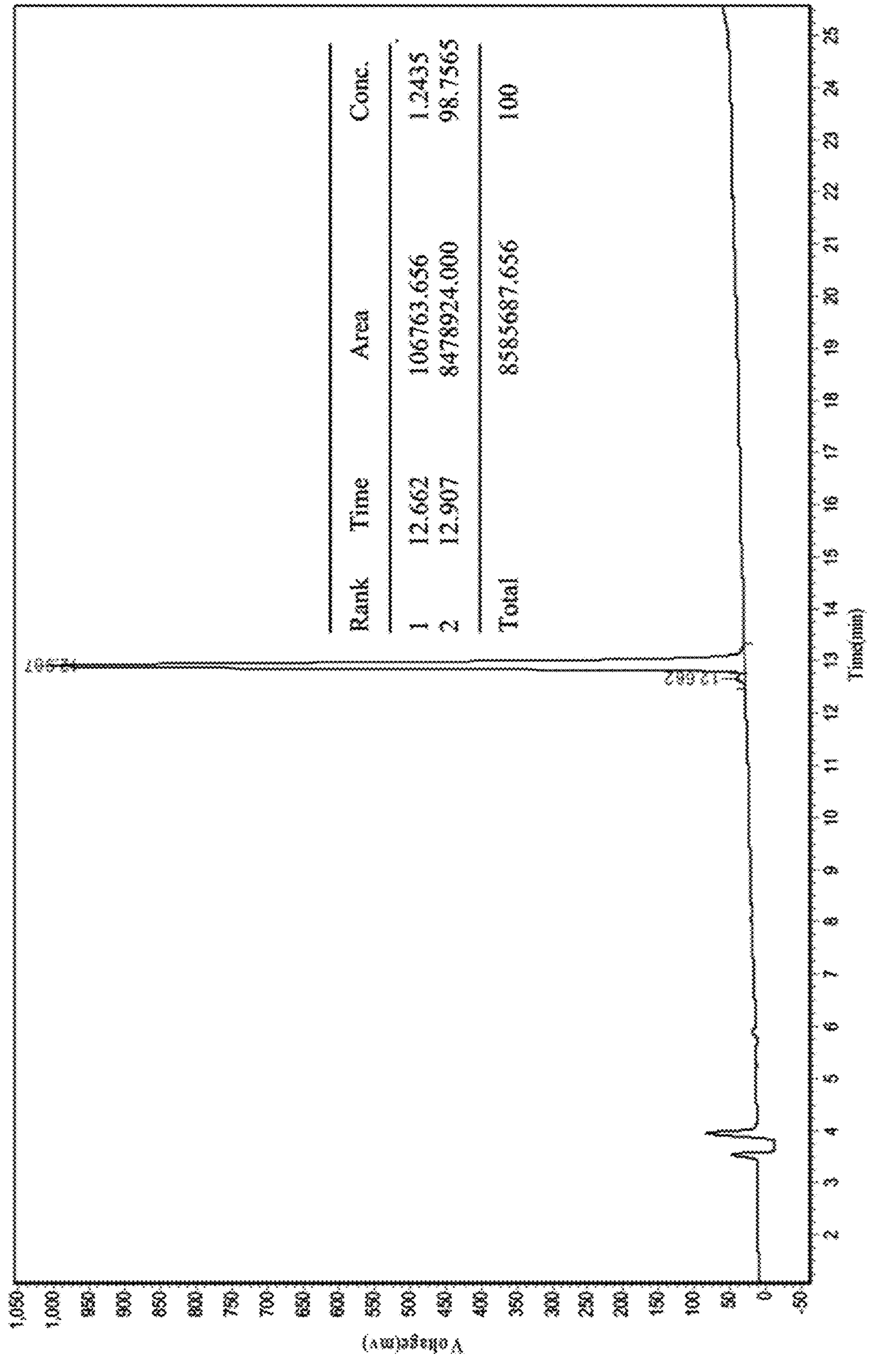
FIG. 4 shows identification of a Cys-cR10* cyclic cell-penetrating peptide by HPLC.

General SNACIP inducer of dimerization—cR10*-SS-GBP-TMP, or cRGT (FIG. 3A): cRGT contains a GFP binding protein (GBP, $K_d$=1.4 nM) nanobody targeting moiety, and a trimethoprim (TMP) small molecule ligand targeting moiety. Since TMP can bind to *E. coli* dihydrofolate reductase (eDHFR) with high affinity reversibly, cRGT can induce dimerization between GFP and eDHFR. A new cyclic cell-penetrating peptide-cR10*, is linked to GBP-TMP via a cleavable disulfide bond to obtain cRGT. After cR10* helps cRGT to pass through the plasma membrane (PM), cR10* may be rapidly cleaved from cRGT in a reducing environment in the cell, to avoid possible effects of cR10* on the GBP-TMP inducer of dimerization (FIG. 3A, right). The specific synthesis method is as follows:

First, a CysTMP chemical small molecule was synthesized. The CysTMP was used for introducing a TMP ligand onto a GBP nanobody (a Cys-TMP synthesis method is shown in reaction scheme 1). CysTMP contained an N-terminal cysteine, a water-soluble PEG linker, and a TMP moiety for binding an eDHFR protein tag (the structure is shown in FIG. 3A). Also, the Cys-cR10* cyclic cell-penetrating peptide might also be synthesized by classical peptide solid-phase synthesis (FIG. 4). Cys-cR10* contained an L-Cys residue, a $(Gly)_5$ linker, and a cyclic (KrRrRrRrRrRE) cyclic cell-penetrating peptide (the structure is shown in FIG. 3A). After CysTMP and Cys-cR10* were prepared, cRGT might be rapidly constructed in only two steps (FIG. 3B).

Step 1, expressed protein ligation (EPL): CysTMP and GBP-intein-CBD (intein-chitin binding domain tag-fused GFP nanobody) (FIG. 3B, chimera I) reacted through an EPL reaction to ligate the TMP ligand to the C-terminal end of the GBP nanobody to obtain GBP-TMP (FIG. 3B, chimera Ill). The CBD tag was also cleaved during the ligation reaction (FIG. 3B, chimera II), and pure GBP-TMP was easily obtained after purification on a trans nickel column.

Step 2, disulfidization reaction: The GBP-TMP conjugate carrying the cysteine residue was covalently bound to the Cys-cR10* cell-penetrating peptide through a disulfide bond. Based on the disulfidization reaction, a <u>c</u>R10*-SS-<u>G</u>BP-<u>T</u>MP product, cRGT (FIG. 3B, conjugate IV), was constructed, and cR10* was easily cleaved under a reducing condition to obtain GBP-TMP.

The more detailed preparation steps are as follows:

(1) GBP-Intein-CBD was purified by Ni-NTA IMAC and exchanged into a buffer A (pH 8.0, PBS, containing 0.5 M NaCl, 3% glycerol, and imidazole);

(2) MENSNa (2 M stock) (pH 8.0) was added to a final concentration of 0.4 M and MPAA (1.1 M stock) (pH 8.0) to a final concentration of 0.2 M;

(3) CysTMP (25 mM stock) was added to a final concentration of 1 mM for incubation on ice for 1 day; the next day, additional CysTMP with a final concentration of 1 mM was added for incubation on ice for another 2 days;

(4) the cleaved intein and some unreacted GBP-Intein-CBD were removed by Ni-NTA IMAC purification;

(5) Chitin resin pre-equilibrated with buffer A was used for mixed incubation, and the effluent was collected after rotating at 4 degrees for 2 h;

(6) The chimera was exchanged into a DTNP buffer (pH 8.3, 50 mM $Na_2HPO_4$, 0.5 M NaCl) by ultrafiltration, and 2 equivalents of TCEP (20 mM stock) was added for incubation for 45 min;

(7) 10 equivalents of DTNP (100 mM stock) was added for incubation for 60 min, then the chimera was ultrafiltered 3 times and exchanged into a disulfidization buffer (pH 9.0, 50 mM HEPES, 0.5 M NaCl), and excess DTNP and other small molecules were removed by ultrafiltration;

(8) Cys-cR10* (25 mM stock in DMSO) was added to a final concentration of 1 mM for incubation on ice for 30 min; and (9) The protein was ultrafiltered once and exchanged into a PBS solution to obtain the cRGT nanobody conjugate dimerization drug molecule, which was measured the concentration, aliquoted, frozen in liquid nitrogen, and stored at −80 °C in a refrigerator.

Figure 3C:
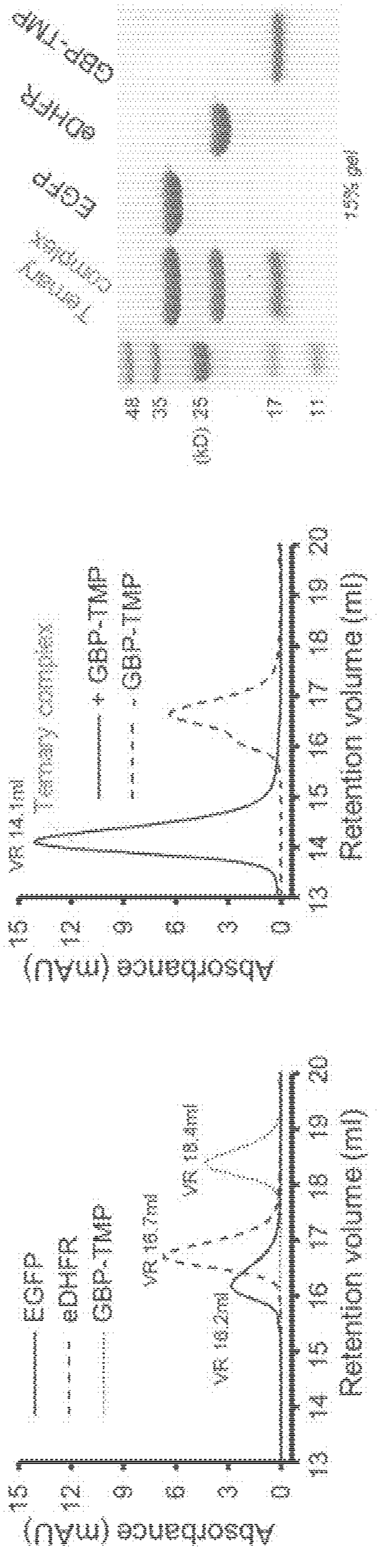
FIG. 3C shows size exclusion chromatographic (SEC) analysis demonstrating that GBP-TMP induces the dimerization between EGFP and eDHFR. In this analysis, 1 nmol EGFP, eDHFR, GBP-TMP, EGFP/eDHFR mixture, or EGFP/GBP-TMP/eDHFR ternary complex was subjected to SEC analysis using a Superdex 200 Increase 10/300 GL column with a flow rate of 0.4 $ml\text{-}min^{1}$, showing that only in the presence of GBP-TMP, EGFP/GBP-TMP/eDHFR ternary complex was formed. EGFP, eDHFR, GBP-TMP and the EGFP/GBP-TMP/eDHFR ternary complex used in SEC were further analyzed by denaturing SDS-PAGE.
Figure 3D:
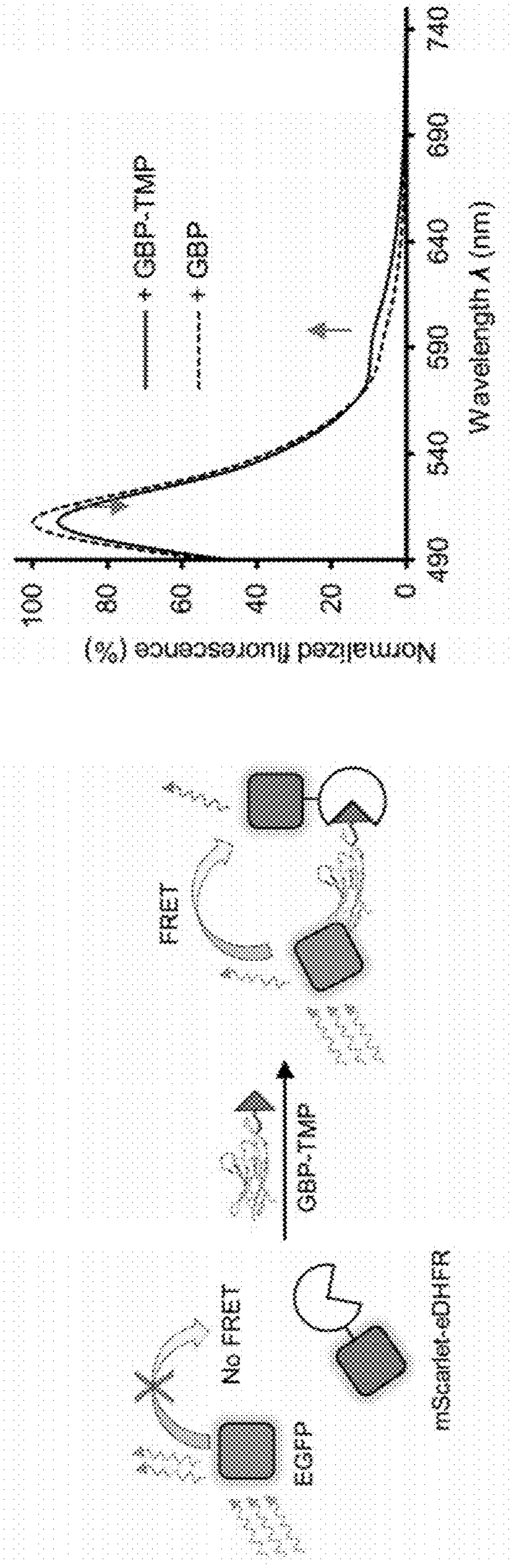
FIG. 3D shows a principal flow chart of dimerization between eDHFR and EGFP induced by GBP-TMP by Förster resonance energy transfer (FRET); Spectral FRET map results, showing that Förster energy transfer from the EGFP donor to mScarlet-eDHFR occurs in the presence of GBP-TMP but not in the presence of GBP alone. In this assay, a slight excess of GBP-TMP or GBP was added to a reducing PBS solution of 5 μM EGFP and 5 μM mScarlet-eDHFR (pH 7.4, containing 1 mM TCEP, 3% glycerol, 0.5 M NaCl), and fluorescence spectra were recorded with a fluorometer with an excitation wavelength set to 470 nM.

It was confirmed by size exclusion chromatography (SEC) that a GBP-TMP nanobody conjugate can indeed induce dimerization between EGFP and eDHFR. It can be seen that in the presence of GBP-TMP, a stable EGFP/GBP-TMP/eDFHR ternary complex could be formed, while in the absence of GBP-TMP, eDHFR and EGFP could not form a protein complex (FIG. 3C). The dimerization process was further confirmed by means of Föster resonance energy transfer (FRET), and it can be seen that the EGFP fluorescent protein donor and the mScarlet-eDHFR fluorescent protein acceptor interacted in the presence of GBP-TMP (FIG. 3D).

Figure 5A:
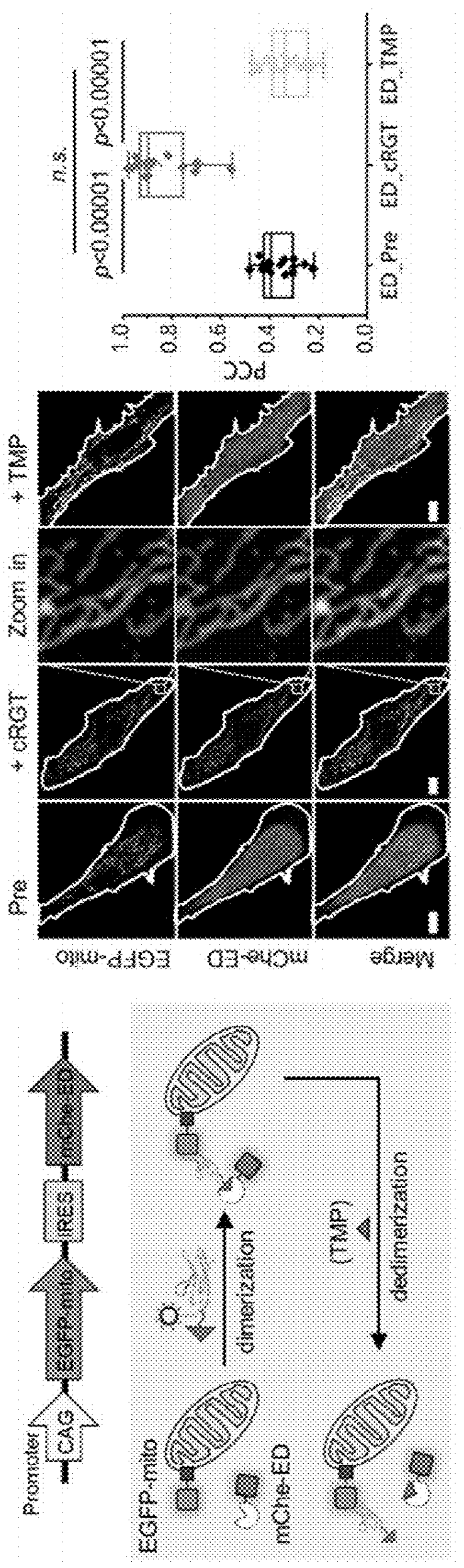
FIG. 5A shows the schematic diagram of the principle flow of the assay, using a bicistronic plasmid vector to co-express EGFP-mito (mitochondria localized; mito: mitochondrial localization polypeptide sequence) and mCherry-eDHFR (mainly cytoplasm localized); the confocal micrographs (left) of HeLa cells before addition of cRGT (Pre), after addition of 24 μM cRGT, and after addition of 10 μM TMP were shown; statistical PCC analysis of colocalization between mCherry and EGFP channels was also shown.

Example 4: CRGT can Rapidly Penetrate the Cell and Achieve No-Wash, Reversible, Dose-Dependent and Thorough Regulation of Intracellular Dimerization Between EGFP and eDHFR A bicistronic vector was used for co-expressing EGFP-mito and mCherry-eDHFR in living HeLa cells and testing the regulatory effect of cRGT on intracellular dimerization (FIG. 5A). HeLa cells were treated with 24 μM cRGT for 1.5 h and used directly for microscopic imaging analysis without washing. It can be found that cRGT localized mCherry-eDHFR from the cytoplasm to the mitochondria (SEQ ID NO:6) where EGFP-mito is (mito: mitochondrial localization polypeptide sequence). From zoomed-in high-resolution confocal images and a Pearson correlation coefficient value close to 1.0, it can be seen that the localization regulation was very thorough, which could be attributed to the formation of the stable EGFP/GBP-TMP/eDHFR ternary protein complex as demonstrated above. The high colocalization value compared to a previously reported comparable CID system (PCC: 0.65-0.75) shows that cRGT is an excellent inducer of dimerization. Since trimethoprim (TMP) is a known inhibitor of the eDHFR protein tag, when TMP was added to a cell culture medium at a final concentration of 10 μM, dedimerization was induced within minutes, showing that the cRGT-induced dimerization system is also reversible.

Figure 5B:
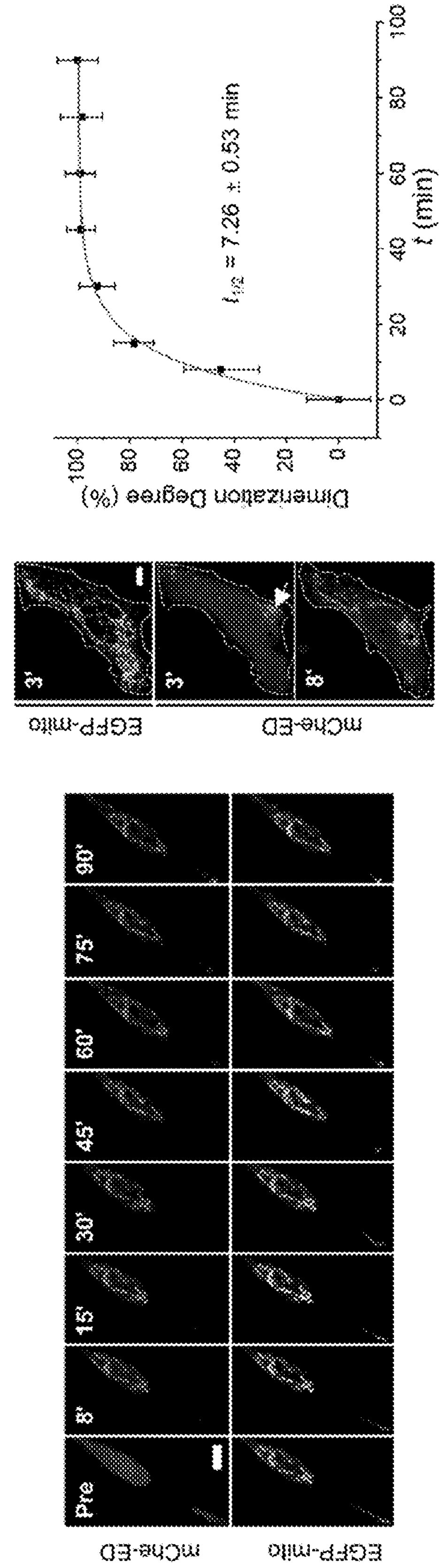
FIG. 5B shows that time-dependent dimerization of HeLa cells treated with 24 μM cRGT. cRGT started to penetrate cells polarly from 3 min and induce subcellular local dimerization (indicated by the yellow arrow), resulting in an intensive dimerization effect within 8 min. A curve of the normalized PCC value-based dimerization induction degree as a function of time, showing that the semi-dimerization induction time $t_{1/2}$ was 7.26±0.53 min.

The kinetics of cRGT penetrating into cells and inducing dimerization was subsequently investigated (FIG. 5B). It was found that cRGT could penetrate cells in as fast as 3 min and induce significant intracellular dimerization within 8 min. Kinetic studies showed that cRGT induced maximum dimerization at $t_{1/2}$=7.26±0.53 min, being a rate almost comparable to the most efficient CID system. Accordingly, cRGT is an excellent inducer of dimerization, and can be used for regulating and analyzing rapid biological processes, and also regulating low-concentration target proteins.

Figure 5C:
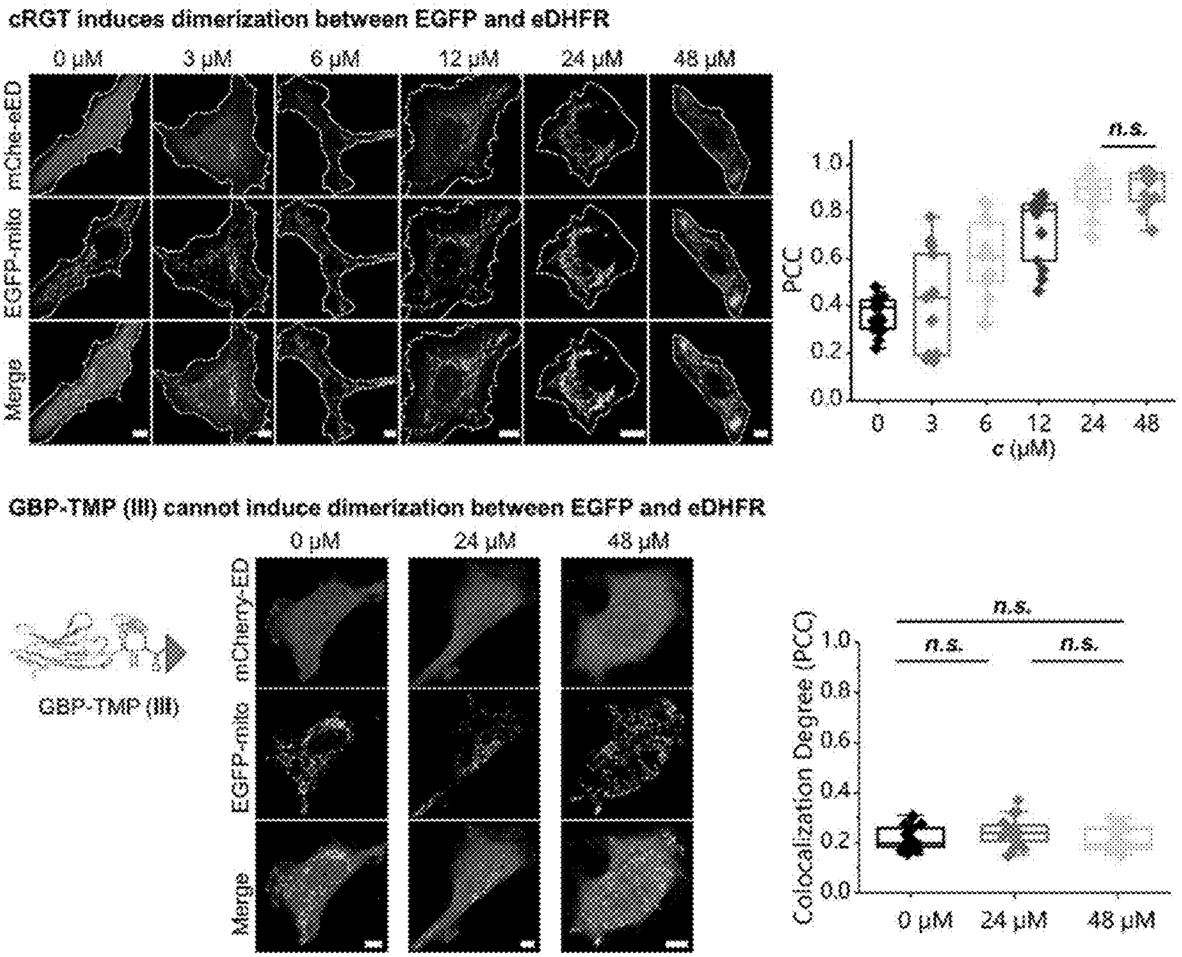
FIG. 5C shows that HeLa live cells were treated with cRGT of gradient concentrations (0, 3, 6, 12, and 24 μM) for 1.5 h, and it was found that an increasing degree of dimerization was induced; near-complete colocalization occurred after addition of 24 μM cRGT, showing a dose-dependent characteristic of cRGT-induced dimerization; statistical analysis of colocalization between EGFP and mCherry channels (n>10) by PCC was shown. In contrast, GBP-TMP without cR10* could not induce intracellular dimerization, which highlighted the importance of the cR10* moiety for cRGT-induced intracellular dimerization, and indicated that the part of GBP-TMP without the cR10* moiety in the cRGT product did not affect the regulation of intracellular processes by cRGT; statistical analysis between mCherry and EGFP channels by PCC. All scales: 10 μm.

The localization of mCherry-eDHFR in the cytoplasm to the mitochondria was concentration-dependent, with 24 μM cRGT being an optimal concentration (FIG. 5C). In contrast, a GBP-TMP nanobody conjugate without the cR10* module was unable to induce intracellular dimerization. Even the concentration was increased twice as 24 μM, i.e., 48 μM, intracellular dimerization could not be induced, demonstrating the necessity of the cR10* moiety for efficient intracellular delivery of cRGT (FIG. 5C).

Figure 6:
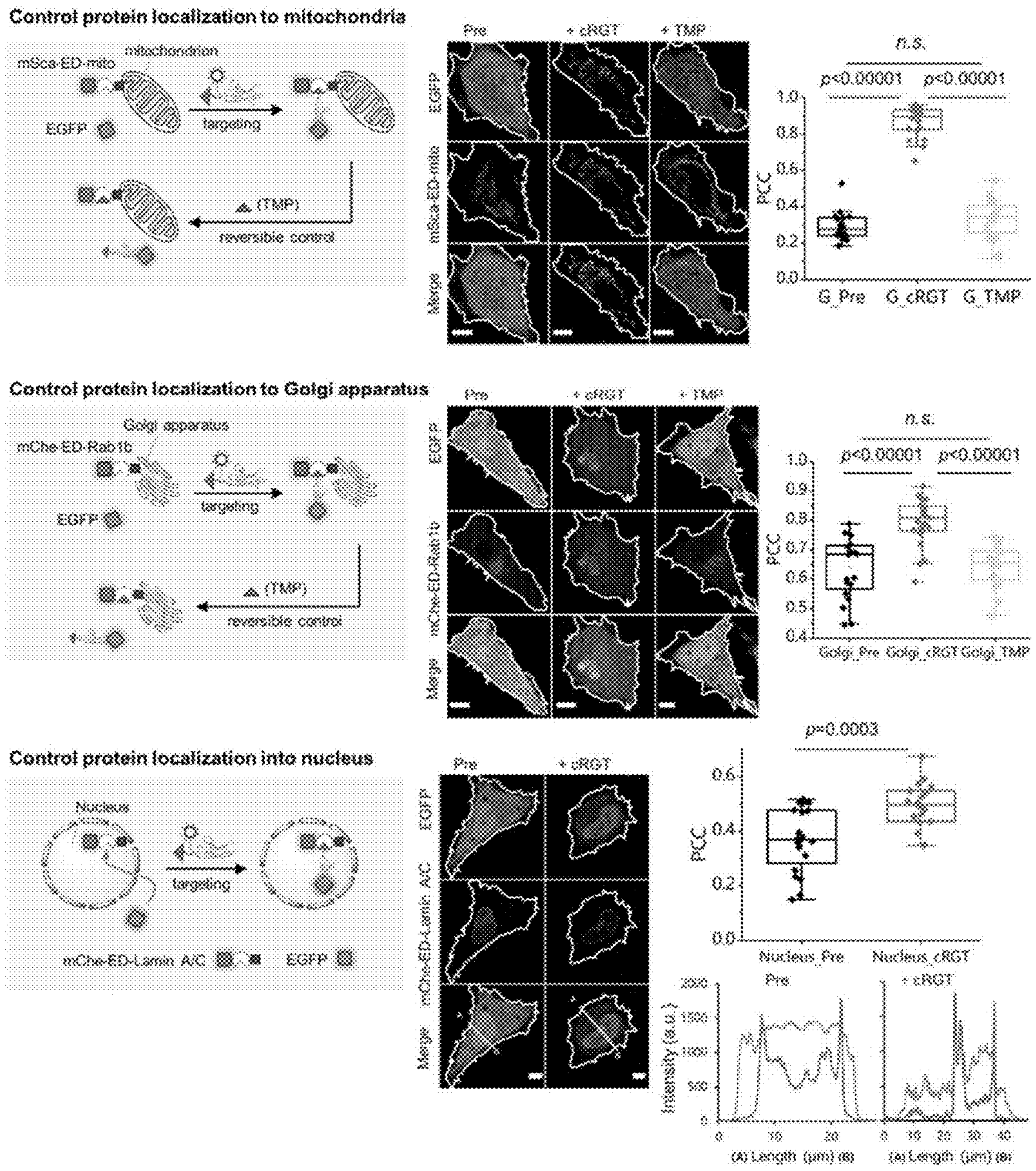
FIG. 6 shows regulation of localization of EGFP to different subcellular structural regions including mitochondria, Golgi apparatus and nucleus, by cRGT (24 μM, 1.5 h), and reversible control can be achieved using TMP (10 μM, 10 min). Abbreviations: mScarlet is abbreviated as mSca; mCherry is abbreviated as mChe; eDHFR is abbreviated as ED. All scales: 10 μm.

Example 5: CRGT Regulates Localization of EGFP to Different Intracellular Structures Many cellular processes are regulated by dynamic distribution of proteins in the cell. It was verified that cRGT could regulate the localization of EGFP to different subcellular structural regions, including mitochondria, Golgi apparatus and nuclear membrane subcellular regions. mScarlet-eDHFR-mito (mitochondria localized) and EGFP (distributed in cytoplasm) were co-expressed in HeLa cells. cRGT (24 μM, 1.5 h) localized EGFP from the cytoplasm to the mitochondrial outer membrane where mScarlet-eDHFR-mito was, and the localization was very complete. The localization regulation process was rapidly reversible by adding TMP (10 μM, 10 min) (FIG. 6). mCherry-eDHFR-Rab1b (Golgi apparatus localized) and EGFP are co-expressed in HeLa cells. Then treatment with cRGT (24 μM, 1.5 h) found that EGFP was localized from the cytoplasm to the Golgi apparatus where mCherry-eDHFR-Rab1b was. The localization regulation process was also rapidly reversible by adding TMP (10 μM, 10 min) (FIG. 6). mCherry-eDHFR-LaminA/C (localized to the inner nuclear membrane) and EGFP were co-expressed in HeLa cells. Then treatment with cRGT (24 μM, 1.5 h) found that EGFP was localized from the cytoplasm to the nuclear membrane where mCherry-eDHFR-Lamin A/C was (FIG. 6). This result was further confirmed by statistical PCC and a streak analysis method.

Figure 7A:
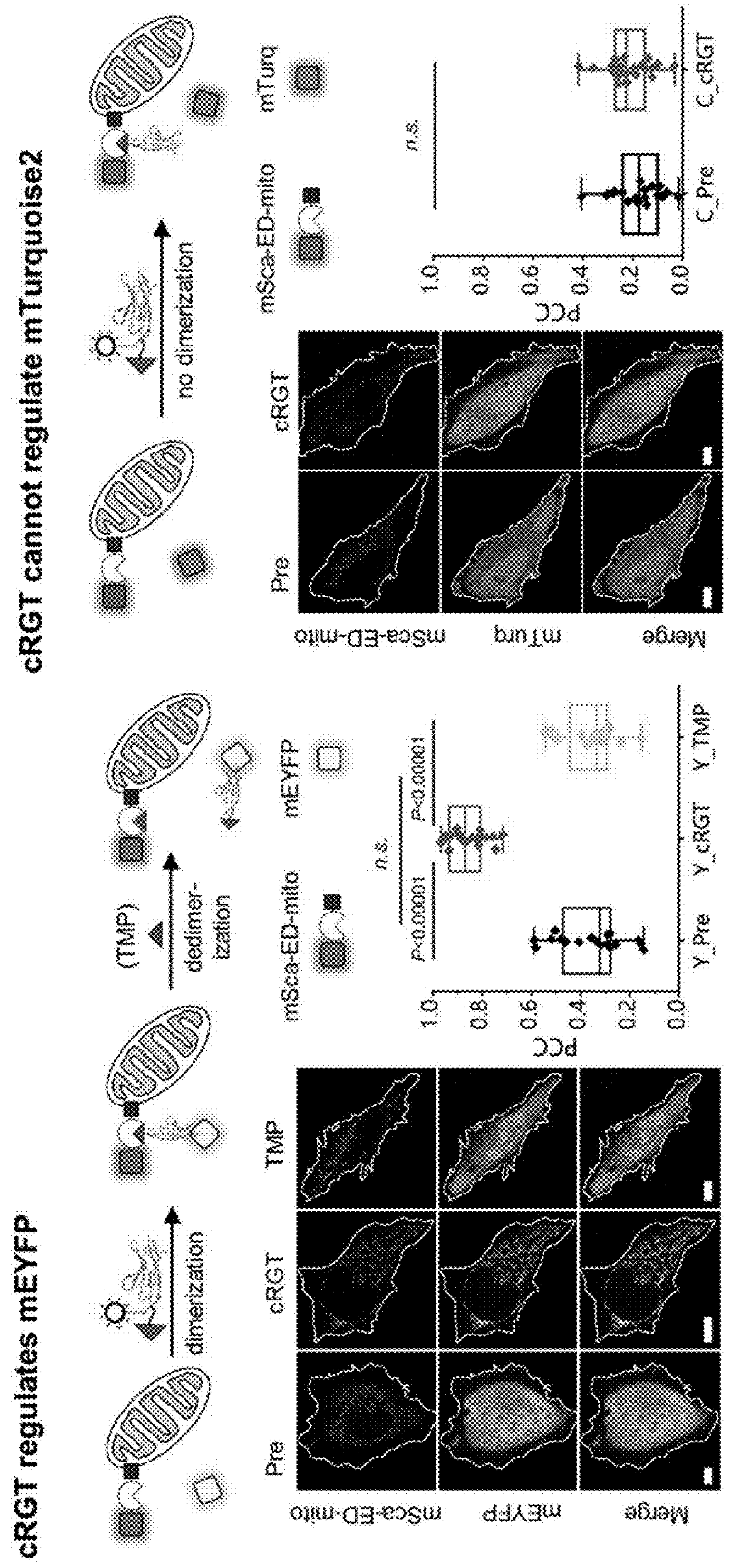
FIG. 7A shows the effect and orthogonality of regulation of other GFP mutants by cRGT. In this experiment, cRGT (24 μM, 1.5 h) localized another yellow fluorescent mutant (mEYFP) of GFP from the cytoplasm to the mitochondrial outer membrane where mScarlet-eDHFR-mito was, and the localization was very complete; and the localization regulation process was rapidly reversible by adding TMP (10 μM, 10 min); in contrast, cRGT was ineffective in regulation of mTurquoise2, another close turquoise fluorescent mutant of GFP, that is, the regulation of cRGT was orthogonal to the mTurquiose2 fluorescent protein.
Figure 7B:
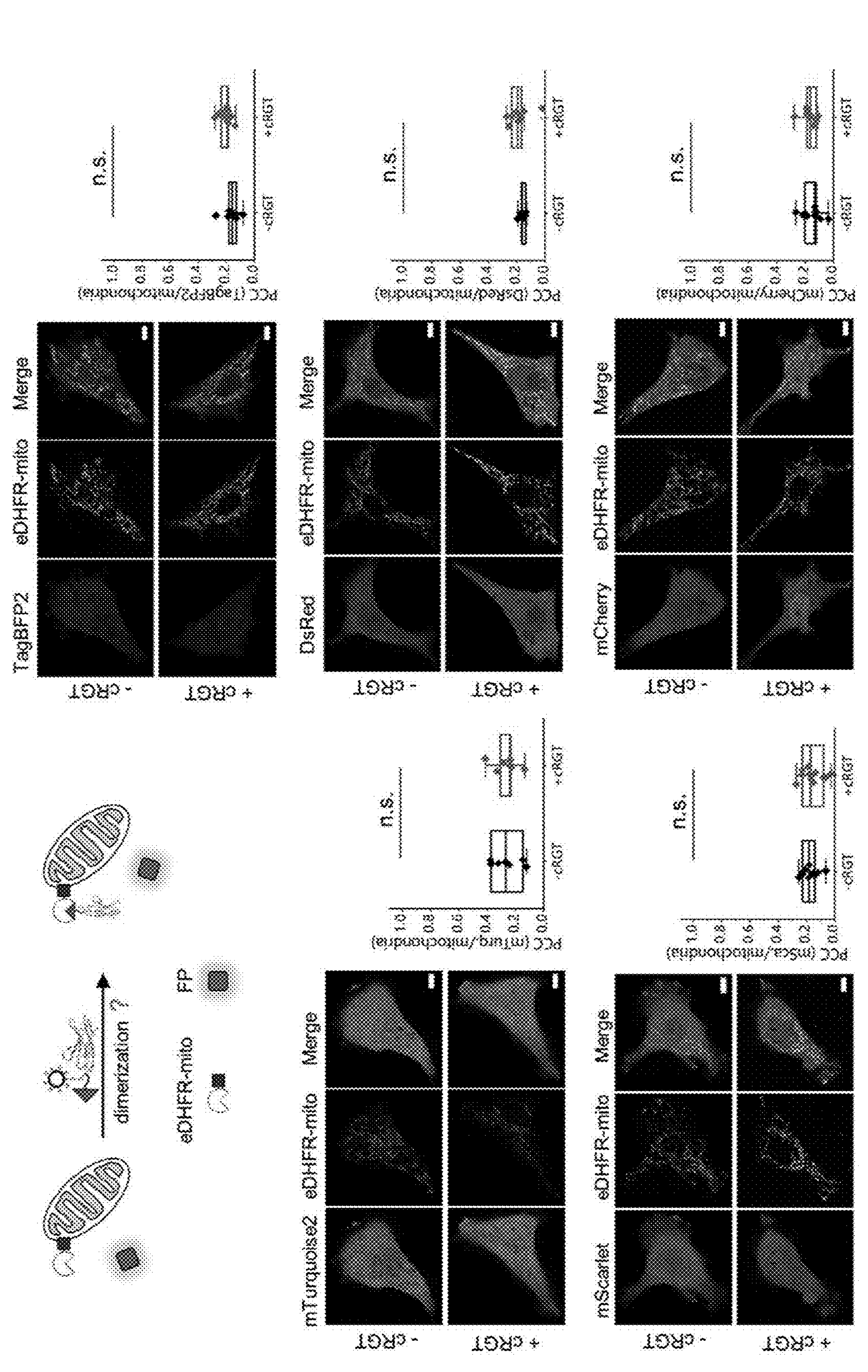
FIG. 7B shows that verification of the orthogonality of cRGT to other commonly used fluorescent proteins. After co-expression of eDHFR-mito (mitochondria localized) with TagBFP2, mTurquoise2, DsRed, mScarlet, or mCherry, living HeLa cells were treated with or without cRGT (24 μM, 1.5 h). Confocal micrographs and corresponding statistical analysis results by PCC showed that dimerization was not induced. Mitochondria were stained with mito-tracker green in all assays, except for the mTurquoise group were stained with mito-tracker red. All scales: 10 μm.

Example 6: CRGT can Also Regulate Localization of GFP Mutant Yellow Fluorescent mEYFP, while being Bioorthogonal to Other Commonly Used Fluorescent Proteins Yellow fluorescent protein mEYFP and turquoise fluorescent protein mTurquoise2 are close mutants of the GFP. It was found that the localization of mEYFP could be efficiently regulated by cRGT, but the localization of mTurquoise2 was not (FIG. 7A). This is an interesting phenomenon, but can also be reasonably explained: Asn146 in GFP, a residue that has a key hydrogen-bonding interaction with the Asn99 residue of GBP, is retained in EGFP and mEYFP, but is mutated to Ile146 in mTurquoise2. Using eDHFR-mito not fused with any fluorescent protein, it was further confirmed that the cRGT inducer of dimerization is completely orthogonal to other commonly used fluorescent proteins, including mTagBFP2, mTurquoise2, DsRed, mScarlet, and mCherry, spanned a spectral range from blue to scarlet (FIG. 7B). Therefore, cRGT is an all-rounder, can regulate the proteins of interest to which EGFP, mEYFP and eDHFR are fused, and also has good orthogonality to other fluorescent proteins.

Figure 8:
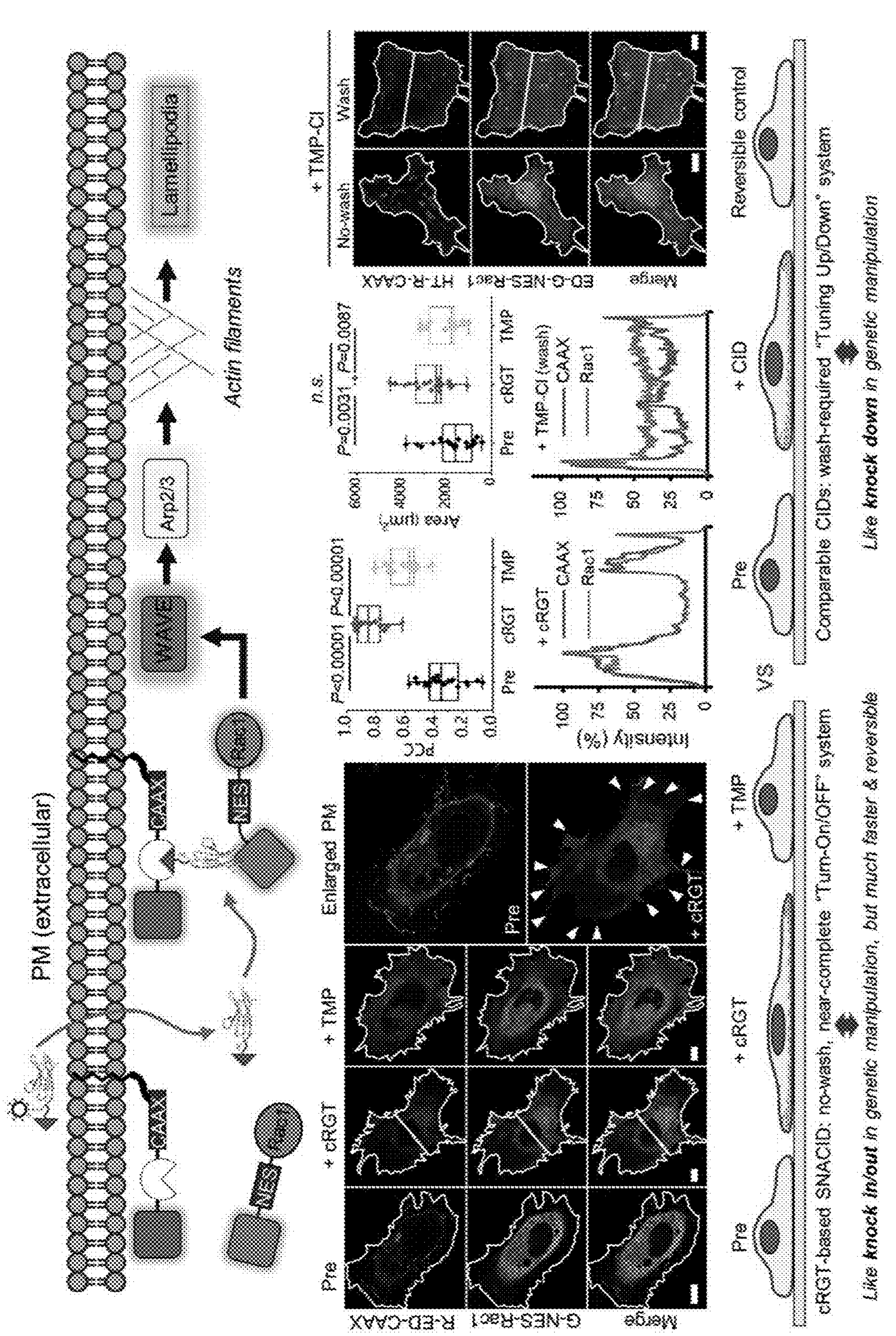
FIG. 8 shows cRGT activating a signaling cascade process during cell lamellipodia formation by localizing a signaling protein Rac1 to the inner side of the plasma membrane (PM). A constitutively active mutant EGFP-NES-Rac1Q61LΔCAAX (G-NES-Rac1 for short, green, cytoplasmic distribution) without the plasma membrane targeting ability and lacking the CAAX-box sequence and mCherry-eDHFR-CAAX (red, plasma membrane localized), being co-expressed in living HeLa cells; treatment of the HeLa cells with cRGT will localize the Rac1 mutant to the functional location of the plasma membrane, which in turn induces a signaling cascade process during lamellipodia formation. Confocal micrographs of representative living HeLa cells co-expressing G-NES-Rac1 and mCherry-eDHFR-CAAX, before treatment with cRGT (Pre), after treatment with 24 μM cRGT, and after addition of TMP at a final concentration of 10 μM. Statistical analysis of colocalization between the EGFP channel and the mCherry channel by PCC were shown. Statistical analysis of cell areas before treatment with cRGT (Pre), after treatment with 24 μM cRGT, and after treatment with TMP at a final concentration of 10 μM was also shown. Representative confocal micrographs, showing that after treatment of HeLa cells with a comparable CID (TMP-Cl, 10 μM, 1 h), whether eDHFR-EGFP-NES-Rac1Q61LΔCAAX (ED-G-NES-Rac1 for short) was localized to the plasma membrane before (left) and after (right) excess TMP-Cl was washed. Curve comparison of streak analysis of cells after dimerization induced by cRGT and TMP-Cl. Schematic flow charts, comparing a cRGT-based SNACIP proximity-induction system with a comparable conventional CID system in regulating intracellular processes. Abbreviations in the pictures: mCherry is abbreviated as mChe or R; EGFP is abbreviated as G; mTurquoise2 is abbreviated as mTurq or C; eDHFR is abbreviated as ED; HaloTag is abbreviated as HT. All scales: 10 μm.
Figure 9A:
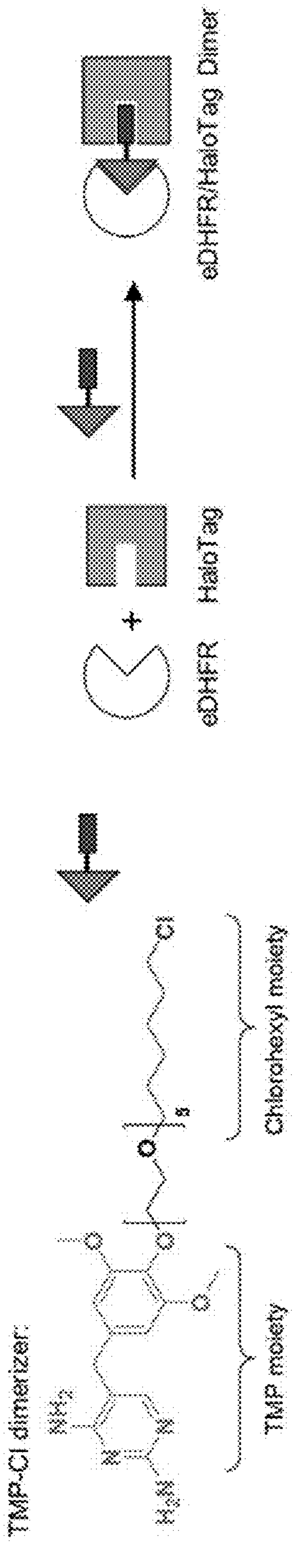
FIG. 9A shows the molecular structure of TMP-Cl, including a TMP moiety for binding eDHFR and a chlorohexyl moiety for covalently binding HaloTag. The dimerization between eDHFR and HaloTag can be induced by TMP-Cl.
Figure 9B:
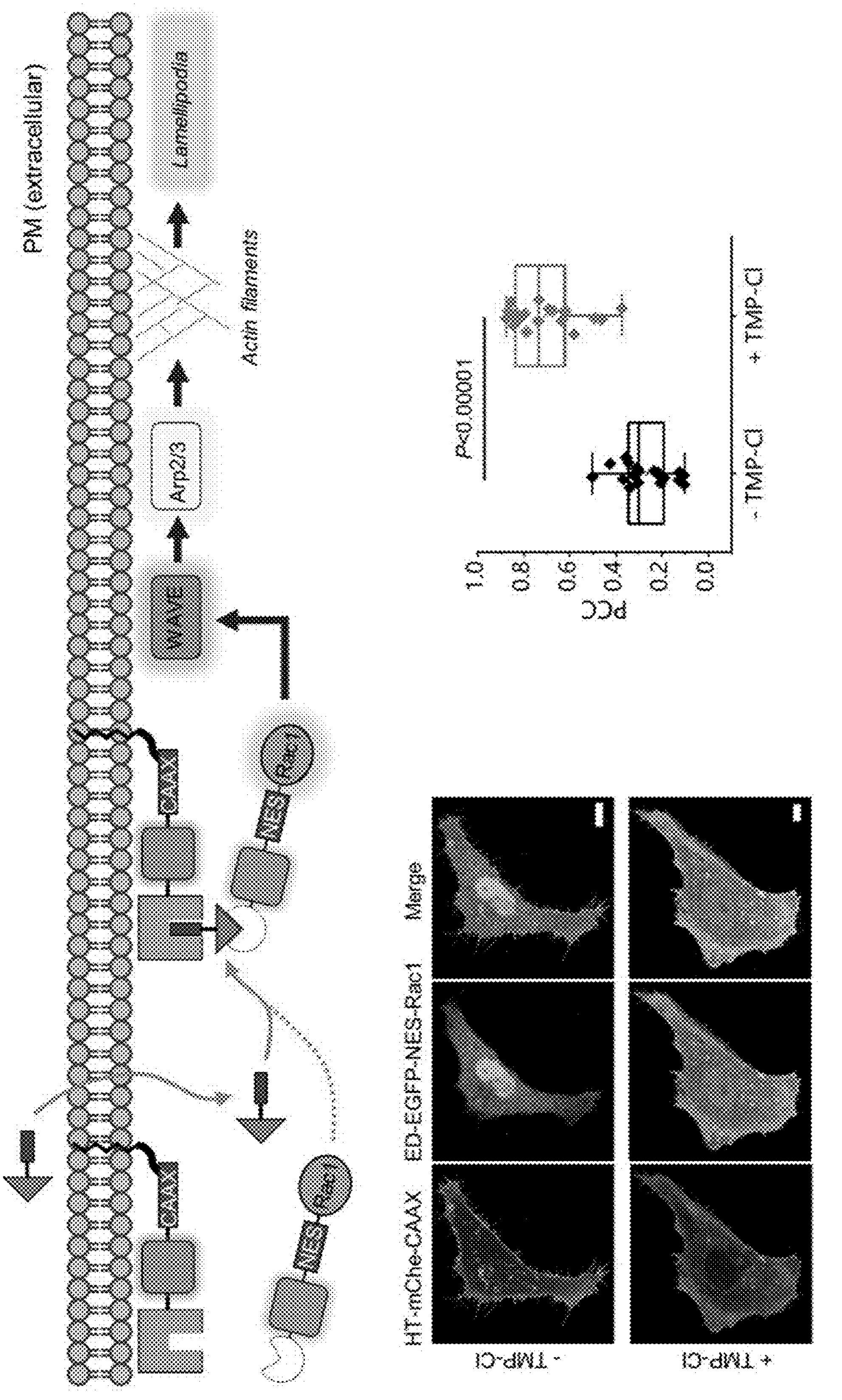
FIG. 9B shows the schematic view of TMP-Cl induced targeting of Rac1 to PM for activation of the signaling cascade of lamellipodia formation. WAVE: WASp-family verprolin-homologous protein; Arp2/3: actin-related protein-2/3. Confocal micrographs of representative living HeLa cells co-expressing HaloTag-mCherry-CAAX and eDHFR-EGFP-NES-Rac1 (Rac1 is an abbreviation for Rac1Q61LΔCAAX), with or without treatment with TMP-Cl (10 μM, 1 h, after which excess TMP-Cl was washed off, 30 min). Statistical analysis of colocalization by PCC, showing a moderate degree of colocalization PCC value around 0.7. Scale: 10 μm.

Example 7: CRGT Localizes Rac1 to the Plasma Membrane to Realize Regulation of Cell Signal Transduction Localization of proteins to the plasma membrane is a universal method for activating signaling cascades. To this end, we intended to use cRGT to regulate signal transduction. Rac1-mediated signal transduction plays a key role in the formation of lamellipodia, and also plays an important role in the metastasis and invasion of cancer cells. To this end, activation of the corresponding signaling transduction during lamellipodia formation by localizing Rac1 to the plasma membrane using cRGT was designed (FIG. 8). It was found that cRGT could clearly localize an active mutant of Rac1 to the functional location of the plasma membrane, while also inducing significant morphological changes of cells. The cells displayed a very elongated morphology and also produced a number of newly formed lamellipodia (FIG. 8, lower right, indicated by arrows in the micrographs). After 10 μM ofTMP was added, this process was completely reversed. After treatment with cRGT, the average area of cells increased from 1500 $\mu m^2$ to 2500 $\mu m^2$, while the average area of cells decreased significantly after the addition of TMP (FIG. 8). Compared with a comparable chemical inducer of dimerization, TMP-Cl (FIG. 9), cRGT can induce more complete cellular localization, indicating that the SNACIP system of dimerization has an excellent dynamic range (TMP-Cl synthesis method is shown in Reaction Scheme 2). Therefore, the cRGT-based SNACIP induction system of proximity has unique advantages over traditional CID chemical small molecules in the study of biological systems.

Figure 10A:
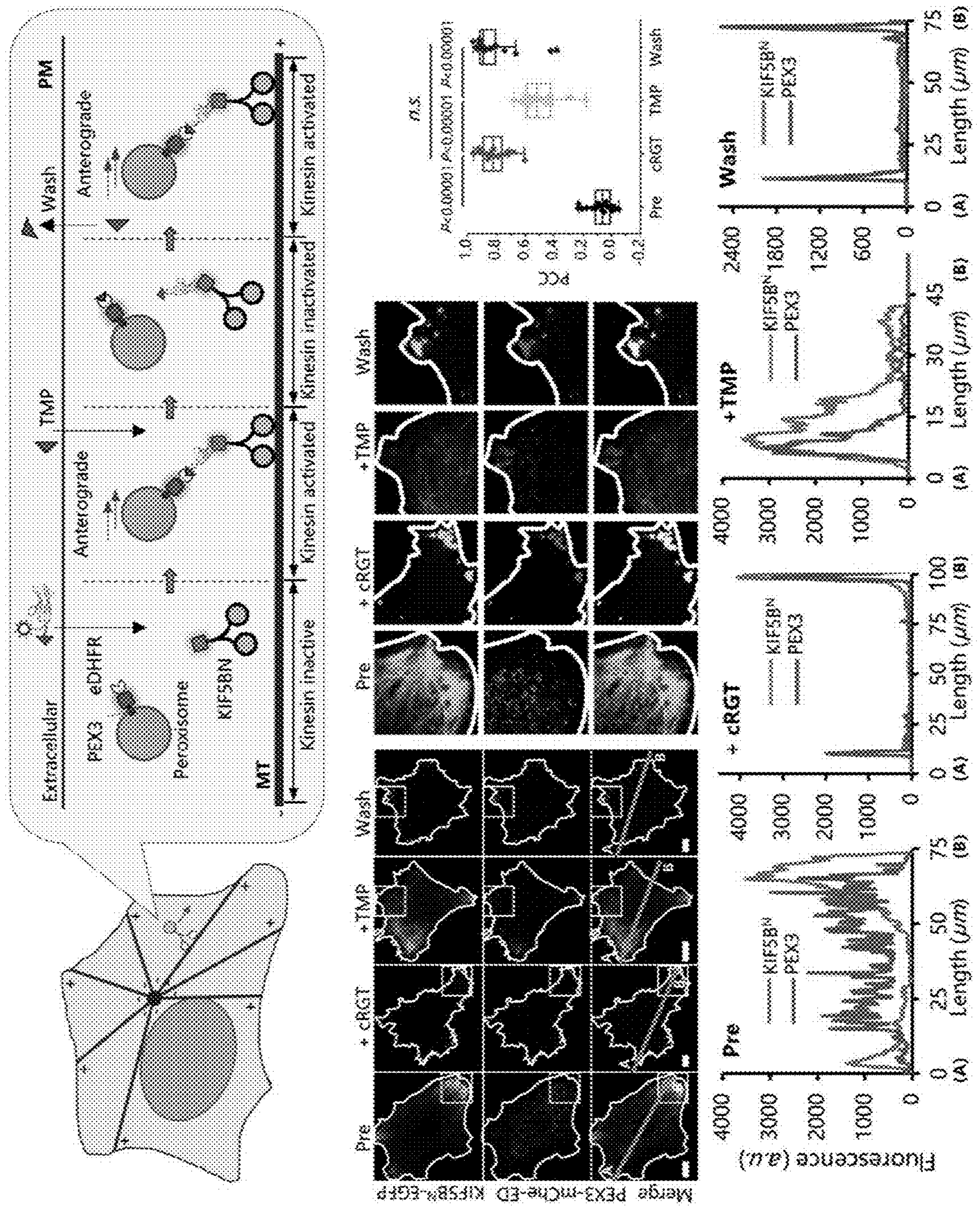
FIG. 10A shows near-complete multi-round reversible regulation of intracellular cargo transport by using cRGT. A flow chart, showing how cRGT cooperates with a TMP inhibitor to achieve multiple reversible regulations of KIF5B-mediated transport of a peroxisome "cargo", wherein KIF5BN can be activated by binding a N-terminal motor region (1-560) of KIF5B, i.e., KIF5BN, to a corresponding cargo, e.g., the peroxisome, and in turn stimulates forward transport along the microtubule, generally towards the edge region of the cell. Representative confocal micrographs, showing co-expression of PEX3-mCherry-eDHFR (peroxisome localized) and KIF5BN-EGFP, before addition of cRGT (Pre), after addition of 24 μM cRGT, after addition of TMP at a final concentration of 10 μM, and after TMP was washed off. Partially enlarged images clearly show details of individual peroxisomes and KIF5B localized on the peroxisomes. Statistical analysis of colocalization between the two channels by PCC was shown. Streak analysis of the confocal micrographs were shown.
Figure 10B:
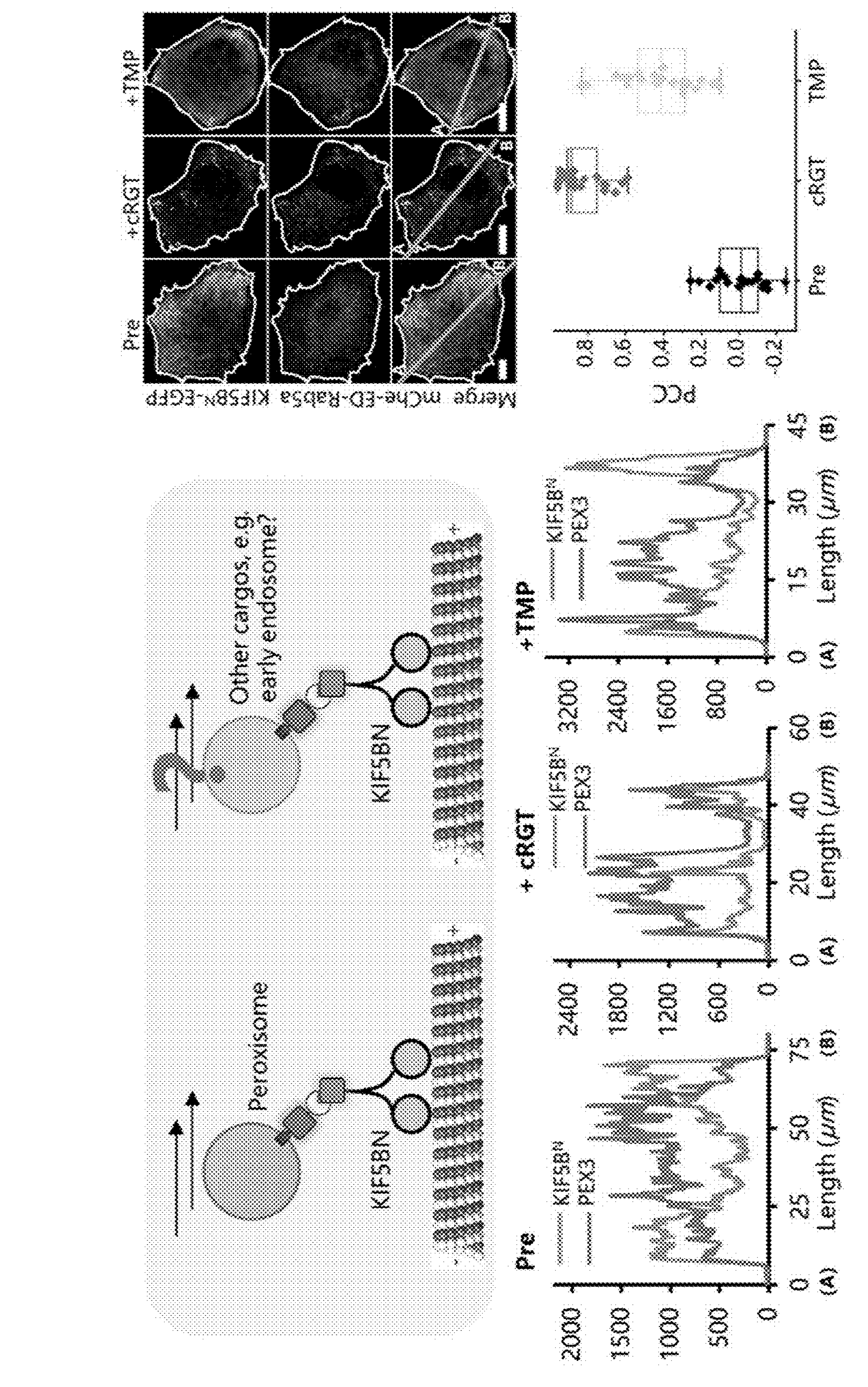
FIG. 10B shows the study on mutual specificity of kinesin-intracellular cargos by using the SNACIP inducers. A principle schematic diagram for investigating the cargo specificity of KIF5B kinesin was given. Representative confocal micrographs, showing living HeLa cells co-expressing mCherry-eDHFR-Rab5a (early endosome localized) and KIF5BN-EGFP, before addition of cRGT (Pre), after addition of 24 μM cRGT, and after addition of 10 μM TMP were also given. Streak analysis shows that cRGT does induce colocalization, but does not result in apparent transport from the early endosome towards the cell edge. Statistical analysis of colocalization between the two fluorescence channels by PCC was shown. All scales: 10 μm.

Example 8: CRGT Regulation by Localizing Kinesin to Intracellular Cargos and Study of Kinesin-Cargo Specificity Issues Next, SNACIP was used for studying biological issues. Kinesin-cargo specificity is an important issue during intracellular transport. However, many related issues remain unclear. To this end, it was first demonstrated that multiple reversible regulations of "off"-"on"-"off"-"on" of a kinesin-mediated cargo transport process can be achieved. This process could be achieved by washing out TMP small molecule inhibitors from the medium, further highlighting superior reversibility of SCNACID technology (FIG. 10A). Kinesin could be completely localized to a peroxisome "cargo" and could also be released from the "cargo". This process realizes reversible transport regulation of the peroxisome "cargo" along a microtubule to the cell edge, in a positive direction of the microtubule. Peroxisomes and early endosomes, i.e., two different intracellular "cargoes", were compared, and it was found that the peroxisomes, not the early endosomes, are the "cargoes" that can be efficiently transported by the KIF5B kinesin (FIG. 10B).

Example 9: CRGT Activates Ferroptosis by Regulating GPX4

Figure 11A:
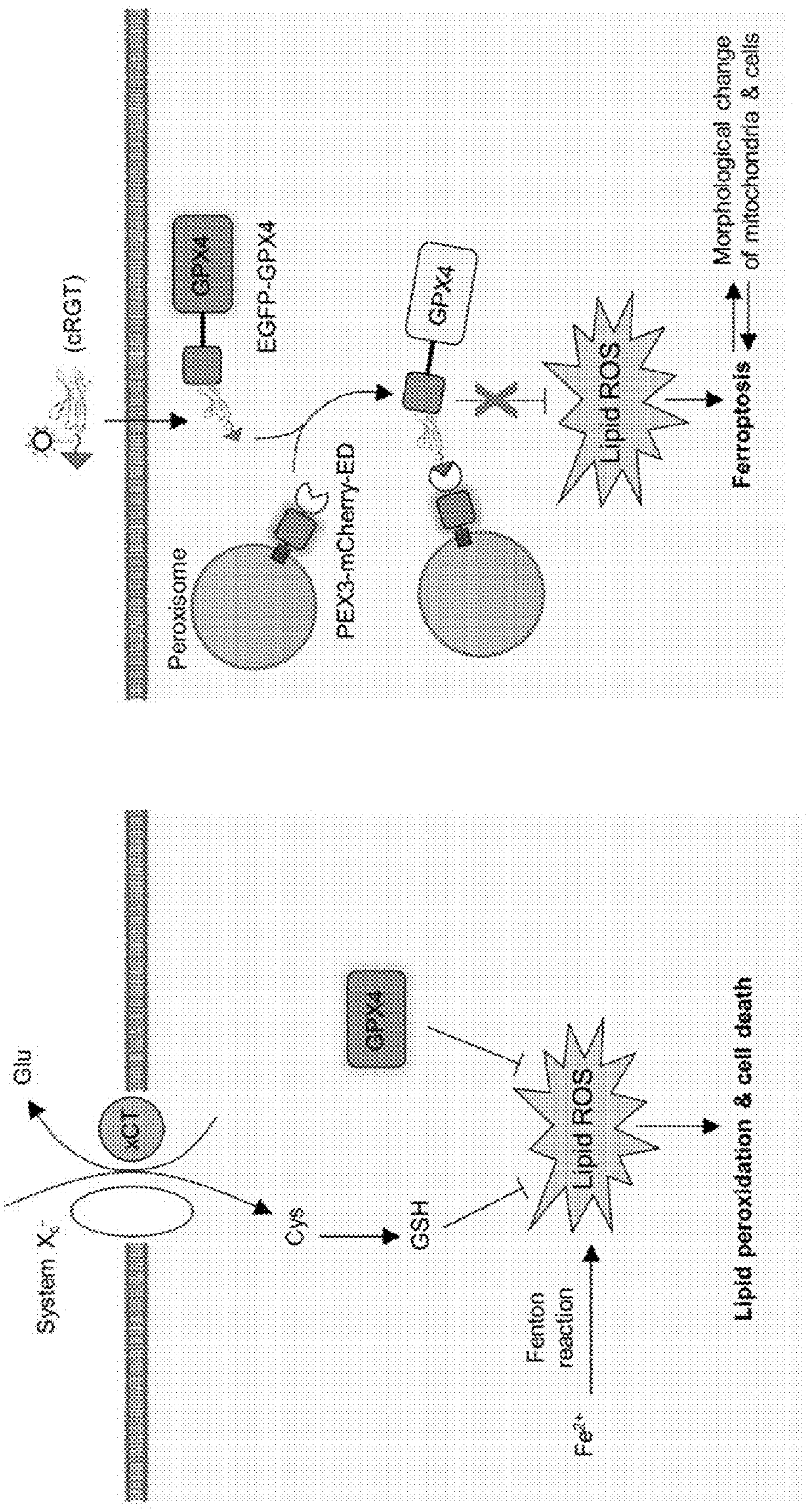
FIG. 11A shows the schematic diagram of the ferroptosis pathway, revealing the critical role of GPX4 factor in protecting cells from ferroptosis. A flow chart, showing how cRGT localizes EGFP-GPX4 to the surface of the peroxisome where PEX3-mCherry-ED is to inhibit GPX4, and then activate ferroptosis in cells. GPX4 was localized to a non-functional location, and selenocysteine in its catalytic active site might also be easily oxidized and inactivated to inhibit its negative regulation of ferroptosis.
Figure 11B:
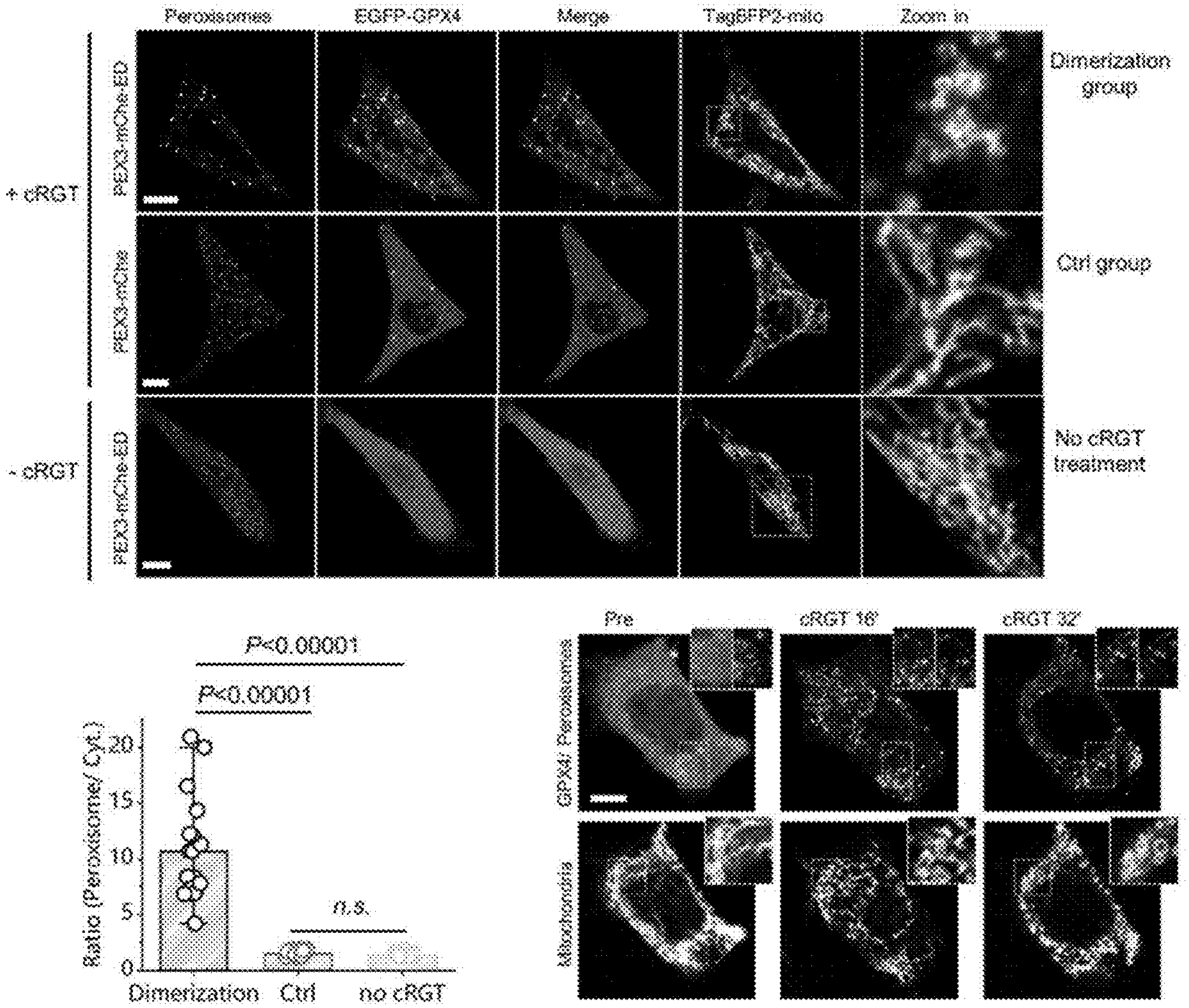
FIG. 11B shows that cRGT activates ferroptosis by regulating GPX4 to the surface of a peroxisome. Confocal micrographs of living HeLa cells co-expressing PEX3-mCherry-eDHFR (experimental group) or PEX3-mCherry (control group), EGFP-GPX4 and TagBFP2-mito (mitochondrial fluorescent tag) were shown; a non-cRGT treated group was also included. Cells were treated with cRGT (24 μM, 2 h) or without cRGT. The cells expressing EGFP-GPX4 in the experimental group were localized to peroxisomes and produce the classic morphology of ferroptotic cells, including smaller mitochondria, abnormal cell morphology, etc. In contrast, GPX4 in the control and non-cRGT treatment group were not localized to peroxisomes, the mitochondria were still in the state of a normal length, and the cell morphology was also normal. Statistic quantification of the average EGFP fluorescence ratio between peroxisomes region and cytosol region; one-sided Student's t-test was used (dimerization, n=18; Ctrl, n=15; no cRGT, n=19). A live HeLa cell was captured before adding cRGT (Pre), 16 min after adding cRGT (16'), and 32 min after adding cRGT (32'), which clearly showed the recruitment of GPX4 to peroxisomes and prominent morphological change of mitochondria along time. Scale: 10 μm.

Ferroptosis is a recently discovered non-apoptotic form of programmed cell death with iron-dependent properties, which is also accompanied by morphological changes in mitochondria and an increase in lipid reactive oxygen species (ROS). Targeting ferroptosis is currently speculated to be a novel and promising approach to killing drug-resistant cancer cells, as cancer cells exhibit a higher ferroptosis dependence than normal cells. Inspired by this, we considered activation of ferroptosis with cRGT. Among many ferroptosis-related factors, glutathione peroxidase 4 (GPX4) is considered to be one of the most important factors, which plays a role in protecting plasma membranes from peroxidative damage (FIG. 11A). In addition, a recent study showed that a number of peroxisomal components, including PEX3, were also found to contribute to ferroptosis sensitivity through CRISPR screening at the genome level. Accordingly, we predicted that localization of a ferroptosis inhibitor GPX4 to PEX3 on the surface of peroxisomes could inhibit the function of GPX4 and activate the ferroptosis process (FIG. 11A). It was found that living HeLa cells treated with cRGT (24 μM, 2 h) could efficiently localize EGFP-GPX4 to the peroxisome surface where PEX3-mCherry-eDHFR is, which was accompanied by obvious morphological changes of mitochondria and cells (FIG. 11B). Heteromorphic condensed mitochondria, smaller than normal mitochondria, and abnormally shaped cells were observed (FIG. 11B). These phenomena were totally consistent with the characteristics of classical ferroptotic cells, indicating that cRGT rapidly activated the ferroptosis process in cancer cells.

Example 10: Extension of the General-Purpose Inducer to Modulate Other Fluorescent Proteins Via Rapid Exchange of the Nanobody Module The above-mentioned examples show that cRGT-based SNACIP represents a general tool for control of cellular processes. In fact, the SNACIP concept is not limited to regulate only EGFP variants or eDHFR fused proteins. For example, the GBP nanobody can be facilely replaced by other nanobodies to further extend the application potential. In order to demonstrate this possibility, we employed a mCherry red fluorescent protein binding protein (RBP) nanobody. Setup the ligation between RBP-Intein and Cys-TMP requires less than 10 min and coupling of Cys-cR10* requires a few hours of work (FIG. 12A). Hence, a new SNACIP, cR10*-SS-RBP-TMP (i.e., cRRT), was assembled (FIG. 12A) using no more than two days of work. cRRT behaves similarly to cRGT and it induces dimerization at a high colocalization degree after 1.5 h at 24 μM concentration; the dimerization degree was not compromised when higher concentration of cRRT (48 μM) was used (FIG. 12B).

Example 11: Extension of the General-Purpose Type SNACIP Inducer to Induce the Dimerization Between EGFP and HaloTag Via Exchange of the Small Molecule Binding Motif A Cys-Cl ligand that features a cysteine moiety for EPL and a HaloTag ligand (chlorohexyl group) was prepared (Scheme 3). This was used to assemble a new SNACIP inducer called cR10*-SS-GBP-Cl, or (cRGC) (FIG. 13). cRGC is able to induce the dimerization between EGFP and HaloTag inside living cells. Living HeLa cells coexpressing EGFP and HT-mCherry-mito were treated with cRGC (24 μM, 1.5 h), and confocal microscopic imaging revealed that EGFP was recruited to HT-mCherry-mito on mitochondria (FIG. 13). This confirmed that cRGC is a new SNACIP inducer that allows localized covalent targeting of protein onto subcellular organelles.

Part 2: Design, Preparation, Characterization, and Cellular Regulatory Use of Latent SNACIP Inducer-cRTC

Example 12: Investigation and Selection of TPX2, a Key Microtubule Nucleator, as an Endogenous Target to Design the Corresponding SNACIP Inducer for Inhibiting Cell Division Endogenous ligand-free binding proteins are target proteins that are difficult to regulate by conventional CID methods. Among these ligand-free target proteins, intrinsically disordered proteins (IDPs) are a major class, and are currently receiving increasing attention due to their important biological functions. Microtubule nucleation is an important issue in the field of cytoskeleton. The structure of the microtubule nucleator—γTuRC, i.e., a gamma-tubulin cyclic complex, has been resolved. However, the structures of many other key factors in microtubule nucleation, e.g., an augmin complex and several nucleation factors belonging to the IDP class, remain enigmatic. Further, key microtubule nucleators are essential for cell division. Strict gene regulation methods such as gene knockout will directly lead to division blocked and death of cells, cannot establish corresponding gene knockout cell lines, and hence are not suitable for studying the effect of nucleation factors on cellular functions.

Intrinsically disordered protein TPX2 (Targeting Protein for Xklp2) is a key regulator of microtubule nucleation, which mediates the Ran signaling pathway during spindle assembly. As an oncoprotein, TPX2 is overexpressed in many cancer cells, including the most difficult-to-treat liver cancer (FIG. 14A). In view of this, we intended to design a latent SNACIP inducer for regulating the function of TPX2. A latent SNACIP inducer of dimerization features in a gene-encoded polypeptide sequence to be modified. An endogenous post-translational modification (PTM) machinery in living cells can be skillfully used for introducing a small-molecule binding moiety into the peptide sequence to be modified, thereby converting the latent SNACIP inducer of dimerization into a functional SNACIP regulatory inducer. This strategy can greatly facilitate construction of SNACIP inducers of dimerization, making covalent introduction of cR10* the only major bioconjugation step.

Example 13: Design, Preparation and Characterization of a Latent SNACIP Regulator—cRTC for Regulating Microtubule Nucleator Protein—hTPX2 During Uncontrolled Tumor Division Latent SNACIP inducer, cR10*-TBP-CAAX, or cRTC, was designed and constructed, which features by a nanobody containing a human TPX2 (hTPX2) binding protein (TBP), wherein the TBP nanobody has a cyclic cR10* cell-penetrating peptide at the N-terminal end and a CAAX box polypeptide sequence at the C-terminal end, and the CAAX box can be prenylated in a living cell (FIG. 14B). Here, isoprenyltransferase-catalyzed prenylation of the CAAX box is a well-studied post-translational modification mechanism. Once penetrating the cell, cRTC is converted into a functional farnesyl-cRTC SNACIP inducer and anchors on the inner side of the plasma membrane. Also, TBP nanobodies recruit endogenous hTPX2 proteins to the non-functional plasma membrane location, thereby depleting or reducing the level of TPX2 in the cytoplasm, and further inhibiting cell proliferation (FIG. 14B).

TPX2 nanobodies were successfully screened by phage display technology. hTPX2 antigen for phage display were prepared by TEV protease cleavage. hTPX2 is difficult to express well in *E. coli*, so first a pET28b(TEV)_hTPX2-TEV-EGFP-$His^8$ plasmid was constructed, which contained an EGFP tag, and can effectively promote expression of hTPX2. The plasmid has a $His^8$ tag at the C-terminal end, and an EGFP tag and a TEV cleavage site at the C-terminal end of hTPX2. hTPX2-TEV-EGFP-His8 was expressed in *E. coli* following the general protein expression scheme described previously. More specific steps are as follows. After IPTG was added for induction, *E. coli* Rosetta 2a was cultured overnight at 30 °C. After centrifugation, lysis, high-speed centrifugation and gradient Ni-IMAC purification are successively performed on the *E. coli*, hTPX2-TEV-EGFP-His8 dissolved in buffer A+(pH 8.0, i.e., solution A with an additional 3 mM of BME) was obtained. Then, an appropriate amount of TEV protease was added, the protein solution was incubated at 2 °C overnight, and hTPX2-TEV-EGFP-His8 was cleaved by enzyme, so that hTPX2 was cleaved from EGFP-His8. The protein solution was subjected to Ni-IMAC purification again, and hTPX2 was eluted with an imidazole-free buffer A+. The cleaved His8-containing fragment and the His-tag-fused protease bind more tightly to the nickel column, and can only be eluted at a higher concentration of imidazole to separate hTPX2. hTPX2 protein fractions were mixed, concentrated by ultrafiltration, and subjected to size exclusion chromatography using PBS as the eluent by a Superdex200 10/300 increase GL column. The PBS solutions of hTPX2 were mixed and concentrated by ultrafiltration, aliquoted, quickly frozen in liquid nitrogen, stored at −80 °C, and then used for nanobody screening in alpacas. To quantify protein concentration, typically 1 μl of protein sample is measured with a DS-11FX(+) DeNovix Spectrophotometer/Fluorometer. By measuring A280 and using M.W. and molar extinction coefficient E, a relatively accurate protein concentration can be measured: $c(mg\cdot ml^{-1})=[A280\times M.W.(g\cdot moL^{-1})]/\varepsilon\ (L\cdot moL^{-1}\cdot cm^{-1})$.

Next, the nanobody was prepared by M13 phage display technology, and a nanobody TBP (TPX2 binding protein) with high binding ability was screened. After that, the prepared TBP nanobody was expressed, purified and used for ITC measurement. First, pET28b(TEV)_His8-mCherry-TEV-TBP was cloned and expressed according to the scheme described above, and cultured overnight at 30 °C with shaking after IPTG induction. The purified TBP nanobody was thoroughly cleaved with an appropriate amount of TEV protease overnight at 2 °C. The protein solution was subjected to Ni-IMAC purification, and the TPX2 nanobody was eluted with an imidazole-free buffer A first and purified for subsequent analysis. The cleaved His8-mCherry fragment, His8-fused TEV protease and most impurities were removed due to high binding affinity to the nickel column, so a high-purity hTPX2 nanobody was prepared. Isothermal titration calorimetry (ITC) reveals that the binding $K_d$ value between TBP and hTPX2 was 287 nM with an equivalence ratio of 1:5. A negative value of ΔS also implies that the binding process is accompanied by a significant conformational change (FIG. 14C). The TBP is used for constructing the SNACIP inducer, cRTC.

Example 14: Design, Preparation and Characterization of a Latent SNACIP Regulator—cRTC for Regulating Microtubule Nucleator Protein—hTPX2 During Uncontrolled Tumor Division Next, one-pot preparation of cRTC was achieved by a tandem bioorthogonal ligation reaction starting from azide-functionalized TBP-CAAX (FIG. 14B). This preparation scheme allowed the cysteine residue in the CAAX box, which was necessary for subsequent prenylation, to remain completely unaffected and remain active throughout the ligation process. First, a Cys-TBP-CAAX (V) protein carrying an N-terminal cysteine could be easily obtained by TEV cleavage of His8-TEV'-TBP-CAAX. Afterwards, Cys-TBP-CAAX (V) was conjugated with bifunctional azidoCBT (ACBT, the synthesis method of ACBT is shown in reaction scheme 3) based on CBT ligation to obtain ACBT-TBP-CAAX (conjugate VI). At the same time, Cys-cR10* and a BCN-PEGr-Mal bifunctional linker obtained cR10*-BCN through an in situ Michael addition reaction. The cR10*-BCN could directly react with ACBT-TBP-CAAX (VI) through strain-promoted azide-alkyne cycloaddition (SPAAC) without isolation to obtain cRTC in one-pot (FIG. 14B). The whole ligation reaction process could be completed within 24 h. Notably, the CBT moiety is fluorogenic, facilitating subsequent analysis of intracellular localization and transport of cRTC.

In a representative reaction, the previously prepared Cys-TBP-CAAX protein was first exchanged into a PBS solution (pH 7.2, 1.78 $mg\cdot ml^{-1}$), and then 4 μl of ACBT (~10 mM, final concentration ~0.5 mM) could be added. After incubation at 2 °C overnight, and being confirmed by SDS-PAGE to be completely labeled, Cys-TBP-CAAX was exchanged into buffer A+ to obtain an ACBT-TBP-CAAX intermediate (1.95 $mg\cdot ml^{-1}$, 71 μl, 97% yield). At the same time, 15 μl of Cys-cR10* (25 mM/DMSO, 0.375 μmol) and 10 μl of BCN-PEG2-maleimide (25 mM/DMSO, 0.25 μmol) were sequentially added to 80 μl of PBS solution, and incubated at room temperature for ~1 h to complete a thiol-maleimide ligation reaction. 3.9 μl of the in situ ligation product cR10*-BCN (~24 mM, ~1.2 eq) was added to the ACBT-TBP-CAAX solution, and incubated for several hours to complete copper-free catalyzed click reaction labeling. After exchanging the solution into PBS, a cR10*-TBP-CAAX nanobody conjugate inducer of dimerization (1.52 $mg\cdot ml^{-1}$, 73 μl, 80% yield) was obtained, referred to as cRTC.

Example 15: CRTC Inhibits Cell Proliferation by Translocating hTPX2 to Non-Functional Location of Plasma Membrane The cRTC inducer clearly localized hTPX2 protein to the plasma membrane in HepG2 cells (FIG. 16A). The only Cys17 residue in the CAAX box of the TBP-CAAX protein was just mutated to Ser17 that cannot be prenylated, and it could be seen that plasma membrane localization of the protein completely disappeared. This result demonstrated that the Cys17 residue in the CAAX box of cRTC was indeed prenylated, thereby converting cRTC into a functional farnesyl-cRTC inducer of dimerization. Super-resolution fluorescence microscopy revealed that the cRTC regulatory inducer clearly colocalized with hTPX2 on the plasma membrane, and polarized condensate-formation was induced (FIG. 16B). This phenomenon is consistent with a phase separation behavior of TPX2 in vitro.

Next, whether downregulation of TPX2 activity with cRTC could inhibit cell proliferation was investigated. The results of an EdU cell proliferation assay showed that the EdU positive ratio of cRTC-treated HepG2 cells decreased, and the nuclear fluorescence intensity also significantly decreased (FIG. 16C). Another widely used HeLa cell assay showed a greater reduction in cell viability (FIG. 16C). Proportional changes in different phases of the cell cycle were further analyzed. S phase features EdU-positive cells, and cells in the division phase (M phase) can be easily identified by their unique morphology (dumbbell-shaped or spherical). Therefore, a histogram of changes in the HeLa cell cycle could be plotted, which showed that the proportion of cells in the S phase greatly decreased, while the cells in the M phase after cRTC treatment almost completely disappeared (FIG. 16D). Therefore, cRTC inhibiting the division process of tumor cells should be attributed to prevention of the M phase in the cell cycle.

Part 3: Design, Preparation, Cellular Regulation and Use In Vivo of Bivalent Nanobody SNACIP Inducer-CTTC

Example 16: Design and Preparation of Bivalent CTTC

An example of linear cell penetrating peptide (CPP) is a Tat polypeptide sequence.

Based on the above results, we predicted that the SNACIP inducers that regulate hTPX2 could be developed as SNACIP inducer drugs of proximity for inhibiting tumor proliferation in vivo. To better adapt cRTC for in vivo assays, a bivalent nanobody latent SNACIP regulatory inducer, mCherry-CPP-2×TBP-CAAX (CTTC) was designed and prepared, which included a tandem bivalent TBP nanobody, 2×TBP (FIG. 17A). Bivalent nanobodies have been confirmed to have higher antibody affinity and longer serum half-life than monovalent nanobodies. To prepare the bivalent CTTC inducer, the corresponding gene was cloned into a pET28b plasmid vector, which contained a His8 fusion tag at the N-terminal end. After expression, nickel column affinity purification was performed, and then molecular sieve purification was performed, thereby obtaining the corresponding latent bivalent CTTC, the SNACIP inducer, which can be used for in vivo therapy. The control CTT protein without a CAAX sequence, i.e., mCherry-CPP-2×TBP, could be expressed and purified in the same way.

Example 17: Bivalent CTTC can Penetrate Cells and Inhibit Cancer Cell Proliferation CTTC, a SNACIP inducer, was prepared, whose structural elements included a bivalent TBP nanobody, a Tat linear cell penetrating peptide, and a CAAX-box polypeptide sequence. After entering a cell, CTTC could be modified by prenylation to introduce a farnesyl group, and then converted into a functional SNACIP (FIG. 17A). It could be found that after HeLa cells were treated with CTTC (10 μM, 2 h), CTTC could penetrate the cell and localize to the plasma membrane, and also translocate hTPX2 to the plasma membrane (FIG. 17A). According to the results of an EdU cell proliferation assay, the brightness of the nuclei of HeLa cells treated with 10 μM CTTC significantly decreased (FIG. 17B), and the EdU positive ratio also greatly decreased (FIG. 17B). These results indicate that CTTC has an inhibitory effect on cancer cell proliferation.

Example 18: Bivalent CTTC Inhibits Tumor Growth In Vivo

Hepatocarcinoma xenograft mice model was obtained by injecting 5 million HepG2 hepatoma cells into the armpit of mice. It can be found that the tumor growth rate of the control group (PBS) was almost the same as that of the blank group. Only in the experimental group in which the mice were injected with CTTC, the tumor size began to decrease within 24 h after administration. At the same time, compared with the control and blank groups, tumor growth was also inhibited for a longer period of time (FIG. 17C). A non-SNACIP conventional bivalent nanobody chimera—CTT, was also designed and prepared, which only lacked a CAAX box compared with CTTC, and could not be converted into farnesyl-CTT, the SNACIP inducer (FIG. 18). Using new hepatocarcinoma xenograft mice models from the same group, CTTC clearly showed a greater tumor inhibitory effect than CTT (FIG. 18). These in vivo data further confirm the potential of SNACIP technology to regulate endogenous ligand-free binding targets, and further applied to drug development.

Example 19: Study of the Mechanism of SNACIP Inducers of TPX2 Inhibiting Cell Proliferation M phase is considered to be the most critical period during cell separation, and correct assembly of the bipolar spindle determines whether M phase can proceed. It is now generally accepted that the spindle is assembled through three key pathways: 1) chromosome-based, 2) centrosome-based, and 3) microtubule-based three pathways (FIG. 19*a*). Pathways i) and iii) are irreplaceable and essential, while the spindle can still assemble in the absence of centrosomes (as in plant cell spindles).

As an efficient system for studying the mechanism of spindle assembly, a *Xenopus* cell-free system has many advantages, especially good biochemical accessibility, that is, without the barrier of plasma membrane, any regulatory reagents (e.g., antibodies) can be directly added to interfere with the relevant biochemical processes. A *Xenopus* oocyte extract completely depleted of TPX2 was obtained by immunodepletion (FIG. 19). It was found that although the TPX2-depleted *Xenopus* oocyte extract could not form the spindle, the microtubule nucleation process was still intense, indicating that the chromosome-mediated microtubule nucleation pathway was still in place and had not been significantly inhibited (FIG. 19). In contrast, the microtubule-based nucleation pathway was greatly inhibited (FIG. 19). We therefore concluded that the SNACIP inducer of TPX2 prevents the proper assembly of the bipolar spindle by inhibiting the microtubule nucleation pathway, thereby blocking progression of the M phase, and further inhibiting cell division and proliferation.

What is claimed is:

1. A small molecule-nanobody conjugate inducer of proximity (SNACIP), comprising:

a small molecule binding motif, selected from the group consisting of a trimethoprim (TMP), a chlorohexyl, or a farnesyl, a nanobody targeting moiety, selected from the group consisting of a green fluorescent protein nanobody (GBP Nb), a red fluorescent protein nanobody (RBP Nb), and a a bivalent TPX2 (Targeting Protein for Xklp2 Binding Protein or TBP) nanobody, an intracellular delivery moiety, selected from the group consisting of a cell penetrating peptide (CPP) comprising a cyclic decaarginine (cR10*), a Tat peptide sequence comprising the amino acid sequence SEQ ID NO:11, and a CAAX peptide comprising SEQ ID NO:13, and a linker comprising a disulfide bond, a thioether bond, or a peptide bond, wherein the SNACIP is selected from:

(a) cR10*-GBP-TMP (cRGT) comprising the TMP, the GFP Nb, and the cR10*, (b) cR10*-TBP-CAAX (cRTC) comprising the cR10*, the TBP, and the CAAX peptide at the C-terminus, and
(c) mCherry-CPP-2×TBP-CAAX (CTTC) comprising the RBP Nb, a bivalent TPX2 nanobody, and the CAAX peptide.

* * * * *

SEQUENCE LISTING

```
Sequence total quantity: 15
SEQ ID NO: 1            moltype = DNA  length = 6706
FEATURE                 Location/Qualifiers
source                  1..6706
                        mol_type = other DNA
                        organism = synthetic construct
SEQUENCE: 1
aactacgtca ggtggcactt ttcggggaaa tgtgcgcgga acccctattt gtttattttt  60
ctaaatacat tcaaatatgt atccgctcat gagacaataa ccctgataaa tgcttcaata  120
atattgaaaa aggaagagta tgagtattca acatttccgt gtcgccctta ttcccttttt  180
tgcggcattt tgccttcctg tttttgctca cccagaaacg ctggtgaaag taaaagatgc  240
tgaagatcag ttgggtgcac gagtgggtta catcgaactg gatctcaaca gcggtaagat  300
ccttgagagt tttcgccccg aagaacgttc tccaatgatg agcactttta aagttctgct  360
```

-continued atgtggcgcg gtattatccc gtgttgacgc cgggcaagag caactcggtc gccgcataca 420
ctattctcag aatgacttgg ttgagtactc accagtcaca gaaaagcatc ttacggatgg 480
catgacagta agagaattat gcagtgctgc cataaccatg agtgataaca ctgcggccaa 540
cttacttctg acaacgatcg gaggaccgaa ggagctaacc gcttttttgc acaacatggg 600
ggatcatgta actcgccttg atcgttggga accggagctg aatgaagcca taccaaacga 660
cgagcgtgac accacgatgc ctgtagcaat ggcaacaacg ttgcgcaaac tattaactgg 720
cgaactactt actctagctt cccggcaaca attaatagac tggatggagg cggataaagt 780
tgcaggacca cttctgcgct cggcccttcc ggctggctgg tttattgctg ataaatctgg 840
agccggtgag cgtgggtctc gcggtatcat tgcagcactg gggccagatg gtaagccctc 900
ccgtatcgta gttatctaca cgacggggag tcaggcaact atggatgaac gaaatagaca 960
gatcgctgag ataggtgcct cactgattaa gcattggtaa ctgtcagacc aagtttactc 1020
atatatactt tagattgatt taccccggtt gataatcaga aaagccccaa aaacaggaag 1080
attgtataag caaatattta aattgtaaac gttaatattt tgttaaaatt cgcgttaaat 1140
ttttgttaaa tcagctcatt ttttaaccaa taggccgaaa tcggcaaaat cccttataaa 1200
tcaaaagaat agcccgagat agggttgagt gttgttccag tttggaacaa gagtccacta 1260
ttaaagaacg tggactccaa cgtcaaaggg cgaaaaaccg tctatcaggg cgatggccca 1320
ctacgtgaac catcacccaa atcaagtttt ttggggtcga ggtgccgtaa agcactaaat 1380
cggaacccta aagggagccc ccgatttaga gcttgacggg gaaagccggc gaacgtggcg 1440
agaaaggaag ggaagaaagc gaaaggagcg ggcgctaggg cgctggcaag tgtagcggtc 1500
acgctgcgcg taaccaccac acccgccgcg cttaatgcgc cgctacaggg cgcgtaaaag 1560
gatctaggtg aagatccttt ttgataatct catgaccaaa atcccttaac gtgagttttc 1620
gttccactga gcgtcagacc ccgtagaaaa gatcaaagga tcttcttgag atcctttttt 1680
tctgcgcgta atctgctgct tgcaaacaaa aaaaccaccg ctaccagcgg tggtttgttt 1740
gccggatcaa gagctaccaa ctctttttcc gaaggtaact ggcttcagca gagcgcagat 1800
accaaatact gtccttctag tgtagccgta gttaggccac cacttcaaga actctgtagc 1860
accgcctaca tacctcgctc tgctaatcct gttaccagtg gctgctgcca gtggcgataa 1920
gtcgtgtctt accgggttgg actcaagacg atagttaccg gataaggcgc agcggtcggg 1980
ctgaacgggg ggttcgtgca cacagcccag cttggagcga acgacctaca ccgaactgag 2040
atacctacag cgtgagctat gagaaagcgc cacgcttccc gaagggagaa aggcggacag 2100
gtatccggta agcggcaggg tcggaacagg agagcgcacg agggagcttc caggggggaaa 2160
cgcctggtat ctttatagtc ctgtcgggtt tcgccacctc tgacttgagc gtcgattttt 2220
gtgatgctcg tcaggggggc ggagcctatg gaaaaacgcc agcaacgcgg cctttttacg 2280
gttcctggcc ttttgctggc cttttgctca catgttcttt cctgcgttat cccctgattc 2340
tgtggataac cgtattaccg cctttgagtg agctgatacc gctcgccgca gccgaacgac 2400
cgagcgcagc gagtcagtga gcgaggaagc tatggtgcac tctcagtaca atctgctctg 2460
atgccgcata gttaagccag tatacactcc gctatcgcta cgtgactggg tcatggctgc 2520
gccccgacac ccgccaacac ccgctgacgc gccctgacgg gcttgtctgc tcccggcatc 2580
cgcttacaga caagctgtga ccgtctccgg gagctgcatg tgtcagaggt tttcaccgtc 2640
atcaccgaaa cgcgcgaggc agctgcggta aagctcatca gcgtggtcgt gcagcgattc 2700
acagatgtct gcctgttcat ccgcgtccag ctcgttgagt ttctccagaa gcgttaatgt 2760
ctggcttctg ataaagcggg ccatgttaag ggcggttttt tcctgtttgg tcactgatgc 2820
ctccgtgtaa gggggatttc tgttcatggg ggtaatgata ccgatgaaac gagagaggat 2880
gctcacgata cgggttactg atgatgaaca tgcccggtta ctggaacgtt gtgagggtaa 2940
acaactggcg gtatggatgc ggcgggacca gagaaaaatc actcagggtc aatgccagcc 3000
gaacgccagc aagacgtagc ccagcgcgtc ggccgccatg ccggcgataa tggcctgctt 3060
ctcgccgaaa cgtttggtgg cgggaccagt gacgaaggct tgagcgaggg cgtgcaagat 3120
tccgaatacc gcaagcgaca ggccgatcat cgtcgcgctc cagcgaaagc ggtcctcgcc 3180
gaaaatgacc cagagcgctg ccggcacctg tcctacgagt tgcatgataa agaagacagt 3240
cataagtgcg gcgacgatag tcatgccccg cgcccaccgg aaggagctga ctgggttgaa 3300
ggctctcaag ggcatcggtc gagatcccgg tgcctaatga gtgagctaac ttacattaat 3360
tgcgttgcgc tcactgcccg ctttccagtc gggaaacctg tcgtgccagc tgcattaatg 3420
aatcggccaa cgcgcgggga gaggcggttt gcgtattggg cgccagggtg gtttttcttt 3480
tcaccagtga gacgggcaac agctgattgc ccttcaccgc ctggccctga gagagttgca 3540
gcaagcggtc cacgctggtt tgccccagca ggcgaaaatc ctgtttgatg gtggttaacg 3600
gcgggatata acatgagctg tcttcggtat cgtcgtatcc cactaccgag atatccgcac 3660
caacgcgcag cccggactcg gtaatggcgc gcattgcgcc cagcgccatc tgatcgttgg 3720
caaccagcat cgcagtggga acgatgccct cattcagcat ttgcatggtt tgttgaaaac 3780
cggacatggc actccagtcg ccttcccgtt ccgctatcgg ctgaatttga ttgcgagtga 3840
gatatttatg ccagccagcc agacgcagac gcgccgagac agaacttaat gggcccgcta 3900
acagcgcgat ttgctggtga cccaatgcga ccagatgctc cacgcccagt cgcgtaccgt 3960
cttcatggga gaaaataata ctgttgatgg gtgtctggtc agagacatca agaaataacg 4020
ccggaacatt agtgcaggca gcttccacag caatggcatc ctggtcatcc agcggatagt 4080
taatgatcag cccactgacg cgttgcgcga gaagattgtg caccgccgct ttacaggctt 4140
cgacgccgct tcgttctacc atcgacacca ccacgctggc acccagttga tcggcgcgag 4200
atttaatcgc cgcgacaatt tgcgacggcg cgtgcagggc cagactggag gtggcaacgc 4260
caatcagcaa cgactgtttg cccgccagtt gttgtgccac gcggttggga atgtaattca 4320
gctccgccat cgccgcttcc actttttccc gcgttttcgc agaaacgtgg ctggcctggt 4380
tcaccacgcg ggaaacggtc tgataagaga caccggcata ctctgcgaca tcgtataacg 4440
ttactggttt cacattcacc accctgaatt gactctcttc cgggcgctat catgccatac 4500
cgcgaaaggt tttgcgccat tcgatggtgt ccgggatctc gacgctctcc cttatgcgac 4560
tcctgcatta ggaagcagcc cagtagtagg ttgaggccgt tgagcaccgc cgccgcaagg 4620
aatggtgcat gccggcatgc cgccctttcg tcttcaagaa ttaattccca attccccagg 4680
catcaaataa aacgaaaggc tcagtcgaaa gactgggcct ttcgttttat ctgttgtttg 4740
tcggtgaacg ctctcctgag taggacaaat ccgccgggag cggatttgaa cgttgcgaag 4800
caacggcccg gagggtggcg ggcaggacgc ccgccataaa ctgccaggaa ttaattcccc 4860
aggcatcaaa taaaacgaaa ggctcagtcg aaagactggg cctttcgttt tatctgttgt 4920
ttgtcggtga acgctctcct gagtaggaca aatccgccgg gagcggattt gaacgttgcg 4980
aagcaacggc ccggagggtg gcgggcagga cgcccgccat aaactgccag gaattaattc 5040
cccaggcatc aaataaaacg aaaggctcag tcgaaagact gggcctttcg ttttatctgt 5100

-continued

```
tgtttgtcgg tgaacgctct cctgagtagg acaaatccgc cgggagcgga tttgaacgtt  5160
gcgaagcaac ggcccggagg gtggcgggca ggacgcccgc cataaactgc caggaattaa  5220
ttccccaggc atcaaataaa acgaaaggct cagtcgaaag actgggcctt tcgttttatc  5280
tgttgtttgt cggtgaacgc tctcctgagt aggacaaatc cgccgggagc ggatttgaac  5340
gttgcgaagc aacggcccgg agggtggcgg gcaggacgcc cgccataaac tgccaggaat  5400
taattcccca ggcatcaaat aaaacgaaag gctcagtcga aagactgggc ctttcgtttt  5460
atctgttgtt tgtcggtgaa cgctctcctg agtaggacaa atccgccggg agcggatttg  5520
aacgttgcga agcaacggcc cggagggtgg cgggcaggac gcccgccata aactgccagg  5580
aattggggat cggaattaat tcccggttta aaccggggat ctcgatcccg cgaaattaat  5640
acgactcact ataggggaat tgtgagcgga taacaattcc cctctagaaa taattttgtt  5700
taactttaag aaggagatat acatatggct agctcgcgag tcgacggcgg ccgcgaattc  5760
ctcgagggct cttcctgcat cacgggagat gcactagttg ccctacccga gggcgagtcg  5820
gtacgcatcg ccgacatcgt gccgggtgcg cggcccaaca gtgacaacgc catcgacctg  5880
aaagtccttg accggcatgg caatcccgtg ctcgccgacc ggctgttcca ctccggcgag  5940
catccggtgt acacggtgcg tacggtcgaa ggtctgcgtg tgacgggcac cgcgaaccac  6000
ccgttgttgt gtttggtcga cgtcgccggg gtgccgaccc tgctgtggaa gctgatcgac  6060
gaaatcaagc cgggcgatta cgcggtgatt caacgcagcg cattcagcgt cgactgtgca  6120
ggttttgccc gcggaaaacc cgaatttgcg cccacaacct acacagtcgg cgtccctgga  6180
ctggtgcgtt tcttggaagc acaccaccga gacccggacg cccaagctat cgccgacgag  6240
ctgaccgacg ggcggttcta ctacgcgaaa gtcgccagtg tcaccgacgc cggcgtgcag  6300
ccggtgtata gccttcgtgt cgacacggca gaccacgcgt ttatcacgaa cgggttcgtc  6360
agccacgcta ctggcctcac cggtctgaac tcaggcctca cgacaaatcc tggtgtatcc  6420
gcttggcagg tcaacacagc ttatactgcg ggacaattgg tcacatataa cggcaagacg  6480
tataaatgtt tgcagcccca cacctccttg gcaggatggg aaccatccaa cgttcctgcc  6540
ttgtggcagc ttcaatgact gcaggaaggg gatccggctg ctaacaaagc ccgaaaggaa  6600
gctgagttgg ctgctgccac cgctgagcaa taactagcat aaccccttgg ggcctctaaa  6660
cgggtcttga ggggtttttt gctgaaagga ggaactatat ccggat                 6706
```

```
SEQ ID NO: 2           moltype = DNA  length = 717
FEATURE                Location/Qualifiers
source                 1..717
                       mol_type = other DNA
                       organism = synthetic construct
SEQUENCE: 2
atggtgagca agggcgagga gctgttcacc ggggtggtgc ccatcctggt cgagctggac  60
ggcgacgtaa acggccacaa gttcagcgtg tccggcgagg gcgagggcga tgccacctac  120
ggcaagctga ccctgaagtt catctgcacc accggcaagc tgcccgtgcc ctggcccacc  180
ctcgtgacca ccttcggcta cggcctgatg tgcttcgccc gctaccccga ccacatgaag  240
cagcacgact tcttcaagtc cgccatgccc gaaggctacg tccaggagcg caccatcttc  300
ttcaaggacg acggcaacta caagacccgc gccgaggtga agttcgaggg cgacaccctg  360
gtgaaccgca tcgagctgaa gggcatcgac ttcaaggagg acggcaacat cctggggcac  420
aagctggagt acaactacaa cagccacaac gtctatatca tggccgacaa gcagaagaac  480
ggcatcaagg tgaacttcaa gatccgccac aacatcgagg acggcagcgt gcagctcgcc  540
gaccactacc agcagaacac ccccatcggc gacggccccg tgctgctgcc cgacaaccac  600
tacctgagct accagtccaa gctgagcaaa gaccccaacg agaagcgcga tcacatggtc  660
ctgctggagt tcgtgaccgc cgccgggatc actctcggca tggacgagct gtacaag     717
```

```
SEQ ID NO: 3           moltype = DNA  length = 720
FEATURE                Location/Qualifiers
source                 1..720
                       mol_type = other DNA
                       organism = synthetic construct
SEQUENCE: 3
atggtgagca agggcgagga gctgttcacc ggggtggtgc ccatcctggt cgagctggac  60
ggcgacgtaa acggccacaa gttcagcgtg tccggcgagg gcgagggcga tgccacctac  120
ggcaagctga ccctgaagtt catctgcacc accggcaagc tgcccgtgcc ctggcccacc  180
ctcgtgacca ccctgtcctg gggcgtgcag tgcttcgccc gctaccccga ccacatgaag  240
cagcacgact tcttcaagtc cgccatgccc gaaggctacg tccaggagcg caccatcttc  300
ttcaaggacg acggcaacta caagacccgc gccgaggtga agttcgaggg cgacaccctg  360
gtgaaccgca tcgagctgaa gggcatcgac ttcaaggagg acggcaacat cctggggcac  420
aagctggagt acaactactt tagcgacaac gtctatatca ccgccgacaa gcagaagaac  480
ggcatcaagg ccaacttcaa gatccgccac aacatcgagg acggcggcgt gcagctcgcc  540
gaccactacc agcagaacac ccccatcggc gacggccccg tgctgctgcc cgacaaccac  600
tacctgagca cccagtccaa gctgagcaaa gaccccaacg agaagcgcga tcacatggtc  660
ctgctggagt tcgtgaccgc cgccgggatc actctcggca tggacgagct gtacaagtaa  720
```

```
SEQ ID NO: 4           moltype = DNA  length = 720
FEATURE                Location/Qualifiers
source                 1..720
                       mol_type = other DNA
                       organism = synthetic construct
SEQUENCE: 4
atggtgagca agggcgagga gctgttcacc ggggtggtgc ccatcctggt cgagctggac  60
ggcgacgtaa acggccacaa gttcagcgtg tccggcgagg gcgagggcga tgccacctac  120
ggcaagctga ccctgaagtt catctgcacc accggcaagc tgcccgtgcc ctggcccacc  180
ctcgtgacca ccctgaccta cggcgtgcag tgcttcagcc gctaccccga ccacatgaag  240
cagcacgact tcttcaagtc cgccatgccc gaaggctacg tccaggagcg caccatcttc  300
ttcaaggacg acggcaacta caagacccgc gccgaggtga agttcgaggg cgacaccctg  360
gtgaaccgca tcgagctgaa gggcatcgac ttcaaggagg acggcaacat cctggggcac  420
```

-continued

```
aagctggagt acaactacaa cagccacaac gtctatatca tggccgacaa gcagaagaac  480
ggcatcaagg tgaacttcaa gatccgccac aacatcgagg acggcagcgt gcagctcgcc  540
gaccactacc agcagaacac ccccatcggc gacggccccg tgctgctgcc cgacaaccac  600
tacctgagca cccagtccgc cctgagcaaa gaccccaacg agaagcgcga tcacatggtc  660
ctgctggagt tcgtgaccgc cgccgggatc actctcggca tggacgagct gtacaagtaa  720

SEQ ID NO: 5            moltype = AA  length = 159
FEATURE                 Location/Qualifiers
source                  1..159
                        mol_type = protein
                        organism = synthetic construct
SEQUENCE: 5
MISLIAALAV DRVIGMENAM PWNLPADLAW FKRNTLNKPV IMGRHTWESI GRPLPGRKNI  60
ILSSQPGTDD RVTWVKSVDE AIAACGDVPE IMVIGGGRVY EQFLPKAQKL YLTHIDAEVE  120
GDTHFPDYEP DDWESVFSEF HDADAQNSHS YCFEILERR                        159

SEQ ID NO: 6            moltype = DNA  length = 78
FEATURE                 Location/Qualifiers
source                  1..78
                        mol_type = other DNA
                        organism = synthetic construct
SEQUENCE: 6
ttaattcttg caatgttagc tattggcgtg ttctctttag ggcgtttat caaaattatt  60
caattaagaa aaaataat                                                78

SEQ ID NO: 7            moltype = DNA  length = 702
FEATURE                 Location/Qualifiers
source                  1..702
                        mol_type = other DNA
                        organism = synthetic construct
SEQUENCE: 7
atgagcgagc tgattaagga gaacatgcac atgaagctgt acatggaggg caccgtggac  60
aaccatcact tcaagtgcac atccgagggc gaaggcaagc cctacgaggg cacccagacc  120
atgagaatca aggtggtcga gggcggccct ctccccttcg ccttcgacat cctggctact  180
agcttcctct acggcagcaa gaccttcatc aaccacaccc agggcatccc cgacttcttc  240
aagcagtcct tccctgaggg cttcacatgg gagagagtca ccacatacga agacgggggc  300
gtgctgaccg ctacccagga caccagcctc caggacggct gcctcatcta caacgtcaag  360
atcagagggg tgaacttcac atccaacggc cctgtgatgc agaagaaaac actcggctgg  420
gaggccttca ccgagacgct gtaccccgct gacggcggcc tggaaggcag aaacgacatg  480
gccctgaagc tcgtgggcgg gagccatctg atcgcaaaca tcaagaccac atatagatcc  540
aagaaacccg ctaagaacct caagatgcct ggcgtctact atgtggacta cagactggaa  600
agaatcaagg aggccaacaa cgagacctac gtcgagcagc acgaggtggc agtggccaga  660
tactgcgacc tccctagcaa actggggcac aagcttaatt aa                    702

SEQ ID NO: 8            moltype = DNA  length = 696
FEATURE                 Location/Qualifiers
source                  1..696
                        mol_type = other DNA
                        organism = synthetic construct
SEQUENCE: 8
atggtgagca agggcgaggc agtgatcaag gagttcatgc ggttcaaggt gcacatggag  60
ggctccatga acggccacga gttcgagatc gagggcgagg gcgagggccg cccctacgag  120
ggcacccaga ccgccaagct gaaggtgacc aagggtggcc ccctgccctt ctcctgggac  180
atcctgtccc ctcagttcat gtacggctcc agggccttca tcaagcaccc cgccgacatc  240
cccgactact ataagcagtc cttccccgag ggcttcaagt gggagcgcgt gatgaacttc  300
gaggacggcg gcgccgtgac cgtgacccag gacacctccc tggaggacgg caccctgatc  360
tacaaggtga agctccgcgg caccaacttc cctcctgacg gccccgtaat gcagaagaag  420
acaatgggct gggaagcgtc caccgagcgg ttgtaccccg aggacggcgt gctgaagggc  480
gacattaaga tggccctgcg cctgaaggac ggcggccgct acctggcgga cttcaagacc  540
acctacaagg ccaagaagcc cgtgcagatg cccggcgcct acaacgtcga ccgcaagttg  600
gacatcacct cccacaacga ggactacacc gtggtggaac agtacgaacg ctccgagggc  660
cgccactcca ccggcggcat ggacgagctg tacaag                            696

SEQ ID NO: 9            moltype = DNA  length = 678
FEATURE                 Location/Qualifiers
source                  1..678
                        mol_type = other DNA
                        organism = synthetic construct
SEQUENCE: 9
atggcctcct ccgagaacgt catcaccgag ttcatgcgct tcaaggtgcg catggagggc  60
accgtgaacg gccacgagtt cgagatcgag ggcgagggcg agggccgccc ctacgagggc  120
cacaacaccg tgaagctgaa ggtgaccaag ggcggccccc tgcccttcgc ctgggacatc  180
ctgtcccccc agttccagta cggctccaag gtgtacgtga agcacccgc cgacatcccc  240
gactacaaga agctgtcctt ccccgagggc ttcaagtggg agcgcgtgat gaacttcgag  300
gacggcggcg tggcgaccgt gacccaggac tcctccctgc aggacggctg cttcatctac  360
aaggtgaagt tcatcggcgt gaacttcccc tccgacggcc ccgtgatgca gaagaagacc  420
atgggctggg aggcctccac cgagcgcctg tacccccgcg acggcgtgct gaagggcgag  480
acccacaagg ccctgaagct gaaggacggc ggccactacc tggtggagtt caagtccatc  540
tacatggcca agaagcccgt gcagctgccc ggctactact acgtggacgc caagctggac  600
```

-continued

```
atcacctccc acaacgagga ctacaccatc gtggagcagt acgagcgcac cgagggccgc  660
caccacctgt tcctgtag                                                678

SEQ ID NO: 10           moltype = DNA  length = 711
FEATURE                 Location/Qualifiers
source                  1..711
                        mol_type = other DNA
                        organism = synthetic construct
SEQUENCE: 10
atggtgagca agggcgagga ggataacatg gccatcatca aggagttcat gcgcttcaag  60
gtgcacatgg agggctccgt gaacggccac gagttcgaga tcgagggcga gggcgagggc  120
cgcccctacg agggcaccca gaccgccaag ctgaaggtga ccaagggtgg cccctgccc   180
ttcgcctggg acatcctgtc ccctcagttc atgtacggct ccaaggccta cgtgaagcac  240
cccgccgaca tccccgacta cttgaagctg tccttccccg agggcttcaa gtgggagcgc  300
gtgatgaact tcgaggacgg cggcgtggtg accgtgaccc aggactcctc cctgcaggac  360
ggcgagttca tctacaaggt gaagctgcgc ggcaccaact tcccctccga cggccccgta  420
atgcagaaga agaccatggg ctgggaggcc tcctccgagc ggatgtaccc cgaggacggc  480
gccctgaagg gcgagatcaa gcagaggctg aagctgaagg acggcggcca ctacgacgct  540
gaggtcaaga ccacctacaa ggccaagaag cccgtgcagc tgcccggcgc ctacaacgtc  600
aacatcaagt tggacatcac ctcccacaac gaggactaca ccatcgtgga acagtacgaa  660
cgcgccgagg gccgccactc caccggcggc atggacgagc tgtacaagta a           711

SEQ ID NO: 11           moltype = AA  length = 11
FEATURE                 Location/Qualifiers
source                  1..11
                        mol_type = protein
                        organism = synthetic construct
SEQUENCE: 11
YGRKKRRQRR R                                                       11

SEQ ID NO: 12           moltype = AA  length = 18
FEATURE                 Location/Qualifiers
source                  1..18
                        mol_type = protein
                        organism = synthetic construct
REGION                  7..12
                        note = circular peptide
SITE                    12
                        note = NH2
SEQUENCE: 12
CGGGGGKRRR RRRRRRRE                                                18

SEQ ID NO: 13           moltype = AA  length = 20
FEATURE                 Location/Qualifiers
source                  1..20
                        mol_type = protein
                        organism = synthetic construct
SEQUENCE: 13
KMSKDGKKKK KKSKTKCVIM                                              20

SEQ ID NO: 14           moltype = AA  length = 15
FEATURE                 Location/Qualifiers
source                  1..15
                        mol_type = protein
                        organism = synthetic construct
SEQUENCE: 14
TGTGTAATTA TGTAA                                                   15

SEQ ID NO: 15           moltype = AA  length = 15
FEATURE                 Location/Qualifiers
source                  1..15
                        mol_type = protein
                        organism = synthetic construct
SEQUENCE: 15
AGTGTAATTA TGTAA                                                   15
```